United States Patent [19]
Wilde et al.

[11] Patent Number: 5,491,152
[45] Date of Patent: Feb. 13, 1996

[54] DERIVATIVES OF CYCLIC ETHERS AND SULFIDES FOR THE TREATMENT OF ATHEROSCLEROSIS

[75] Inventors: Richard G. Wilde, Newark; Soo S. Ko, Wilmington, both of Del.; Jeffrey T. Billheimer, West Chester, Pa.

[73] Assignee: The Du Pont Merck Pharmaceutical Company, Wilmington, Del.

[21] Appl. No.: 216,723

[22] Filed: Mar. 23, 1994

[51] Int. Cl.⁶ .......................... A61K 31/38; A61K 31/44; C07D 405/12; C07D 409/12
[52] U.S. Cl. .......................... 514/336; 514/252; 514/256; 514/365; 514/374; 514/397; 514/406; 514/422; 514/431; 514/432; 514/443; 514/450; 514/456; 514/459; 514/469; 544/333; 544/405; 546/268; 548/204; 548/236; 548/315.1; 548/365.7; 548/561; 548/311.1; 549/9; 549/13; 549/23; 549/28; 549/57; 549/58; 549/355; 549/397; 549/401; 549/425; 549/463; 549/467; 549/72; 549/346; 549/487
[58] Field of Search .................. 549/13, 23, 28, 549/58, 401, 467, 9, 57, 355, 397, 425, 463; 544/333, 405; 546/268; 548/204, 236, 315.1, 365.7, 561, 311.1; 514/432, 443, 456, 469, 252, 256, 336, 365, 374, 397, 406, 422, 431, 450, 459

[56] References Cited

U.S. PATENT DOCUMENTS

| | | | |
|---|---|---|---|
| 4,623,662 | 11/1986 | DeVries | 514/596 |
| 4,722,927 | 2/1988 | Holmes | 514/256 |
| 4,824,843 | 4/1989 | Hoefle et al. | 514/228.8 |
| 4,868,210 | 9/1989 | Trivedi | 514/539 |
| 4,882,357 | 11/1989 | Creger et al. | 514/622 |
| 4,900,744 | 2/1990 | Billheimer et al. | 514/398 |

FOREIGN PATENT DOCUMENTS

| | | |
|---|---|---|
| 325397 | 7/1989 | European Pat. Off. . |
| 335374 | 10/1989 | European Pat. Off. . |
| 354994 | 2/1990 | European Pat. Off. . |
| 370740 | 5/1990 | European Pat. Off. . |
| 372445 | 6/1990 | European Pat. Off. . |
| 386487 | 9/1990 | European Pat. Off. . |
| 2418071 | 3/1991 | European Pat. Off. . |
| WO9109021 | 6/1991 | WIPO . |
| WO9110662 | 7/1991 | WIPO . |
| WO9113876 | 9/1991 | WIPO . |

OTHER PUBLICATIONS

Pfeifer et al, Tetrahedron Letters, 31 (40), pp. 5725–5728 (1990).

Kirby et al, J. Chem. Soc. Chem. Comm. (14), pp. 922–923 (1984).

*Primary Examiner*—Philip I. Datlow
*Attorney, Agent, or Firm*—Karen H. Kondrad; Blair Q. Ferguson

[57] ABSTRACT

The present invention provides compounds of Formula I,

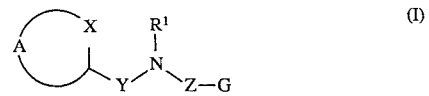

or a pharmaceutically acceptable salt forms thereof, which are inhibitors of acyl-Coenzyme A: cholesterol O-acyltransferase (ACAT), pharmaceutical compositions containing such compounds, processes for the preparation of such compounds, and the use of such compounds as antihypercholesterolemic and/or antiatherosclerotic agents.

15 Claims, No Drawings

DERIVATIVES OF CYCLIC ETHERS AND SULFIDES FOR THE TREATMENT OF ATHEROSCLEROSIS

FIELD OF THE INVENTION

This invention provides compounds which are derivatives of cyclic ethers and sulfides, as inhibitors of acyl-Coenzyme A: cholesterol O-acyltransferase (ACAT), pharmaceutical compositions containing such compounds, processes for the preparation of such compounds, and the use of such compounds as antihypercholesterolemic and/or antiatherosclerotic agents.

BACKGROUND OF THE INVENTION

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol-carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must first be esterified by ACAT prior to its incorporation and secretion into the bloodstream in large lipoprotein particles called chylomicrons, inhibition of ACAT can reduce the absorption of dietary cholesterol. In addition, the accumulation and storage of cholesteryl esters in the arterial wall is associated with increased activity of ACAT. Inhibition of the enzyme is expected to inhibit the formation or progression of atherosclerotic lesions in mammals.

There are an increasing number of patents in the literature disclosing compounds which are useful as ACAT inhibitors in particular and antiatherosclerotic agents in general. For example, U.S. Pat. No. 4,623,662, issued to DeVries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol. U.S. Pat. No. 4,824,843, issued to Hoefle et al. on Apr. 25, 1989, and the related U.S. Pat. No. 4,882,357, issued to Creger et al. on Nov. 21, 1989, disclose a series of substituted N-phenyl-2,2-dimethyl-5-aryloxypentanamides, which prevent the intestinal absorption of cholesterol in mammals by inhibiting ACAT. European Patent Application 325,397, filed by Ito on Jul. 26, 1989, discloses a series of compounds consisting of two N-cycloalkyl-N'-arylurea units linked at nitrogen by a dialkylphenyl unit, which are inhibitors of the ACAT enzyme. U.S. Pat. No. 4,868,210, issued to Trivedi on Sep. 19, 1989, and the related European Patent Applications 335,374 filed by Trivedi on Mar. 30, 1988 and 386,487, filed by Trivedi on Feb. 9, 1989, disclose certain N-2,6-dialkyl- or N-2,6-dialkoxyphenyl-N' arylalkyl ureas as potent inhibitors of ACAT. European Patent Application 354,994, filed by Meguro and Ikeda on Feb. 21, 1990, discloses certain N-aryl-N'-quinolin-4-yl ureas as ACAT inhibitors. European Patent Application 370,740, filed by Jackson et al. on Nov. 21, 1988, discloses ACAT inhibitors similar in composition to those of DeVries (supra).

The following references also disclose compounds which are inhibitors of ACAT useful as antihypercholesterolemic and/or antiatherosclerotic agents: U.S. Pat. No. 4,900,744; European Patent Application EP-A-372,445; International Application WO 91/09021; International Application WO 91/10662; International Application WO 91/13876; German Laid Open Application No. DE 3504679; German Laid Open Application No. DE 3504680.

European Patent Application EP 418,071 A2, filed by McCarthy et al., discloses compounds of the formula

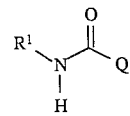

wherein
Q is —$CR^2R^3R^4$ or —$NR^{17}R^{18}$;
$R^1$ is

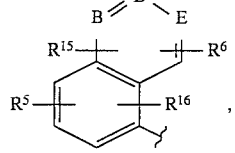

XXIV

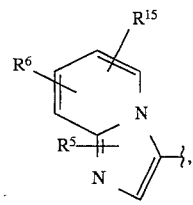

XXV

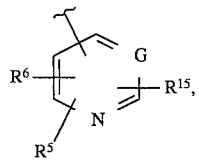

XXVI or

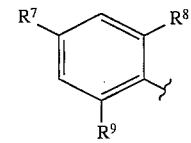

XXVII $R^2$, $R^3$ and $R^4$ may be the same or different, and (a) are selected from the group consisting of hydrogen, $C_1$–$C_4$ alkyl, A, $XR^{10}$, $C_7$–$C_{13}$ arylalkyl, $C_6$–$C_{12}$ cycloalkylalkyl, with the proviso that at least one of $R^2$, $R^3$ and $R^4$ must be A, and with the proviso that when $R^1$ is a group of the formula XXVII or a group of the formula XXVI wherein G is nitrogen and wherein neither $R^5$, $R^6$ or $R^{15}$ is $NR^{19}R^{20}$, $C_1$–$C_6$ alkylthio, $C_5$–$C_7$ cycloalkylthio, $C_7$–$C_{11}$ arylalkylthio, phenylthio or heteroalkylthio, either at least one of $R^2$, $R^3$ and $R^4$ must be $XR^{10}$, or two of $R^2$, $R^3$ and $R^4$ must be A; or (b) $R^2$ and $R^3$ together with the carbon to which they are attached form a cyclic or bicyclic system selected from the group consisting of $C_3$–$C_7$ cycloalkyl, $C_3$–$C_7$ cycloalkenyl, $C_6$–$C_{14}$ bicycloalkyl, $C_6$–$C_{14}$ bicycloalkenyl, and aryl-fused and heteroaryl-fused systems containing 8 to 15 carbon atoms, one ring of any of said aryl-fused and heteroaryl-fused systems being aromatic and the ring containing the carbon to which $R^2$ and $R^3$ are attached being non-aromatic, one of the carbons of said aromatic ring being optionally replaced by sulfur or oxygen, one or more carbons of said non-aromatic ring being optionally replaced by sulfur or oxygen, and one or more carbons of said aromatic ring being optionally replaced by nitrogen; one or two carbons of said cycloalkyl or bicycloalkyl groups being optionally replaced by sulfur or oxygen, and said cylic or bicyclic system being optionally substituted with one to five substituents independently selected from the group consisting of phenyl, substituted phenyl, $C_1$–$C_6$ alkyl and A, with the proviso that one and only one of said substituents is A, and one and only one of said substituents is phenyl or substituted phenyl, said substituted phenyl being substituted with one or more substituents independently selected from the group consisting of $C_1$–$C_6$ alkyl, $C_1$–$C_6$ alkylthio, halogen and trifluoromethyl; and $R^4$ is H, $XR^{10}$ or A;

with the proviso that when $R^1$ is a group of the formula XXVII or a group of the formula XXVI wherein G is nitrogen and wherein neither $R^5$, $R^6$ nor $R^{15}$ is $NR^{19}R^{20}$, $C_1$–$C_6$ alkylthio, $C_5$–$C_7$ cycloalkylthio, phenyl $C_1$–$C_4$ alkylthio, phenylthio or heteroalkylthio, $R^2$ and $R^3$, together with the carbon to which they are attached, do not form a $C_3$–$C_7$ cycloalkyl ring containing only carbon atoms;

A is a hydrocarbon containing 4 to 16 carbons and 0, 1 or 2 double bonds;

X is O, S, SO, $SO_2$, NH, $NR^{23}CO$ or $NSO_2R^{24}$, wherein $R^{23}$ is hydrogen or $C_1$–$C_6$ alkyl and $R^{24}$ is $C_1$–$C_6$ alkyl, phenyl or $C_1$–$C_3$ alkyl-phenyl;

$R^5$, $R^6$, $R^{15}$ and $R^{16}$ are each independently selected from the group consisting of hydrogen, F, Cl, I, Br, $C_1$–$C_4$ alkyl, $C_1$–$C_4$ haloalkyl, $C_1$–$C_4$ alkoxy, $C_1$–$C_6$ alkylthio, $C_5$–$C_7$ cycloalkylthio, phenyl $C_1$–$C_4$ alkylthio, substituted phenylthio, heteroarylthio, heteroaryloxy, and $NR^{19}R^{20}$, wherein $R^{19}$ and $R^{20}$ are the same or different and are selected from the group consisting of hydrogen, $C_1$–$C_4$ alkyl, phenyl, substituted phenyl, $C_1$–$C_4$ acyl, aroyl, and substituted aroyl, wherein said substituted phenyl and substituted aroyl groups are substituted with one or more substituents independently selected from the group consisting of $C_1$–$C_6$ alkyl, $C_1$–$C_6$ alkoxy, $C_1$–$C_6$ alkylthio, halogen and trifluoromethyl, or $R^{19}$ and $R^{20}$, together with the nitrogen to which they are attached, form a piperidine or morpholine ring; and wherein $R^5$, $R^6$, $R^{15}$ and $R^{16}$, when attached to a bicyclic system, may be attached to either ring of such system, with the proviso that no more than 3 non-hydrogen substituents may be attached to any one ring of such system;

$R^7$, $R^8$ and $R^9$ are the same or different;

$R^7$ is selected from the group consisting of hydrogen, $C_1$–$C_4$ alkoxy, $C_1$–$C_4$ alkylthio, methyl and fluoro; and $R^8$ and $R^9$ are each independently selected from the group consisting of $C_1$–$C_4$ alkoxy, $C_1$–$C_4$ alkylthio, methyl, and fluoro;

$R^{10}$ is selected from the group consisting of $C_4$–$C_{12}$ cycloalkyl, $C_4$–$C_{12}$ straight or branched alkyl, $C_4$–$C_{12}$ cycloalkyl-$C_1$–$C_6$ alkyl, phenyl-$C_1$–$C_6$ alkyl, substituted phenyl-$C_1$–$C_6$ alkyl, $C_1$–$C_6$ alkylphenyl, $C_1$–$C_6$ alkyl-substituted phenyl, optionally-substituted thiazoles, optionally substituted benzothiazoles, and optionally substituted pyridines; wherein the substituents on the substituted phenyl, substituted thiazoles, substituted benzothiazoles and substituted pyridines are selected from the group consisting of $C_1$–$C_4$ alkoxy, $C_1$–$C_4$ alkylthio, $C_1$–$C_6$ alkyl, halo and trifluoromethyl;

B, D, E and G are selected from the group consisting of nitrogen and carbon, with the proviso that one or more of B, D and E is nitrogen, and with the proviso that when G is nitrogen, the group XXVI is attached to the nitrogen of formula I at the 4 or 5 position of the pyrimidine ring (designated by a and b);

$R^{17}$ and $R^{18}$ are each independently selected from the group consisting of $C_4$–$C_{12}$ straight or branched alkyl, phenyl-$C_1$–$C_4$ alkyl, and $C_1$–$C_6$ alkylphenyl-$C_1$–$C_6$ alkyl;

with the proviso that when Q is $NR^{17}R^{18}$, $R^1$ is a group of the formula XXVI or XXIV, or a group of the formula XXVII wherein $R^7$, $R^8$ and $R^9$ are each methoxy.

The compounds of McCarthy et al. are disclosed as inhibitors of ACAT.

There are no known literature references disclosing the cyclic sulfide and ether compounds of this invention, their use as ACAT inhibitors, or their use to lower cholesterol or in the treatment of atherosclerosis. The invention of these compounds represents a potentially significant development in the area of treatment of atherosclerosis. The novel cyclic sulfide and ether compounds of the invention have improved potency and/or bioavailability.

SUMMARY OF THE INVENTION

This invention provides novel compounds of Formula I (described below) which are useful as antihypercholesterolemic and/or antiatherosclerotic agents. The compounds of the present invention inhibit the enzyme ACAT. The present invention also includes pharmaceutical compositions containing such compounds of Formula I, and methods of using such compounds as antihypercholesterolemic and/or antiatherosclerotic agents for the lowering of cholesterol levels and/or the treatment of atherosclerosis.

Also included in the present invention are pharmaceutical kits comprising one or more containers containing pharmaceutical dosage units comprising a compound of Formula I, for use in the treatment of atherosclerosis and/or for use in lowering cholesterol levels.

DETAILED DESCRIPTION OF THE INVENTION

This invention provides novel compounds of Formula I (described below) which are useful as antihypercholesterolemic and/or antiatherosclerotic agents. The compounds of the present invention inhibit the enzyme ACAT. The present invention also includes pharmaceutical compositions containing such compounds of Formula I, and methods of using such compounds as antihypercholesterolemic and/or antiatherosclerotic agents for the lowering of cholesterol levels and/or the treatment of atherosclerosis.

Also included in the present invention are pharmaceutical kits comprising one or more containers containing pharmaceutical dosage units comprising a compound of Formula I, for use in the treatment of atherosclerosis and/or for use in lowering cholesterol levels.

The present invention provides novel compounds of Formula I, processes for the preparation of such compounds, pharmaceutical compositions containing such compounds, and methods of using such compounds as therapeutic antihypercholesterolemic and/or antiatherosclerotic agents.

This invention provides compounds of Formula I:

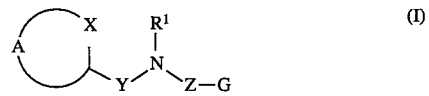

and stereoisomeric and pharmaceutically acceptable salt forms thereof wherein:

A is selected from

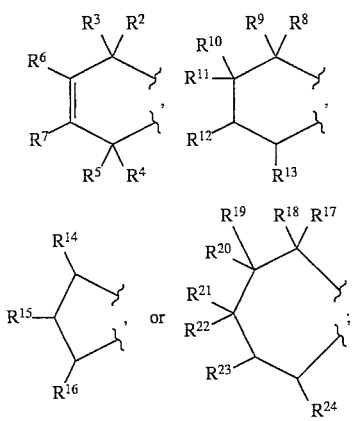

X is selected from: —O—, —S—, —S(=O)—, or —S(=O)$_2$—;

Y is selected from: —C(=O)—, —(CH$_2$)$_m$—, or —(CH$_2$)$_m$—NHC(=O)—;

m is an integer selected from 1–5;

Z is selected from a bond or —(CH$_2$)$_p$—;

p is an integer selected from 1–5;

G is selected from:
  phenyl substituted with 0–3 R$^{30}$, or
  naphthyl substituted with 0–3 R$^{30}$;

G may also be selected from a heterocylic group selected from:

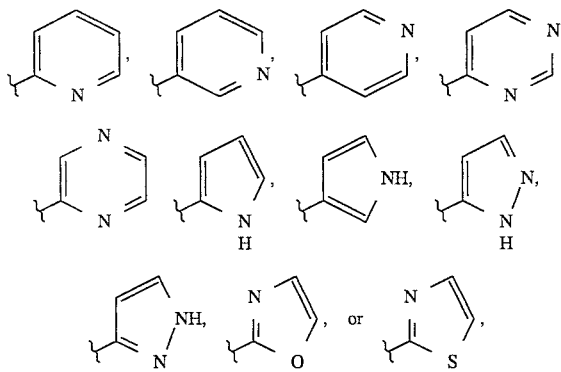

each such heterocyclic group being optionally fused to a benzene ring, and each such heterocyclic group and fused benzene ring being substituted with 0–3 R$^{30}$ or 0–3 phenyl groups, each phenyl being substituted with 0–3 R$^{30}$;

G may also be chosen from the following heterocyclic groups:

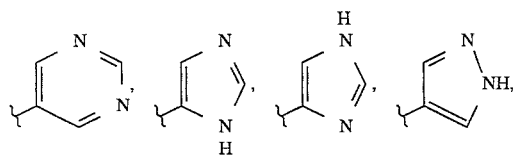

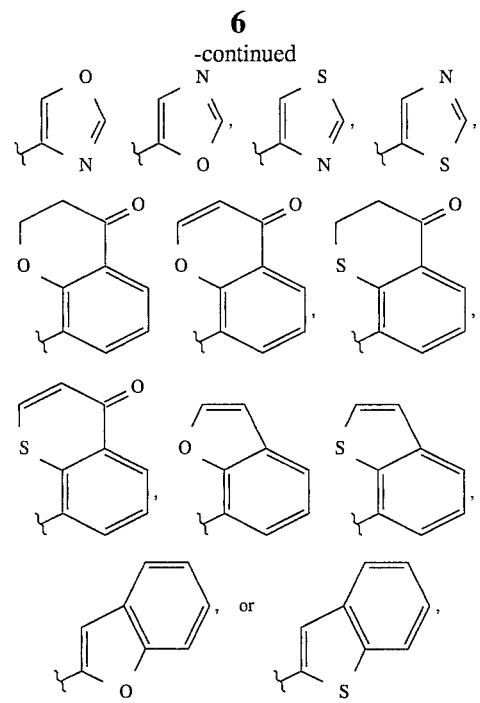

each such heterocyclic group being substituted with 0–3 R$^{30}$ or 0–3 phenyl groups, each phenyl being substituted with 0–3 R$^{30}$;

R$^1$ is selected from:
  H,
  C$_1$–C$_6$ alkyl,
  C$_3$–C$_8$ cycloalkyl,
  C$_4$–C$_9$ cycloalkylalkyl,
  benzyl substituted with 0–3 R$^{30}$, or
  phenyl substituted with 0–3 R$^{30}$;

R$^2$, R$^3$, R$^4$, R$^5$, R$^6$, R$^7$, R$^{17}$, R$^{18}$, R$^{19}$, R$^{20}$, R$^{21}$, R$^{22}$, R$^{23}$ and R$^{24}$ are independently selected from:
  H,
  C$_1$–C$_{13}$ alkyl,
  C$_3$–C$_8$ cycloalkyl,
  C$_3$–C$_8$ cycloalkyloxy,
  C$_4$–C$_9$ cycloalkylalkyl,
  C$_4$–C$_9$ cycloalkylalkyloxy,
  C$_4$–C$_{12}$ alkenyl,
  C$_4$–C$_{12}$ alkenyloxy,
  C$_4$–C$_{12}$ alkynyl,
  C$_4$–C$_{12}$ alkynyloxy,
  C$_1$–C$_{10}$ alkoxy,
  C$_2$–C$_{12}$ alkoxyalkyl,
  C$_2$–C$_{12}$ alkoxyalkyloxy,
  C$_3$–C$_{14}$ alkoxyalkoxyalkyl,
  C$_2$–C$_{10}$ alkylcarbonyloxy,
  C$_1$–C$_{10}$ alkylthio,
  C$_2$–C$_{10}$ alkylthioalkyl,
  C$_1$–C$_{10}$ haloalkyl,
  aryl-(C$_1$–C$_5$ alkyl)-substituted with 0–3 R$^{30}$,
  aryl-(C$_1$–C$_5$ alkyl)oxy substituted with 0– 3 R$^{30}$,
  aryl substituted with 0–3 R$^{30}$, or
  aryloxy substituted with 0–3 R$^{30}$;

R$^8$, R$^9$, R$^{10}$, R$^{11}$, R$^{12}$, R$^{13}$, R$^{14}$, R$^{15}$, R$^{16}$ are independently selected from:
  H,
  OH,
  C$_1$–C$_{13}$ alkyl,
  C$_3$–C$_8$ cycloalkyl,
  C$_3$–C$_8$ cycloalkyloxy, $C_4$–$C_9$ cycloalkylalkyl,
$C_4$–$C_9$ cycloalkylalkyloxy,
$C_4$–$C_{12}$ alkenyl,
$C_4$–$C_{12}$ alkenyloxy,
$C_4$–$C_{12}$ alkynyl,
$C_4$–$C_{12}$ alkynyloxy,
$C_1$–$C_{10}$ alkoxy,
$C_2$–$C_{12}$ alkoxyalkyl,
$C_2$–$C_{12}$ alkoxyalkyloxy,
$C_3$–$C_{14}$ alkoxyalkoxyalkyl,
$C_2$–$C_{10}$ alkylcarbonyloxy,
$C_1$–$C_{10}$ alkylthio,
$C_2$–$C_{10}$ alkylthioalkyl,
$C_1$–$C_{10}$ haloalkyl,
aryl-($C_1$–$C_5$ alkyl)-substituted with 0–3 $R^{30}$,
aryl-($C_1$–$C_5$ alkyl)oxy substituted with 0–3 $R^{30}$,
aryl substituted with 0–3 $R^{30}$, or
aryloxy substituted with 0–3 $R^{30}$;

$R^{12}$ can also be =O;

$R^3$ and $R^4$ can also be taken together to form a —$(CH_2)_q$— bridge;

q is an integer selected from 1–4;

$R^{12}$ and $R^{13}$ can alternatively be taken together to form a fused benzene ring, said fused benzene ring being substituted with 0–3 $R^{31}$;

$R^{23}$ and $R^{24}$ can alternatively be taken together to form a fused benzene ring, said fused benzene ring being substituted with 0–3 $R^{31}$;

$R^{30}$ is selected independently from: $C_1$–$C_6$ alkyl, $C_3$–$C_8$ cycloalkyl, $C_4$–$C_9$ cycloalkylalkyl, $C_1$–$C_4$ alkoxy, $C_1$–$C_4$ alkylthio, $C_2$–$C_8$ dialkylamino, halogen, $C_1$–$C_6$ haloalkyl, or nitro;

$R^{31}$ is selected independently from: $C_1$–$C_6$ alkyl, $C_3$–$C_8$ cycloalkyl, $C_4$–$C_9$ cycloalkylalkyl, $C_1$–$C_{10}$ alkoxy, $C_2$–$C_{12}$ alkoxyalkyl, $C_3$–$C_{14}$ alkoxyalkoxyalkyl, $C_2$–$C_{12}$ alkylcarbonyloxy, $C_1$–$C_{10}$ alkylthio, $C_2$–$C_{10}$ alkylthioalkyl, $C_2$–$C_8$ dialkylamino, halogen, $C_1$–$C_{10}$ haloalkyl, or nitro;

with the following provisos:

(1) when Y is —C(=O)— and A is

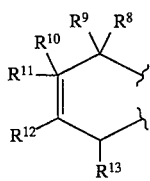

then one of the following conditions must hold:

a) at least two of the groups $R^8$, $R^9$, $R^{10}$, $R^{11}$, $R^{12}$, or $R^{13}$ are phenyl or substituted phenyl;

b) at least two of the groups $R^8$, $R^9$, $R^{10}$, $R^{11}$, $R^{12}$, or $R^{13}$ are $C_7$–$C_{12}$ alkyl;

c) at least two of the groups $R^8$, $R^9$, $R^{10}$, $R^{11}$, $R^{12}$, or $R^{13}$ are $C_7$–$C_{13}$ branched alkyl;

d) at least two of the groups $R^8$, $R^9$, $R^{10}$, $R^{11}$, $R^{12}$, or $R^{13}$ are $C_7$–$C_{12}$ alkenyl;

e) the groups $R^{12}$ and $R^{13}$ are taken together to form a fused benzene ring, said benzene ring being substituted with at least one group chosen from among $C_1$–$C_{10}$ alkoxy, $C_2$–$C_{12}$ alkoxyalkyl, $C_3$–$C_{14}$ alkoxyalkoxyalkyl, $C_2$–$C_{10}$ alkylcarbonyloxy, $C_1$–$C_{10}$ alkylthio, $C_2$–$C_{10}$ alkylthioalkyl, or $C_1$–$C_{10}$ haloalkyl;

f) none of the groups $R^8$, $R^9$, $R^{10}$, $R^{11}$, $R^{12}$, or $R^{13}$ are chosen as $C_1$–$C_{13}$ alkyl, $C_4$–$C_9$ cycloalkylalkyl, $C_4$–$C_{12}$ alkenyl, phenyl, or substituted phenyl, but at least one of the groups $R^8$, $R^9$, $R^{10}$, $R^{11}$, $R^{12}$, or $R^{13}$ must not be H;

g) when $R^8$ is hydroxy, then $R^9$ is hydrogen, likewise, when $R^{10}$ is hydroxy, then $R^{11}$ is hydrogen;

(2) when Y is —C(=O)— and A is

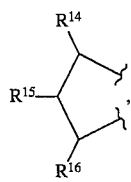

then one of the following conditions must hold:

a) at least two of the groups $R^{14}$, $R^{15}$ or $R^{16}$ be phenyl or substituted phenyl;

b) at least two of the groups $R^{14}$, $R^{15}$ or $R^{16}$ be chosen as $C_7$–$C_{12}$ alkyl;

c) at least two of the groups $R^{15}$, $R^{16}$ or $R^{16}$ be chosen as $C_7$–$C_{13}$ branched alkyl;

d) at least two of the groups $R^{14}$, $R^{15}$ or $R^{16}$ be chosen as $C_7$–$C_{12}$ alkenyl;

e) none of the groups $R^{14}$, $R^{15}$ or $R^{16}$ are chosen from $C_1$–$C_{13}$ alkyl, $C_3$–$C_8$ cycloalkyl, $C_4$–$C_9$ cycloalkylalkyl, $C_4$–$C_{12}$ alkenyl, phenyl, or substituted phenyl, but at least one of the groups $R^{14}$, $R^{15}$ or $R^{16}$ must not be H;

(3) when Y is —C(=O)— and A is

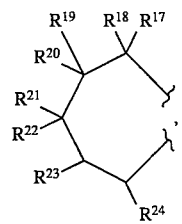

then one of the following conditions must hold:

a) at least two of the groups $R^{17}$, $R^{18}$, $R^{19}$, $R^{20}$, $R^{21}$, $R^{22}$, $R^{23}$ or $R^{24}$ be phenyl or substituted phenyl;

b) at least two of the groups $R^{17}$, $R^{18}$, $R^{19}$, $R^{20}$, $R^{21}$, $R^{22}$, $R^{23}$ or $R^{24}$ be chosen as $C_7$–$C_{12}$ alkyl;

c) at least two of the groups $R^{17}$, $R^{18}$, $R^{19}$, $R^{20}$, $R^{21}$, $R^{22}$, $R^{23}$ or $R^{24}$ be chosen as $C_7$–$C_{13}$ branched alkyl;

d) at least two of the groups $R^{17}$, $R^{18}$, $R^{19}$, $R^{20}$, $R^{21}$, $R^{22}$, $R^{23}$ or $R^{24}$ be chosen as $C_7$–$C_{12}$ alkenyl;

e) the groups $R^{23}$ and $R^{24}$ are taken together to form a fused benzene ring, said benzene ring being substituted with at least one group chosen from among $C_1$–$C_{10}$ alkoxy, $C_2$–$C_{12}$ alkoxyalkyl, $C_3$–$C_{14}$ alkoxyalkoxyalkyl, $C_2$–$C_{10}$ alkylcarbonyloxy, $C_1$–$C_{10}$ alkylthio, $C_2$–$C_{10}$ alkylthioalkyl, or $C_1$–$C_{10}$ haloalkyl;

f) none of the groups $R^{17}$, $R^{18}$, $R^{19}$, $R^{20}$, $R^{21}$, $R^{22}$, $R^{23}$ or $R^{24}$ are chosen as $C_1$–$C_{13}$ alkyl, $C_3$–$C_8$ cycloalkyl, $C_4$–$C_9$ cycloalkylalkyl, $C_4$–$C_{12}$ alkenyl, phenyl, or substituted phenyl, but at least one of the groups $R^{17}$, $R^{18}$, $R^{19}$, $R^{20}$, $R^{21}$, $R^{22}$, $R^{23}$ or $R^{24}$ must not be H.

Preferred compounds of the present invention are those compounds of Formula I, and stereoisomeric and pharmaceutically acceptable salt forms thereof, wherein:

A is selected from:

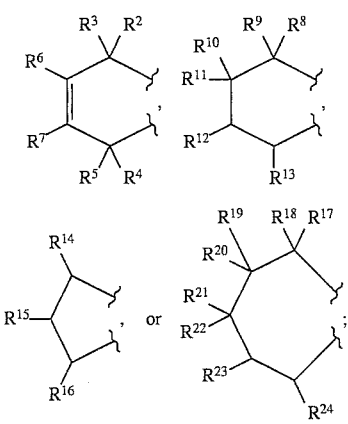

X is selected from O, S, S(=O), or S(=O)$_2$;
Y is C(=O);
Z is a bond;
G is selected from:
phenyl substituted with 1–3 R$^{30}$, or a heterocycle selected from:

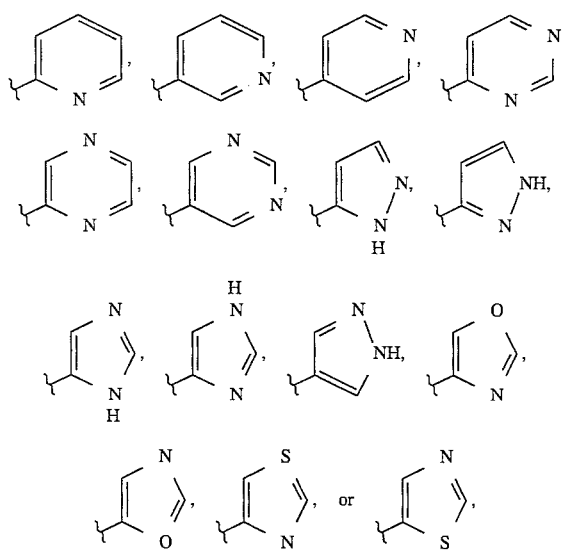

each such heterocyclic group being substituted with 0–3 R$^{30}$ or 0–3 phenyl groups, each phenyl being substituted with 0–3 R$^{30}$;

R$^1$ is selected from H, C$_1$–C$_4$ alkyl, C$_3$–C$_6$ branched alkyl, or C$_3$–C$_8$ cycloalkyl;

R$^2$, R$^3$, R$^4$, R$^5$, R$^6$, R$^7$, R$^{17}$, R$^{18}$, R$^{19}$, R$^{20}$, R$^{21}$, R$^{22}$, R$^{23}$ and R$^{24}$ are independently selected from:
H,
C$_1$–C$_{10}$ straight chain alkyl,
C$_3$–C$_6$ branched alkyl
C$_3$–C$_8$ cycloalkyl,
C$_1$–C$_{10}$ alkoxy,
C$_2$–C$_{10}$ alkoxyalkyl,
C$_2$–C$_{10}$ alkoxyalkyloxy,
benzyl substituted with 0–3 R$^{30}$,
benzyloxy substituted with 0–3 R$^{30}$,
phenyl substituted with 0–3 R$^{30}$, or
phenyloxy substituted with 0–3 R$^{30}$;

R$^8$, R$^9$, R$^{10}$, R$^{11}$, R$^{12}$, R$^{13}$, R$^{14}$, R$^{15}$, and R$^{16}$ are independently selected from:
H,
OH,
C$_1$–C$_{10}$ straight chain alkyl,
C$_3$–C$_6$ branched alkyl
C$_3$–C$_8$ cycloalkyl,
C$_1$–C$_{10}$ alkoxy,
C$_2$–C$_{10}$ alkoxyalkyl,
C$_2$–C$_{10}$ alkoxyalkyloxy,
benzyl substituted with 0–3 R$^{30}$,
benzyloxy substituted with 0–3 R$^{30}$,
phenyl substituted with 0–3 R$^{30}$, or
phenyloxy substituted with 0–3 R$^{30}$;

R$^{12}$ can also be =O;

R$^3$ and R$^4$ can also be taken together to form —CH$_2$— or —CH$_2$CH$_2$—;

R$^{12}$ and R$^{13}$ can alternatively be taken together to form a fused benzene ring, said fused benzene ring being substituted with 0–3 R$^{31}$;

R$^{23}$ and R$^{24}$ can alternatively be taken together to form a fused benzene ring, said fused benzene ring being substituted with 0–3 R$^{31}$;

R$^{30}$ is selected independently from: C$_1$–C$_6$ alkyl, C$_3$–C$_8$ cycloalkyl, C$_1$–C$_4$ alkoxy, C$_1$–C$_4$ alkylthio, C$_2$–C$_8$ dialkylamino;

R$^{31}$ is selected independently from: C$_1$–C$_6$ alkyl, C$_1$–C$_{10}$ alkoxy, C$_1$–C$_4$ alkylthio, or C$_2$–C$_8$ dialkylamino;

with the following provisos:
(1) when A is

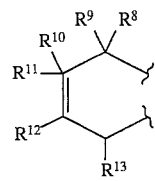

then one of the following conditions must hold:
a) at least two of the groups R$^8$, R$^9$, R$^{10}$, R$^{11}$, R$^{12}$, or R$^{13}$ are phenyl or substituted phenyl;
b) at least two of the groups R$^8$, R$^9$, R$^{10}$, R$^{11}$, R$^{12}$, or R$^{13}$ are C$_7$–C$_{10}$ alkyl;
c) the groups R$^{12}$ and R$^{13}$ are taken together to form a fused benzene ring, said benzene ring being substituted with at least one group chosen from among C$_1$–C$_{10}$ alkoxy, or C$_1$–C$_4$ alkylthio;
d) none of the groups R$^8$, R$^9$, R$^{10}$, R$^{11}$, R$^{12}$, or R$^{13}$ are chosen as C$_1$–C$_{10}$ straight chain alkyl, C$_3$–C$_6$ branched alkyl, phenyl, or substituted phenyl, but at least one of the groups R$^8$, R$^9$, R$^{10}$, R$^{11}$, R$^{12}$, or R$^{13}$ must not be H;
e) when R$^8$ is hydroxy, then R$^9$ is hydrogen, likewise, when R$^{10}$ is hydroxy, then R$^{11}$ is hydrogen;

(2) when Y is —C(=O)— and A is

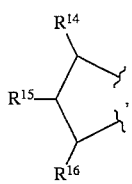

then one of the following conditions must hold:
a) at least two of the groups R$^{14}$, R$^{15}$ or R$^{16}$ be phenyl or substituted phenyl;
b) at least two of the groups R$^{14}$, R$^{15}$ or R$^{16}$ be chosen as C$_7$–C$_{12}$ alkyl;
c) at least two of the groups R$^{15}$, R$^{16}$ or R$^{16}$ be chosen as C$_7$–C$_{13}$ branched alkyl;

d) at least two of the groups $R^{14}$, $R^{15}$ or $R^{16}$ be chosen as $C_7$–$C_{12}$ alkenyl;

e) none of the groups $R^{14}$, $R^{15}$ or $R^{16}$ are chosen from $C_1$–$C_{13}$ alkyl, $C_3$–$C_8$ cycloalkyl, $C_4$–$C_9$ cycloalkylalkyl, $C_4$–$C_{12}$ alkenyl, phenyl, or substituted phenyl, but at least one of the groups $R^{14}$, $R^{15}$ or $R^{16}$ must not be H;

(3) when Y is —C(=O)— and A is

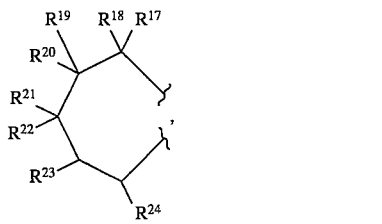

then one of the following conditions must hold:

a) at least two of the groups $R^{17}$, $R^{18}$, $R^{19}$, $R^{20}$, $R^{21}$, $R^{22}$, $R^{23}$ or $R^{24}$ be phenyl or substituted phenyl;

b) at least two of the groups $R^{17}$, $R^{18}$, $R^{19}$, $R^{20}$, $R^{21}$, $R^{22}$, $R^{23}$ or $R^{24}$ be chosen as $C_7$–$C_{10}$ straight chain alkyl;

c) the groups $R^{23}$ and $R^{24}$ are taken together to form a fused benzene ring, said benzene ring being substituted with at least one group chosen from among $C_1$–$C_{10}$ alkoxy, or $C_1$–$C_4$ alkylthio;

d) none of the groups $R^{17}$, $R^{18}$, $R^{19}$, $R^{20}$, $R^{21}$, $R^{22}$, $R^{23}$ or $R^{24}$ are chosen as $C_1$–$C_{10}$ straight chain alkyl, $C_3$–$C_6$ branched alkyl, $C_3$–$C_8$ cycloalkyl, phenyl, or substituted phenyl, but at least one of the groups $R^{17}$, $R^{18}$, $R^{19}$, $R^{20}$, $R^{21}$, $R^{22}$, $R^{23}$ or $R^{24}$ must not be H.

[3] More preferred compounds of the present invention are those compounds of Formula I, and stereoisomeric and pharmaceutically acceptable salt forms thereof, wherein:

A is selected from:

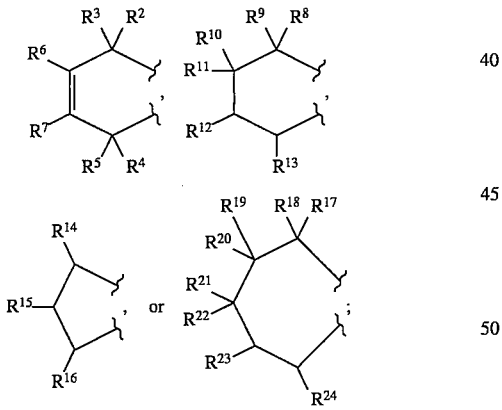

X is O or S;
Y is C(=O);
Z is a bond;
G is selected from:
  phenyl substituted with 1–3 $R^{30}$, or
  a heterocyclic group selected from:

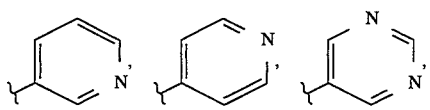

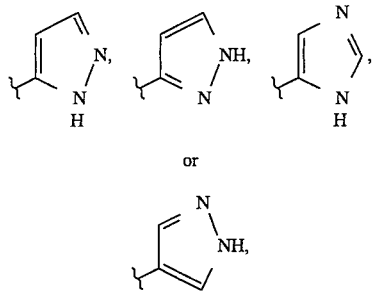

or each such heterocyclic group being substituted with 0–3 $R^{30}$ or 0–3 phenyl groups, each phenyl being substituted with 0–3 $R^{30}$;

$R^1$ is H;

$R^2$, $R^3$, $R^4$, $R^5$, $R^6$, $R^7$, $R^{17}$, $R^{18}$, $R^{19}$, $R^{20}$, $R^{21}$, $R^{22}$, $R^{23}$ and $R^{24}$ are independently selected from:
H,
$C_1$–$C_{10}$ straight chain alkyl,
$C_3$–$C_6$ branched alkyl
$C_3$–$C_8$ cycloalkyl,
$C_1$–$C_{10}$ alkoxy,
$C_2$–$C_{10}$ alkoxyalkyl,
$C_2$–$C_{10}$ alkoxyalkyloxy,
benzyl substituted with 0–3 $R^{30}$,
benzyloxy substituted with 0–3 $R^{30}$,
phenyl substituted with 0–3 $R^{30}$, or
phenyloxy substituted with 0–3 $R^{30}$;

$R^8$, $R^9$, $R^{10}$, $R^{11}$, $R^{12}$, $R^{13}$, $R^{14}$, $R^{15}$, $R^{16}$ are independently selected from:
H,
OH,
$C_1$–$C_{10}$ straight chain alkyl,
$C_3$–$C_6$ branched alkyl
$C_3$–$C_8$ cycloalkyl,
$C_1$–$C_{10}$ alkoxy,
$C_2$–$C_{10}$ alkoxyalkyl,
$C_2$–$C_{10}$ alkoxyalkyloxy,
benzyl substituted with 0–3 $R^{30}$,
benzyloxy substituted with 0–3 $R^{30}$,
phenyl substituted with 0–3 $R^{30}$, or
phenyloxy substituted with 0–3 $R^{30}$;

$R^{12}$ can also be =O;

$R^{12}$ and $R^{13}$ can alternatively be taken together to form a fused benzene ring, said fused benzene ring being substituted with 0–3 $R^{31}$;

$R^{23}$ and $R^{24}$ can alternatively be taken together to form a fused benzene ring, said fused benzene ring being substituted with 0–3 $R^{31}$;

$R^{30}$ is selected independently from: $C_1$–$C_4$ straight chain alkyl, $C_3$–$C_6$ branched alkyl, $C_3$–$C_8$ cycloalkyl, $C_1$–$C_4$ alkoxy, $C_1$–$C_4$ alkylthio, $C_2$–$C_8$ dialkylamino;

$R^{31}$ is selected independently from: $C_1$–$C_4$ straight chain alkyl, $C_3$–$C_6$ branched alkyl, $C_1$–$C_{10}$ alkoxy, $C_1$–$C_4$ alkylthio;

with the following provisos:

(1) when A is

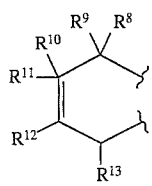

then one of the following conditions must hold:
  a) at least two of the groups $R^8$, $R^9$, $R^{10}$, $R^{11}$, $R^{12}$, or $R^{13}$ are $C_7$–$C_{10}$ alkyl;
  b) the groups $R^{12}$ and $R^{13}$ are taken together to form a fused benzene ring, said benzene ring being substituted with at least one group chosen from among $C_1$–$C_{10}$ alkoxy, or $C_1$–$C_4$ alkylthio;
  c) none of the groups $R^8$, $R^9$, $R^{10}$, $R^{11}$, $R^{12}$, $R^{13}$ are chosen as $C_1$–$C_4$ straight chain alkyl, $C_3$–$C_6$ branched alkyl, but at least one of the groups $R^8$, $R^9$, $R^{10}$, $R^{11}$, $R^{12}$, $R^{13}$ must not be H;
  d) when $R^8$ is hydroxy, then $R^9$ is hydrogen, likewise, when $R^{10}$ is hydroxy, then $R^{11}$ is hydrogen;
(2) when Y is —C(=O)— and A is

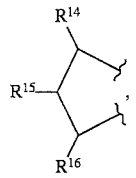

then one of the following conditions must hold:
  a) at least two of the groups $R^{14}$, $R^{15}$ or $R^{16}$ be phenyl or substituted phenyl;
  b) at least two of the groups $R^{14}$, $R^{15}$ or $R^{16}$ be chosen as $C_7$–$C_{12}$ alkyl;
  c) at least two of the groups $R^{15}$, $R^{16}$ or $R^{16}$ be chosen as $C_7$–$C_{13}$ branched alkyl;
  d) at least two of the groups $R^{14}$, $R^{15}$ or $R^{16}$ be chosen as $C_7$–$C_{12}$ alkenyl;
  e) none of the groups $R^{14}$, $R^{15}$ or $R^{16}$ are chosen from $C_1$–$C_{13}$ alkyl, $C_3$–$C_8$ cycloalkyl, $C_4$–$C_9$ cycloalkylalkyl, $C_4$–$C_{12}$ alkenyl, phenyl, or substituted phenyl, but at least one of the groups $R^{14}$, $R^{15}$ or $R^{16}$ must not be H;
(3) when Y is —C(=O)— and A is

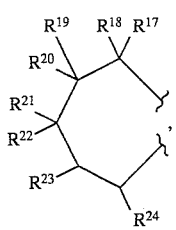

then one of the following conditions must hold:
  a) at least two of the groups $R^{17}$, $R^{18}$, $R^{19}$, $R^{20}$, $R^{21}$, $R^{22}$, $R^{23}$ or $R^{24}$ be chosen as $C_7$–$C_{10}$ straight chain alkyl;
  b) the groups $R^{23}$ and $R^{24}$ are taken together to form a fused benzene ring, said benzene ring being substituted with at least one group chosen from among $C_1$–$C_{10}$ alkoxy, or $C_1$–$C_4$ alkylthio;
  c) none of the groups $R^{17}$, $R^{18}$, $R^{19}$, $R^{20}$, $R^{21}$, $R^{22}$, $R^{23}$ or $R^{24}$ are chosen as $C_1$–$C_{10}$ straight chain alkyl, $C_3$–$C_6$ branched alkyl, $C_3$–$C_8$ cycloalkyl, but at least one of the groups $R^{17}$, $R^{18}$, $R^{19}$, $R^{20}$, $R^{21}$, $R^{22}$, $R^{23}$ or $R^{24}$ must not be H.

[4] Also, more preferred compounds of the present invention are those compounds of Formula I, and stereoisomeric and pharmaceutically acceptable salt forms thereof, wherein:

A is:

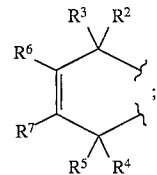

X is S;

Y is C(=O);

Z is a bond;

G is selected from:
  phenyl substituted with 1–3 $R^{30}$, or
  a heterocyclic group selected from:

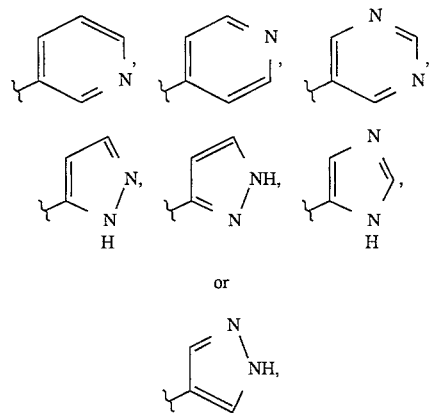

each such heterocyclic group being substituted with 0–3 $R^{30}$ or 0–3 phenyl groups, each phenyl being substituted with 0–3 $R^{30}$;

$R^1$ is H;

$R^3$ and $R^4$ are H;

$R^2$, $R^5$, $R^6$, and $R^7$ are independently selected from:
  H,
  $C_1$–$C_{10}$ straight chain alkyl,
  $C_3$–$C_{10}$ branched alkyl
  $C_3$–$C_{10}$ cycloalkyl,
  $C_3$–$C_{14}$ cycloalkylalkyl,
  $C_1$–$C_{10}$ alkoxy,
  $C_2$–$C_{10}$ alkoxyalkyl;

$R^{30}$ is selected independently from: $C_1$–$C_{10}$ straight chain alkyl, $C_3$–$C_{10}$ branched alkyl, $C_3$–$C_{10}$ cycloalkyl, $C_1$–$C_4$ alkoxy, $C_1$–$C_4$ alkylthio, $C_2$–$C_8$ dialkylamino, halogen, nitro

[5] Also, more preferred compounds of the present invention are those compounds of Formula I, and stereoisomeric and pharmaceutically acceptable salt forms thereof, wherein:

A is:

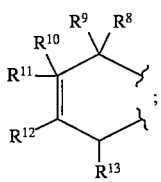

X is O or S;
Y is C(=O);
Z is a bond;
G is selected from:
  phenyl substituted with 1–3 $R^{30}$, or
  a heterocyclic group selected from:

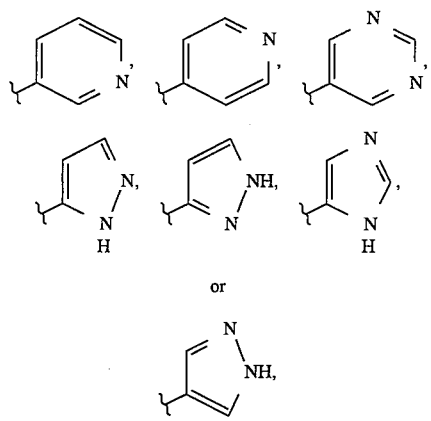

each such heterocyclic group being substituted with 0–3 $R^{30}$ or 0–3 phenyl groups, each phenyl being substituted with 0–3 $R^{30}$;

$R^1$ is H;

$R^8$ and $R^{11}$ are H;

$R^9$, $R^{10}$, $R^{12}$ and $R^{13}$ are independently selected from:
  H,
  OH
  $C_1$–$C_{10}$ straight chain alkyl,
  $C_3$–$C_6$ branched alkyl
  $C_3$–$C_8$ cycloalkyl,
  $C_1$–$C_{10}$ alkoxy,
  $C_2$–$C_{10}$ alkoxyalkyl,
  $C_2$–$C_{10}$ alkoxyalkyloxy,
  benzyl substituted with 0–3 $R^{30}$,
  benzyloxy substituted with 0–3 $R^{30}$,
  phenyl substituted with 0–3 $R^{30}$, or
  phenyloxy substituted with 0–3 $R^{30}$;

$R^{12}$ can also be =O;

$R^{12}$ and $R^{13}$ can alternatively be taken together to form a fused benzene ring, said fused benzene ring being substituted with 0–3 $R^{31}$;

$R^{30}$ is selected independently from: $C_1$–$C_4$ straight chain alkyl, $C_3$–$C_6$ branched alkyl, $C_3$–$C_8$ cycloalkyl, $C_1$–$C_4$ alkoxy, $C_1$–$C_4$ alkylthio, $C_2$–$C_8$ dialkylamino;

$R^{31}$ is selected independently from: $C_1$–$C_4$ straight chain alkyl, $C_3$–$C_6$ branched alkyl, $C_1$–$C_{10}$ alkoxy, $C_1$–$C_4$ alkylthio;

with the following proviso that one of the following conditions must hold:
  a) at least two of the groups $R^9$, $R^{10}$, $R^{12}$, or $R^{13}$ are $C_7$–$C_{10}$ alkyl;
  b) the groups $R^{12}$ and $R^{13}$ are taken together to form a fused benzene ring, said benzene ring being substituted with at least one group chosen from among $C_1$–$C_{10}$ alkoxy or $C_1$–$C_4$ alkylthio;
  c) none of the groups $R^9$, $R^{10}$, $R^{12}$, or $R^{13}$ are chosen as $C_1$–$C_4$ straight chain alkyl, $C_3$–$C_6$ branched alkyl, but at least one of the groups $R^9$, $R^{10}$, $R^{12}$, or $R^{13}$ must not be H.
  d) when $R^8$ is hydroxy, then $R^9$ is hydrogen, likewise, when $R^{10}$ is hydroxy, then $R^{11}$ is hydrogen;

[6] Also, more preferred compounds of the present invention are those compounds of Formula I, and stereoisomeric and pharmaceutically acceptable salt forms thereof, wherein:

A is:

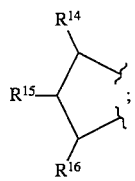

X is O or S;
Y is C(=O);
Z is a bond;
G is selected from:
  phenyl substituted with 1–3 $R^{30}$, or
  a heterocyclic group selected from:

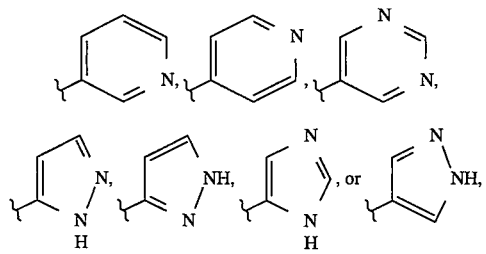

each such heterocyclic group being substituted with 0–3 $R^{30}$ or 0–3 phenyl groups, each phenyl being substituted with 0–3 $R^{30}$;

$R^1$ is H;

$R^8$ and $R^{11}$ are H;

$R^{14}$, $R^{15}$, and $R^{16}$ are independently selected from:
  H,
  OH
  $C_1$–$C_{10}$ straight chain alkyl,
  $C_3$–$C_6$ branched alkyl
  $C_3$–$C_8$ cycloalkyl,
  $C_1$–$C_{10}$ alkoxy,
  $C_2$–$C_{10}$ alkoxyalkyl,
  $C_2$–$C_{10}$ alkoxyalkyloxy,
  benzyl substituted with 0–3 $R^{30}$,
  benzyloxy substituted with 0–3 $R^{30}$,
  phenyl substituted with 0–3 $R^{30}$, or
  phenyloxy substituted with 0–3 $R^{30}$;

$R^{12}$ can also be =O;

$R^{12}$ and $R^{13}$ can alternatively be taken together to form a fused benzene ring, said fused benzene ring being substituted with 0–3 $R^{31}$;

$R^{30}$ is selected independently from: $C_1$–$C_4$ straight chain alkyl, $C_3$–$C_6$ branched alkyl, $C_3$–$C_8$ cycloalkyl, $C_1$–$C_4$ alkoxy, $C_1$–$C_4$ alkylthio, $C_2$–$C_8$ dialkylamino;

$R^{31}$ is selected independently from: $C_1$–$C_4$ straight chain alkyl, $C_3$–$C_6$ branched alkyl, $C_1$–$C_{10}$ alkoxy, $C_1$–$C_4$ alkylthio;

with the following proviso that one of the following conditions must hold:

a) at least two of the groups $R^{14}$, $R^{15}$, or $R^{16}$ are $C_7$–$C_{10}$ alkyl;

b) the groups $R^{15}$ and $R^{16}$ are taken together to form a fused benzene ring, said benzene ring being substituted with at least one group chosen from among $C_1$–$C_{10}$ alkoxy or $C_1$–$C_4$ alkylthio;

c) none of the groups $R^{14}$, $R^{15}$, or $R^{16}$ are chosen as $C_1$–$C_4$ straight chain alkyl, $C_3$–$C_6$ branched alkyl, but at least one of the groups $R^{14}$, $R^{15}$, or $R^{16}$ must not be H.

[7] Also, more preferred compounds of the present invention are those compounds of Formula I, and stereoisomeric and pharmaceutically acceptable salt forms thereof, wherein:

A is:

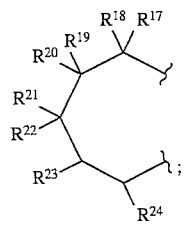

X is S;
Y is C(=O);
Z is a bond;
G is selected from:
  phenyl substituted with 1–3 $R^{30}$, or
  a heterocyclic group selected from:

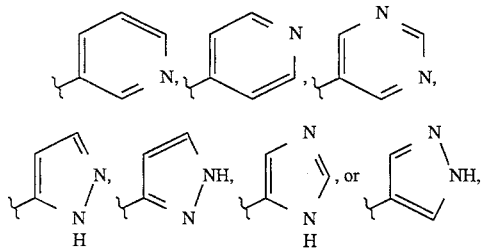

each such heterocyclic group being substituted with 0–3 $R^{30}$ or 0–3 phenyl groups, each phenyl being substituted with 0–3 $R^{30}$;

$R^1$ is H;

$R^{17}$, $R^{19}$, $R^{21}$ are H;

$R^{18}$, $R^{20}$, $R^{22}$, $R^{23}$ and $R^{24}$ are independently selected from:
  H,
  $C_1$–$C_{10}$ straight chain alkyl,
  $C_3$–$C_6$ branched alkyl
  $C_3$–$C_8$ cycloalkyl,
  $C_1$–$C_{10}$ alkoxy,
  $C_2$–$C_{10}$ alkoxyalkyl,
  $C_2$–$C_{10}$ alkoxyalkyloxy,
  benzyl substituted with 0–3 $R^{30}$,
  benzyloxy substituted with 0–3 $R^{30}$, or
  phenyl substituted with 0–3 $R^{30}$,
  phenyloxy substituted with 0–3 $R^{30}$;

$R^{23}$ and $R^{24}$ can alternatively be taken together to form a fused benzene ring, said fused benzene ring being substituted with 0–3 $R^{31}$;

$R^{30}$ is selected independently from: $C_1$–$C_4$ straight chain alkyl, $C_3$–$C_6$ branched alkyl, $C_3$–$C_8$ cycloalkyl, $C_1$–$C_4$ alkoxy, $C_1$–$C_4$ alkylthio, $C_2$–$C_8$ dialkylamino;

$R^{31}$ is selected independently from: $C_1$–$C_4$ straight chain alkyl, $C_3$–$C_6$ branched alkyl, $C_1$–$C_{10}$ alkoxy, $C_1$–$C_4$ alkylthio;

with the provisos that one of the following conditions must hold:

a) at least two of the groups $R^{18}$, $R^{20}$, $R^{22}$, or $R^{24}$ be chosen as $C_7$–$C_{10}$ straight chain alkyl;

b) the groups $R^{23}$ and $R^{24}$ are taken together to form a fused benzene ring, said benzene ring being substituted with at least one group chosen from among $C_1$–$C_{10}$ alkoxy, or $C_1$–$C_4$ alkylthio;

c) none of the groups $R^{18}$, $R^{20}$, $R^{22}$, or $R^{24}$ are chosen as $C_1$–$C_{10}$ straight chain alkyl, $C_3$–$C_6$ branched alkyl, $C_3$–$C_8$ cycloalkyl, but at least one of the groups $R^{18}$, $R^{20}$, $R^{22}$, or $R^{24}$ must not be H.

[8] Further preferred compounds of the present invention are those compounds of Formula I, and stereoisomeric and pharmaceutically acceptable salt forms thereof, wherein:

A is:

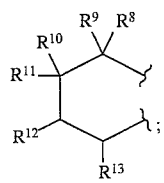

X is O or S;
Y is C(=O);
Z is a bond;
G is selected from:
  phenyl substituted with 1–3 $R^{30}$, or
  a heterocyclic group selected from:

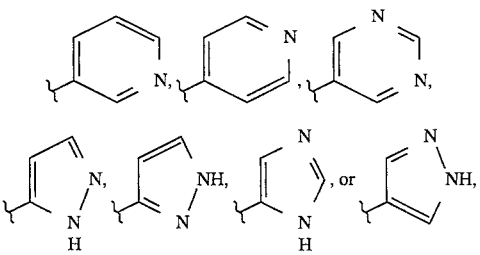

each such heterocyclic group being substituted with 0–3 $R^{30}$ or 0–3 phenyl groups, each phenyl being substituted with 0–3 $R^{30}$;

$R^1$ is H;

$R^8$, $R^{10}$, $R^{12}$, and $R^{13}$ are independently selected from:
  H,
  OH,
  $C_1$–$C_{10}$ alkoxy,
  $C_2$–$C_{10}$ alkoxyalkyloxy,
  benzyloxy, or
  phenoxy $R^{30}$ is selected independently from: $C_1$–$C_4$ straight chain alkyl, $C_3$–$C_6$ branched alkyl, $C_3$–$C_8$ cycloalkyl, $C_1$–$C_4$ alkoxy, $C_1$–$C_4$ alkylthio, $C_2$–$C_8$ dialkylamino;

with the proviso that at least one of $R^8$, $R^{10}$, $R^{12}$, and $R^{13}$ are not hydrogen, and that when $R^8$ is hydroxy, then $R^9$ is hydrogen, likewise, when $R^{10}$ is hydroxy, then $R^{11}$ is hydrogen.

[9] Further preferred compounds of the present invention are those compounds of Formula I, and stereoisomeric and pharmaceutically acceptable salt forms thereof, wherein:

A is:

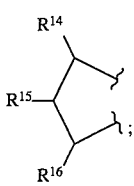

X is O or S;
Y is C(=O);
Z is a bond;
G is selected from:
   phenyl substituted with 1–3 $R^{30}$, or
   a heterocyclic group selected from:

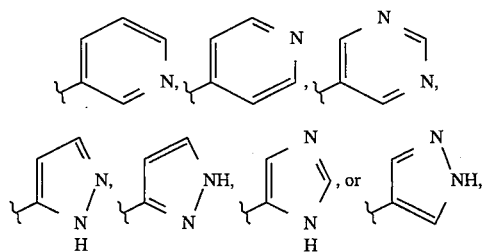

each such heterocyclic group being substituted with 0–3 $R^{30}$ or 0–3 phenyl groups, each phenyl being substituted with 0–3 $R^{30}$;
$R^1$ is H;
$R^{14}$, $R^{15}$, and $R^{16}$ are independently selected from:
   H,
   OH,
   $C_1$–$C_{10}$ alkoxy,
   $C_2$–$C_{10}$ alkoxyalkyloxy,
   benzyloxy, or
   phenoxy
$R^{30}$ is selected independently from: $C_1$–$C_4$ straight chain alkyl, $C_3$–$C_6$ branched alkyl, $C_3$–$C_8$ cycloalkyl, $C_1$–$C_4$ alkoxy, $C_1$–$C_4$ alkylthio, $C_2$–$C_8$ dialkylamino;
with the proviso that at least one of $R^{14}$, $R^{15}$, and $R^{16}$ are not hydrogen.

[10] Further preferred compounds of the present invention are those compounds of Formula I, and stereoisomeric and pharmaceutically acceptable salt forms thereof, wherein:

A is:

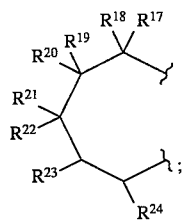

X is S;
Y is C(=O);
Z is a bond;
G is selected from:
   phenyl substituted with 1–3 $R^{30}$, or
   a heterocyclic group selected from:

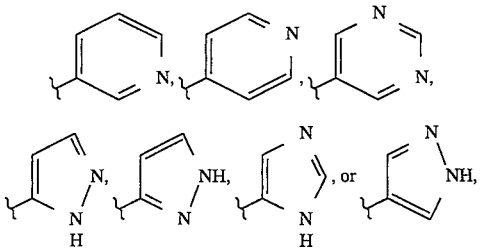

each such heterocyclic group being substituted with 0–3 $R^{30}$ or 0–3 phenyl groups, each phenyl being substituted with 0–3 $R^{30}$;
$R^1$ is H;
$R^{17}$, $R^{19}$, $R^{21}$ are H;
$R^{18}$, $R^{20}$, and $R^{22}$ are independently selected from:
   H,
   $C_1$–$C_{10}$ straight chain alkyl,
   $C_3$–$C_6$ branched alkyl
   $C_3$–$C_8$ cycloalkyl,
   $C_1$–$C_{10}$ alkoxy,
   $C_2$–$C_{10}$ alkoxyalkyl,
   $C_2$–$C_{10}$ alkoxyalkyloxy,
   benzyl substituted with 0–3 $R^{30}$,
   benzyloxy substituted with 0–3 $R^{30}$, or
   phenyl substituted with 0–3 $R^{30}$,
   phenyloxy substituted with 0–3 $R^{30}$;
$R^{23}$ and $R^{24}$ are taken together to form a fused benzene ring, said fused benzene ring being substituted with 1–3 $R^{31}$;
$R^{30}$ is selected independently from: $C_1$–$C_4$ straight chain alkyl, $C_3$–$C_6$ branched alkyl, $C_3$–$C_8$ cycloalkyl, $C_1$–$C_4$ alkoxy, $C_1$–$C_4$ alkylthio, $C_2$–$C_8$ dialkylamino;
$R^{31}$ is selected independently from: $C_1$–$C_4$ straight chain alkyl, $C_3$–$C_6$ branched alkyl, $C_1$–$C_{10}$ alkoxy, $C_1$–$C_4$ alkylthio;
with the proviso that at least one $R^{31}$ is $C_1$–$C_{10}$ alkoxy or $C_1$–$C_4$ alkylthio.

[11] Specifically preferred compounds of the invention are compounds, or pharmaceutically acceptable salt or prodrug forms thereof, selected from:
N-[2,4-bis(methylthio)-6-methylpyridin-3-yl]-4,5-dihydro-3,6-dimethyl-2H-thiopyran-2-carboxamide;
N-[2,4-bis(methylthio)-6-methylpyridin-3-yl]-4,5-dihydro-3,6-dipropyl-2H-thiopyran-2-carboxamide;
N-[2,4-bis(methylthio)-6-methylpyridin-3-yl]-3,6-dibutyl-4,5-dihydro-2H-thiopyran-2-carboxamide;
N-[2,4-bis(methylthio)-6-methylpyridin-3-yl]-4,5-dihydro-3,6-dipentyl-2H-thiopyran-2-carboxamide;
N-[2,4-bis(methylthio)-6-methylpyridin-3-yl]-3,6-dihexyl-4,5-dihydro-2H-thiopyran-2-carboxamide;
N-[2,4-bis(methylthio)-6-methylpyridin-3-yl]-3,6-diheptyl-4,5-dihydro-2H-thiopyran-2-carboxamide;
N-[2,4-bis(methylthio)-6-methylpyridin-3-yl]-4,5-dihydro-3,6-dioctyl-2H-thiopyran-2-carboxamide;
N-[2,4-bis(methylthio)-6-methylpyridin-3-yl]-4,5-dihydro-3,6-diphenyl-2H-thiopyran-2-carboxamide;
N-[2,4-bis(methylthio)-6-methylpyridin-3-yl]-3,6-bis-3-(cyclohexylthio)propyl-4,5-dihydro-2H-thiopyran-2-carboxamide;
N-(2,6-diisopropylphenyl)-3,6-dihydro-3,6-dipentyl-2H-thiopyran-2-carboxamide;
N-(2,6-diisopropylphenyl)-3,6-dihydro-4,5-dipentyl-2H-thiopyran-2-carboxamide;
N-[2,4-bis(methylthio)-6-methyl-pyridin-3-yl]-6,7-dimethoxy-4-pentyl-1,2,3,4-tetrahydro-2-thianaphthalene-1-carboxamide;

N-[2,4-bis(methylthio)-6-methylpyridin-3-yl] -7,8 -dimethoxy-4-pentyl-1,3,4,5-tetrahydro-2-benzothiepin-1 -carboxamide;

N-[2,4-bis(methylthio)-6-methylpyridin-3-yl] -4 -butyl-7,8-dimethoxy-1,3,4,5-tetrahydro-2-benzothiepin-1 -carboxamide;

N-[2,4-bis(methylthio)-6-methylpyridin-3-yl]-4 -butyl-7-methoxy-8-pentoxy-1,3,4,5-tetrahydro-2 -benzothiepin-1-carboxamide;

N-[2,4-bis(methylthio)-6-methylpyridin-3-yl]-1α -O-methyl-2,3-O-dibutyl-4-O-benzyl-D-glucuronamide;

N-[2,4-bis(methylthio)-6-methylpyridin-3-yl]-1 -deoxy-2,3-O-dibutyl-4-O-benzyl-D-glucuronamide;

N-[2,4-bis(methylthio)-6-methylpyridin-3-yl]-1α -O-methyl-2,3,4-O-tributyl-D-glucuronamide;

N-[2,4-bis(methylthio)-6-methylpyridin-3-yl]-1 -deoxy-2,3, 4-O-tributyl-D-glucuronamide;

N-[2,4-bis(methylthio)-6-methylpyridin-3-yl] -1,2-O-isopropylidene-3-O-butyl-D-xylofuranuronamide;

N-(3-phenyl-1,2,4-thiadiazol-5-yl)-1,2-O-isopropylidene-3-O-butyl-D-xylofuranuronamide;

N-[2,4-bis(methylthio)-6-methylpyridin-3-yl]-1α -O-methyl-3-O-butyl-D-xylofuranuronamide;

N-[2,4-bis(methylthio)-6-methylpyridin-3-yl]-1α -O-methyl-2,3-O-dibutyl-D-xylofuranuronamide;

N-[2,4-bis(methylthio)-6-methylpyridin-3-yl]-1β -O-methyl-2,3-O-dibutyl-D-xylofuranuronamide;

N-[2,4-bis(methylthio)-6-methylpyridin-3-yl]-1 -deoxy-2,3-O-dibutyl-D-xylofuranuronamide;

N-(2,4,6-trimethoxyphenyl)-1-deoxy-2,3-O-dibutyl-D-xylofuranuronamide;

N-(2,6-diisopropylphenyl)-1-deoxy-2,3-O-dibutyl-D-xylofuranuronamide;

The present invention also provides pharmaceutical compositions comprising a compound of Formula I and a pharmaceutically acceptable carrier.

The compounds described above are useful as antiatherosclerotic and antihypercholesterolemic agents in a mammal when administered as pharmaceutical compositions to a mammal in need of treatment with such antiatherosclerotic and antihypercholesterolemic agents. The present invention includes pharmaceutical compositions containing an effective ACAT-inhibiting or antiatherosclerotic or cholesterol-lowering amount of the above described compounds of Formula I. The present invention also includes methods of treating hypercholesterolemia or atherosclerosis in a mammal comprising administering to the mammal a therapeutically effective amount of a compound of Formula I described above.

The compounds of the present invention can also be administered in combination with one or more additional therapeutic agents. Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

By "therapeutically effective amount" it is meant an amount of a compound of Formula I that when administered alone or in combination with an additional therapeutic agent to a cell or mammal is effective to inhibit ACAT so as to prevent or ameliorate the atherosclerosis or hypercholesterolemia disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable occurs more than one time in any constituent or in any formula, its definition on each occurrence is independent of its definition at every other occurrence. Thus, for example, if a group is shown to be substituted with 0–3 $R^{30}$, then said group may optionally be substituted with up to three $R^{30}$ and $R^{30}$ at each occurrence is selected independently from the defined list of possible $R^{30}$. Also, by way of example, for the group —N($R^{5a}$)$_2$, each of the two $R^{5a}$ substituents on N is independently selected from the defined list of possible $R^{5a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring.

When a substituent is listed without indicating the atom via which such substituent is bonded to the rest of the compound of Formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$–$C_{10}$" denotes alkyl having 1 to 10 carbon atoms); "haloalkyl" is intended to include both branched and straight-chain saturated aliphatic hydrocarbon groups having the specified number of carbon atoms, substituted with 1 or more halogen (for example —$C_vF_w$ where v= 1 to 3 and w= 1 to (2v+1)); "alkoxy" represents an alkyl group of indicated number of carbon atoms attached through an oxygen bridge; "alkylthio" represents an alkyl group of indicated number of carbon atoms attached through an sulfur bridge; "dialkylamino" represents a N atom substituted with 2 alkyl groups of the indicated number of carbon atoms;

"cycloalkyl" is intended to include saturated ring groups, including mono-,bi- or poly-cyclic ring systems, such as cyclopropyl, cyclobutyl, cyclopentyl, cyclohexyl, cycloheptyl, cyclooctyl, and adamantyl; and "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "—(alkyl)—", "—(alkenyl)—" and "—(phenyl)—", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7 -membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heteroaryl" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5 -thiadiazinyl, 2H,6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the educt molecule must be compatible with the reagents and reactions proposed. Not all compounds of Formula I falling into a given class may be compatible with some of the reaction conditions required in some of the methods described. Such restrictions to the substituents which are compatible with the reaction conditions will be readily apparent to one skilled in the art and alternate methods must then be used.

The strategy of synthesis of compounds of Formula I wherein Y is a carbonyl group begins with the disconnection described in Scheme I. The coupling shown there may be accomplished in several ways. Standard peptide coupling reagents (well familiar to those skilled in the art) may be employed, including dicyclohexylcarbodiimide, N,N-carbonyldiimidazole, isobutylchloroformate, and other analogous reagents and conditions. Alternatively, compounds of formula (1) may be first converted to the acid chloride. Treatment of such intermediates with compounds of formula (2) with an appropriate base, such as triethylamine, then produces the amide of Formula I.

Scheme I

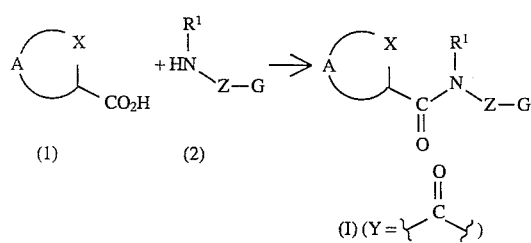

Compounds of Formula I wherein Y is $(CH_2)_m$ can be prepared by the reaction sequence shown in Scheme II. The same coupling technology discussed above may be used for the preparation of compounds of formula (4). The reduction of the carbonyl group in this amide compound may be accomplished using reagents such as lithium aluminum hydride, borane-tetrahydrofuran complex, diisobutylaluminum hydride or sodium bis(methoxyethoxy)aluminum hydride.

Scheme II

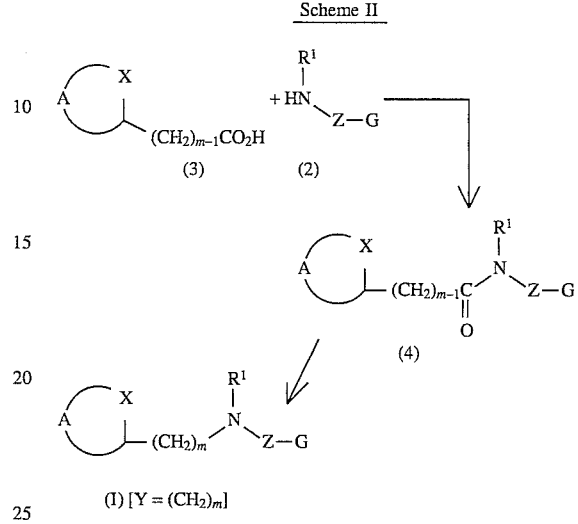

Synthesis of compounds of Formula I wherein Y is $-(CH_2)_m-NHC(=O)-$ may be accomplished by the technology portrayed in Scheme III. The carboxylic acid group in the compound of formula (5) may be converted to an isocyanate group using the Curtius rearrangement reaction. This result may be achieved by the treatment of the acid with a reagent such as diphenylphosphoryl azide, but may also be accomplished by treatment of the acid chloride corresponding to compound (5) with sodium azide. The intermediate isocyanate compound of formula (6) need not be isolated, but is treated directly with amine compound (2) to afford the urea compound of Formula I.

Scheme III

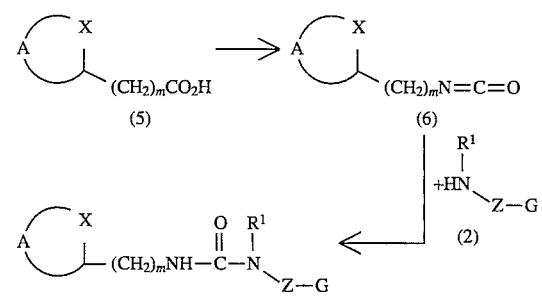

Scheme IV

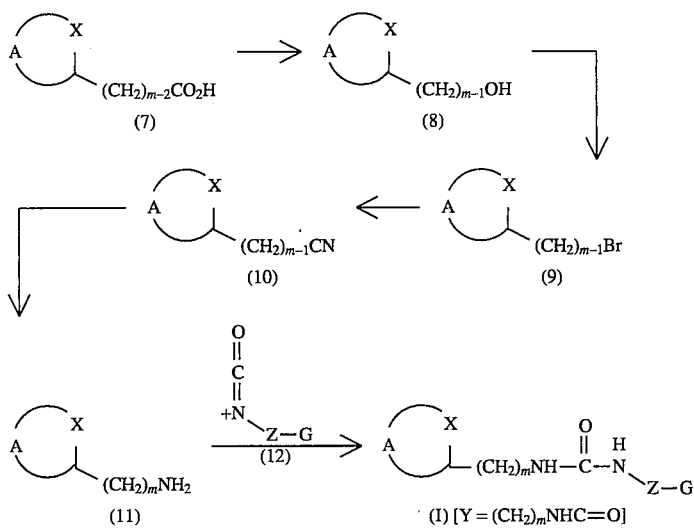

Alternatively, compounds of Formula I wherein Y is —(CH$_2$)$_m$—NHC(=O)— and R$^1$ is H may be prepared using the coupling method shown in Scheme IV, above. The carboxylic acid compound of formula (7) can be reduced to the alcohol (8) using reagents such as borane-tetrahydrofuran complex or lithium aluminum hydride. The hydroxy group in compound (8) may be converted to a bromide employing such reagents as phosphorus tribromide or carbon tetrabromide/triphenyl-phosphine. The bromide in compound (9) may be displaced with cyano using such reagents as potassium cyanide, in solvent systems which are either very polar (such as dimethylsulfoxide) or promote phase-transfer catalysis (such as water/chloroform, and the presence of a phase-transfer catalyst such as a long-chain alkyl-trimethylammonium halide salt). The cyano group may be reduced to aminomethylene using such reagents as borane-tetrahydrofuran complex or lithium aluminum hydride, which results in the preparation of the compound of formula (11). This amine compound may then be coupled to an isocyante compound of formula (12) to afford the urea.

Scheme V

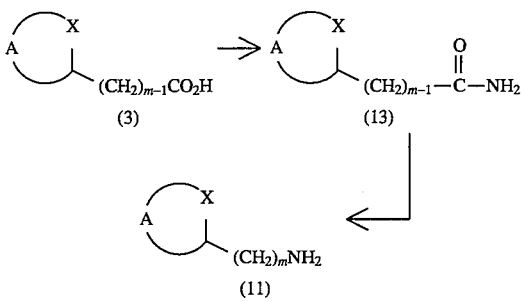

An alternative method of preparing the intermediate amine (11) is shown in Scheme V. Acid compound (3) can be activated exactly as described for Scheme II, and coupled to ammonia to afford the amide (13). Reduction of the amide group in the manner described above will then generate the amine compound (11).

Scheme VI

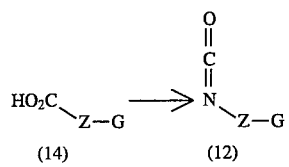

In the event that the particular isocyanate compound of formula (12) is not commercially available, it may be generated by the Curtius rearrangement method described above from the carboxylic acid compound of formula (14) (Scheme VI).

Methylene homologation reactions or sequences may be used to convert carboxylic acid compounds of the formula (1) [or (3), (5), or (7)] to longer-chain homologues. Two examples of these techniques, which are popular in organic synthesis and should be familiar to those skilled in the art, are shown in Scheme VII. The compound of formula (7) may be converted exactly as described above to one of formula (10). The nitrile (10) may be converted to the acid compound of formula (3) using conditions such as strong mineral acid or alkali base and heat. The previously-mentioned alcohol (8) may be oxidized to the aldehyde (15) using such reagents as pyridinium chlorochromate, pyridinium dichromate, dimethylsulfoxide/oxalyl chloride/triethylamine, etc. Coupling with a Horner-Emmons-type reagent such as the lithium salt of triethylphosphonoacetate then will afford the unsaturated carboxylic ester compound (16). Reduction of the carbon-carbon double bond may be accomplished with the use of such reagents as hydrogen (with a catalyst, such as palladium on carbon), sodium bis(methoxyethoxy)aluminum hydride (with catalytic copper (I) bromide), etc. Hydrolysis of the carboxylic ester may be accomplished by using such reagents as sodium hydroxide in ethanol, lithium iodide in dimethylsulfoxide, etc. Thus, any length carbon chain tether from the X-containing ring to a carboxylic acid group may, in principle, be constructed starting with the simplest member in the series, namely the compound of formula (1).

Scheme VII

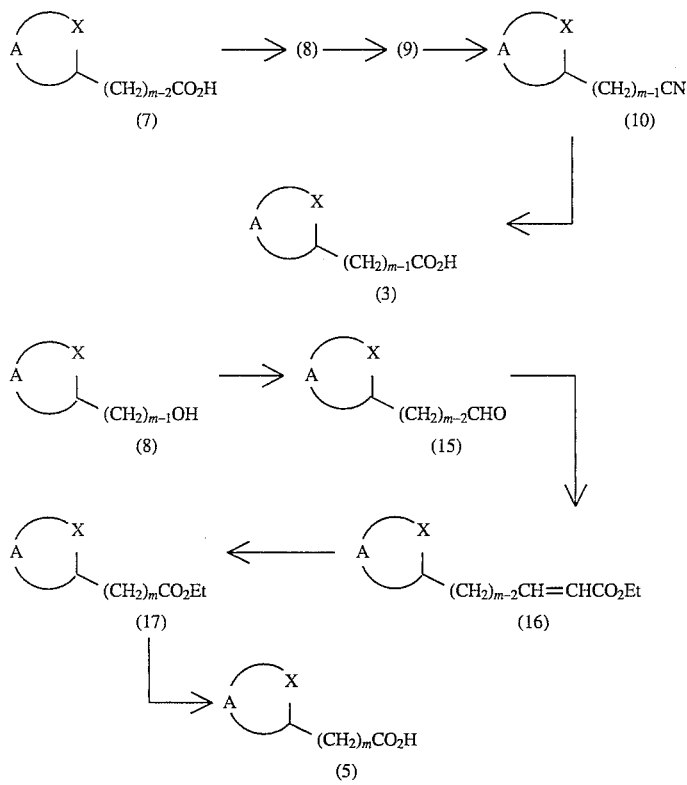

Scheme VIII

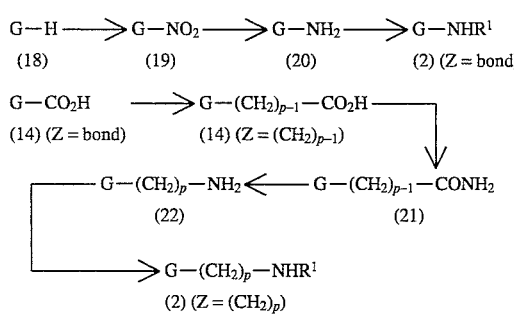

The preparation of the compounds whose formula includes the group G may be prepared from simpler starting materials using the procedures shown in Scheme VIII. An aromatic or heteroaromatic compound (18), which for the scope of this application are available using standard aromatic and heterocyclic chemistry, may be nitrated in some fashion employing a reagent such as nitric acid. The nitro-substituted compound (19) may be reduced using such reagents as hydrogen (with catalytic palladium on carbon), tin (II) chloride, zinc dust in acetic acid, sodium hydrosulfite, etc. The amino-bearing compound (20) (equivalent to compound (2) wherein Z is a bond and $R^1$ is H) may be elaborated to more highly-substituted analogues using standard amine alkylation methodology. For the compounds of formula (2) wherein Z is a carbon chain, a carboxylic acid compound of formula (14) wherein Z is a bond may be subjected to the homologation technology discussed above to prepare the higher homologue. Activation of the carboxylic acid group and amination affords the amide compound of formula (21). Reduction as before generates the amine (22), and further functionalization of the nitrogen (if desired) will then give the compound of formula (2) wherein Z is a chain of methylene groups.

Scheme IX

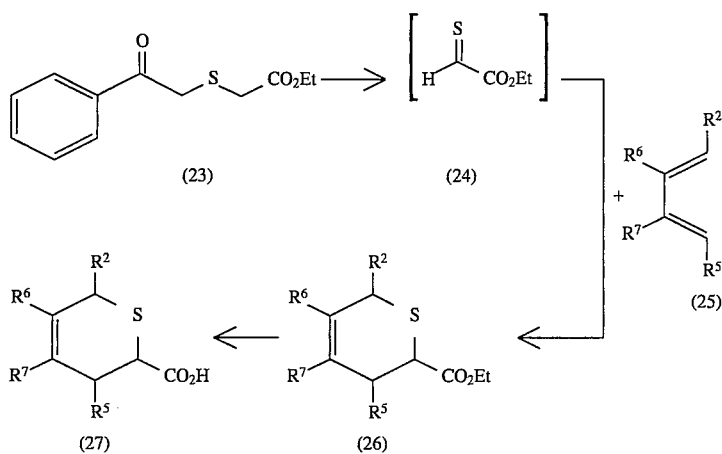

The synthesis of one version of compound (1), with generic formula (27), is shown in Scheme IX. The dihydrothiopyran ring is conveniently built employing a hetero- pound (26) using the methods discussed earlier (see, for example, Scheme VII) will then give the acid compound (27).

Diels-Alder cycloaddition between an appropriately-substituted 1,3-butadiene (compound (25)) and a carboalkoxy-substituted thioaldehyde of formula (24). This compound may be generated in situ using the photolyric method described by Vedejs et al., *J. Org. Chem.*, 51: 1556 (1986). This paper also provides the procedure for the preparation of the starting material, compound (23), which was repeated for this work. Hydrolysis of the carboxylic ester in com- Scheme X

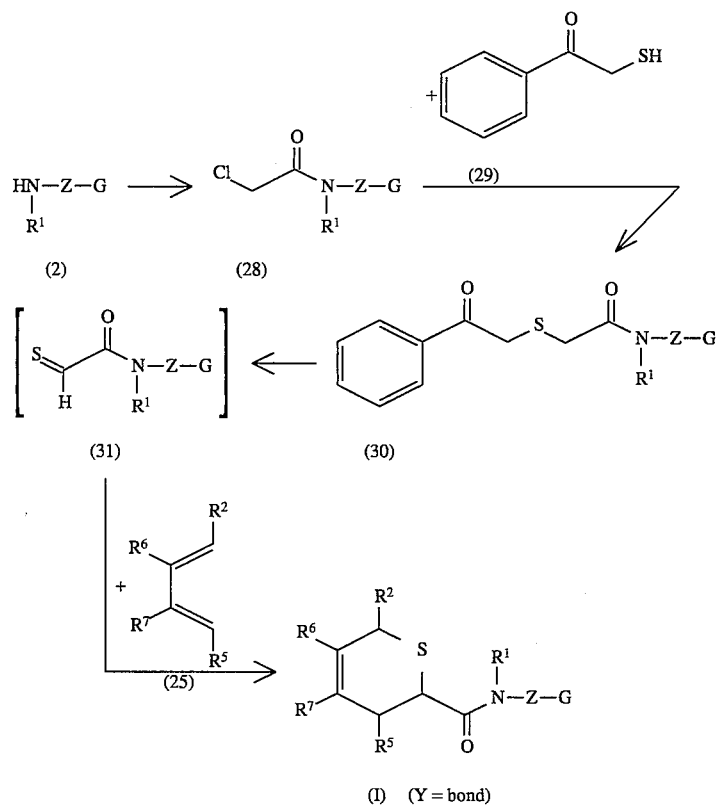

An equally successful strategy for this type of compound involves the cycloaddition reaction of a thioformyl amide of formula (31) (Scheme X). The starting material for this reaction, the phenacyl sulfide compound (30), can be prepared by coupling phenacyl thiol (compound (29), prepared according to Vedejs, et al., *J. Org. Chem.*, v. 51, p. 1556 (1986)) with a chloroacetamide compound of formula (28), using a base such as triethylamine or potassium carbonate.

The chloroacetamide may be prepared by reacting the amine compound (2) with a reagent such as chloroacetyl chloride or chloroacetic anhydride. The sulfide compound (30) is then photolyzed as for the carboethoxy compound, and in situ trapping of the thioaldehyde compound (31) with the diene compound (25) will afford the fully-elaborated amide compound of Formula I.

diimide may be used. Diimide is generated in situ from such reagents and conditions as hydrazine/copper (II) halide, dipotassium azodicarboxylate/acetic acid, toluene-sulfonyl-hydrazide, etc.

Scheme XI

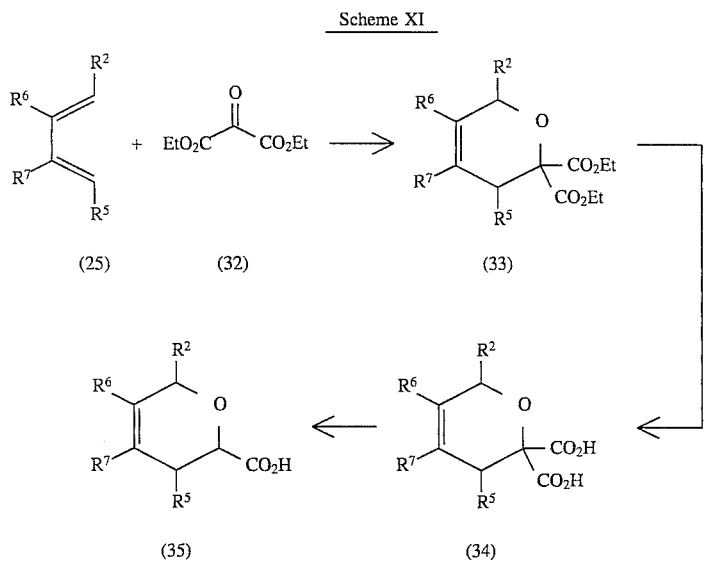

Synthesis of compounds containing a dihydropyrancarboxyl group utilizes the strategy shown in Scheme XI. The method of Bonjouklian and Ruden, *J. Org. Chem.*, v. 42, p. 4095 (1977) may be used to prepare the compound of formula (33), from a hetero-Diels-Alder cycloaddition reaction of diene compound (25) with diethyl ketomalonate. The ester groups are then hydrolyzed using such reagents as potassium hydroxide, and the bis-carboxylic acid is decarboxylated, using such reagents as piperidine or morpholine in solvents such as pyridine.

Scheme XII

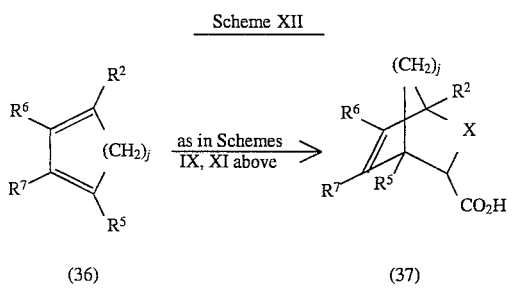

Compounds of Formula I that contain a dihydropyran or dihydrothiopyran ring, wherein the groups $R^3$ and $R^4$ form a bridge of methylene groups, the hetero-Diels-Alder technology shown in Schemes IX, X, and XI may be employed for a 1,3-cycloalkadiene compound (36) (Scheme XII).

Preparation of compounds of Formula I wherein a tetrahydropyran or tetrahydrothiopyran ring is present may proceed by reduction of the corresponding dihydro ring system, as is displayed in Scheme XIII. When X is O, this transformation may be accomplished by catalytic hydrogenation (hydrogen plus an appropriate catalyst). When X is S, the catalytic hydrogenation method cannot conveniently be employed, due to "poisoning" of most catalysts by the presence of sulfur in the molecule. Here, a reagent such as Scheme XIII

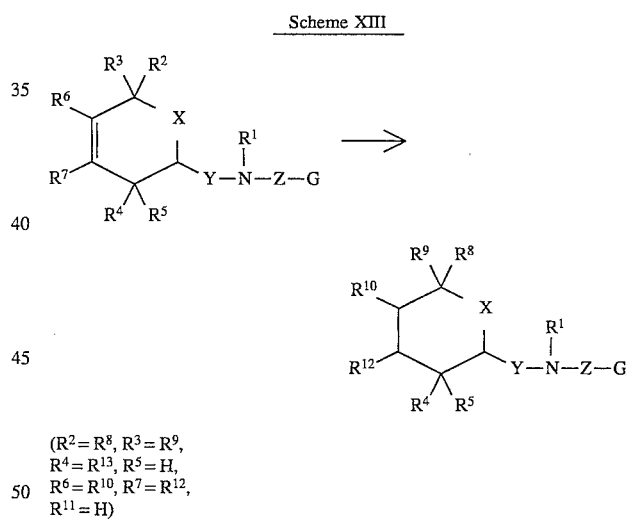

($R^2 = R^8$, $R^3 = R^9$,
$R^4 = R^{13}$, $R^5 = H$,
$R^6 = R^{10}$, $R^7 = R^{12}$,
$R^{11} = H$)

Compounds of Formula I wherein the A group is selected as a five-membered ring and X is sulfur may be prepared starting with diester compound (38) (Scheme XIV). The ester groups may be hydrolyzed to diacid (39), which is in turn subjected to decarboxylation to give carboxylic acid compound (1). The conditions for the reactions of the sequence (38) to (39) to (1) are completely analogous to those shown in Scheme XI. The full elaboration to the compound of Formula I proceeds as discussed above.

The compound of formula (38) may be prepared in several ways, two of which are shown in Scheme XV. According to the method of Ando et al., *J. Org. Chem.*, v. 37, p. 1721 (1972), a thiacyclobutane compound (40) is treated with diethyldiazomalonate (41) employing catalysis by an agent such as copper (I) sulfate, copper powder, copper bronze or rhodium (II) acetate dimer. The resulting ring expansion then affords compound (38) directly. Compound (41) may be prepared from treatment of diethyl-malonate with a diazo transfer reagent such as p-toluene-sulfonyl azide, p-acetamidobenzenesulfonyl azide, or azidotris(diethylamino)phosphonium bromide. Alternatively, the method of Ikegami et al., *Tetrahedron*, v. 30, p. 2087 (1974) may be used, whereby a dibromo compound of formula (42) is cyclocondensed with sodium sulfide to afford (38).

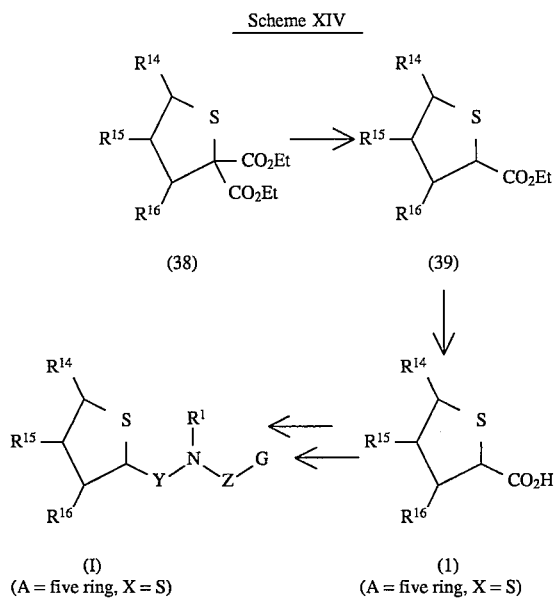

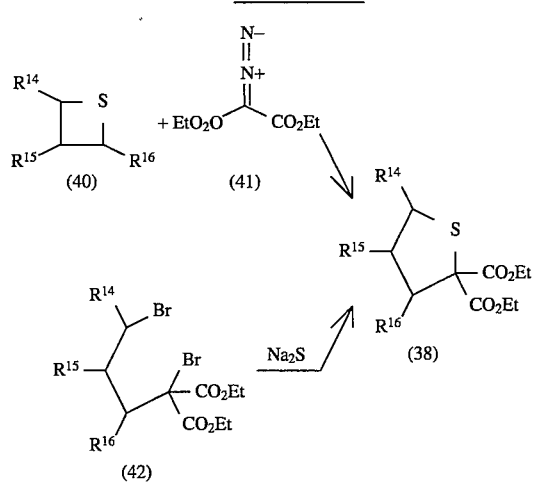

Synthesis of compounds of Formula I wherein the A group is selected as a five-membered ring and X is oxygen can be accomplished according to the routes shown in Schemes XVI and XVII. The key intermediate, acid compound (1), is derived from ester compound (43) by hydrolysis (analogous to the methods discussed earlier). Three possible syntheses of compound (43) are given in Scheme XVII. The method of Noyori et al., *Tetrahedron*, v. 22, p. 3393 (1966) describes the treatment of oxetanes like compound (44) with ethyl diazoacetate, compound (45), in the presence of a copper powder catalyst. The work of Speckamp et al., *Tetrahedron Letters*, v. 32, p. 1491 (1991) details the generation of α-alkoxyacetate radical intermediates from sulfur-bearing compounds of formula (46), employing reagents such as tributyltin hydride with catalysis from a radical initiator such as azoisobutyro-nitrile. Reductive cyclization then results in the compound of formula (43). Finally, the method of Ikegami et al., *Tetrahedron*, v. 30, p. 2087 (1974) employs compounds of formula (47); treatment with hydrogen at 100 atmospheres in the presence of Raney nickel catalyst, results in reduction to compound (43).

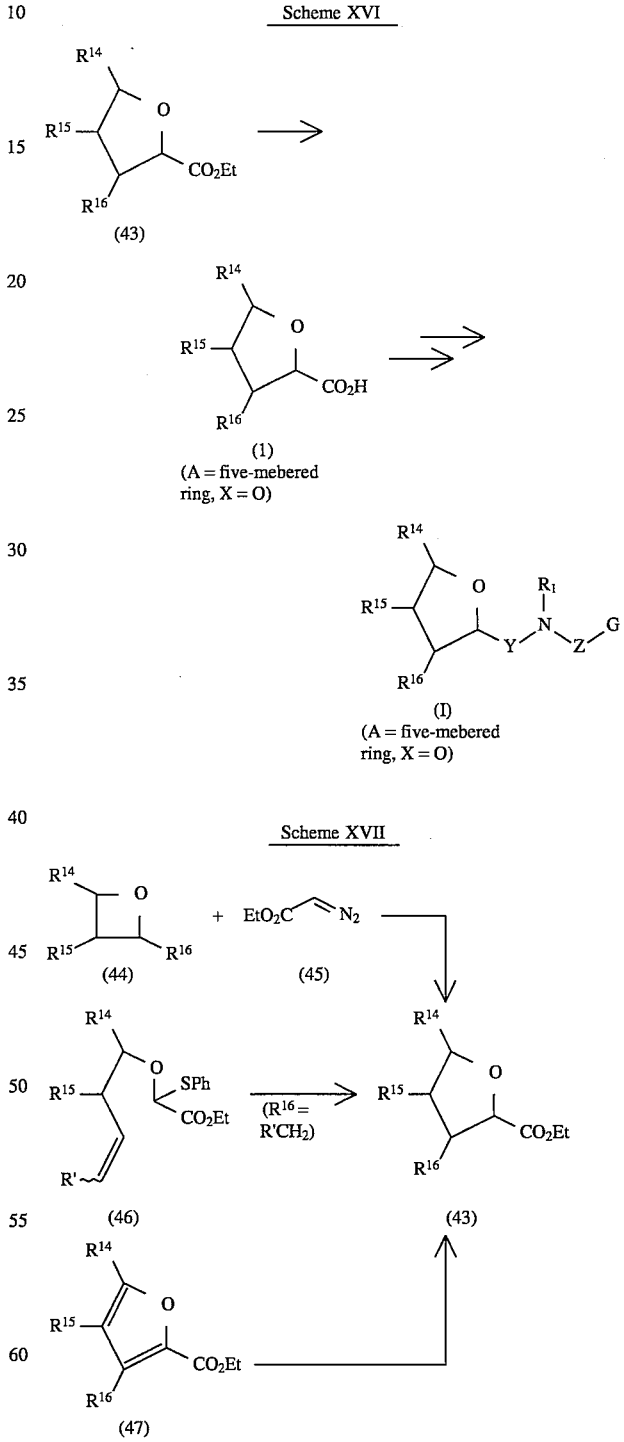

Synthesis of compounds of Formula (1) wherein a benzene ring is fused to a tetrahydropyran is shown in Scheme XVIII. A benzoic acid or ester may be homologated by one methylene group to the substituted phenylacetic acid ester, compound (49). The benzylic position may be alkylated by deprotonation with such reagents as sodium ethoxide, potassium tert-butoxide, sodium hydride, lithium diisopropylamide, etc., followed by treatment with an alkyl or benzyl halide to give compound (50). The ester group may then be reduced directly (to afford the compound wherein $R^8$ is H), employing such a reagent as lithium aluminum hydride. The ester may be first partially reduced to the aldehyde, using a reagent such as diisobutylaluminum hydride. Treatment with a carbon nucleophile reagent, such as an organomagnesium halide, then will give the compound of formula (51) wherein $R^8$ is not H. Cyclization of this phenethyl alcohol compound may be achieved using such reagents as ethyl diethoxyacetate with catalysis by such reagents as trimethylsilyl trifluoromethanesulfonate to afford compound (52). The ester functionality may be hydrolyzed to carboxylic acid compound (1) as described earlier.

pseudohalide compound such as (53); conversion to bromide, for example, may be accomplished as previously described (see Scheme IV and accompanying text). Displacement by thioacetate can be effected by treating the bromide compound with thiolacetic acid in the presence of a base such as potassium carbonate, using, if necessary, a catalyst such as tetrabutylammonium iodide, to give compound (54). Hydrolysis of the thioacetate group can occur by treatment with a reagent such as sodium hydroxide, to give a thiol compound (55). Cyclization to the benzotetrahydrothiopyran carboxylate compound (56) is accomplished exactly as for the oxygen analogue (ethyl diethoxyacetate, trimethylsilyl trifluoromethanesulfonate) and hydrolysis as before gives the carboxylic acid compound of formula (1).

Scheme XVIII

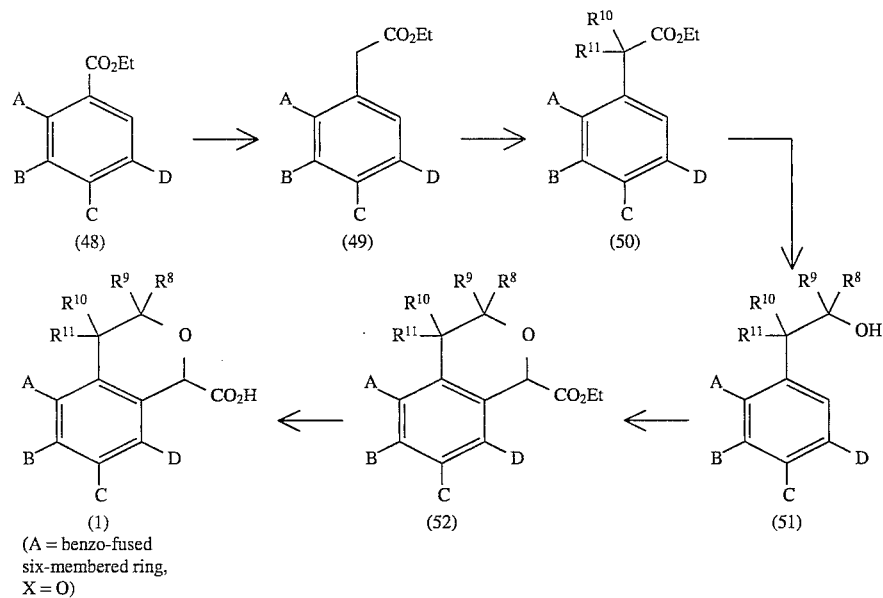

(A = benzo-fused six-membered ring, X = O)

The analogous series wherein X is S may be prepared as shown in Scheme XIX. The previously-described alcohol compound of formula (51) may be converted to a halide or Scheme XIX

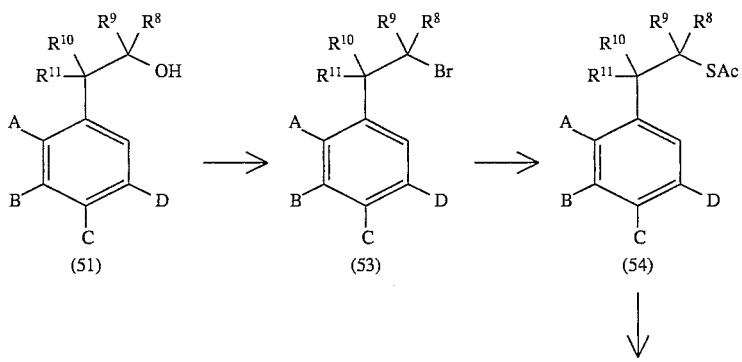

-continued
Scheme XIX

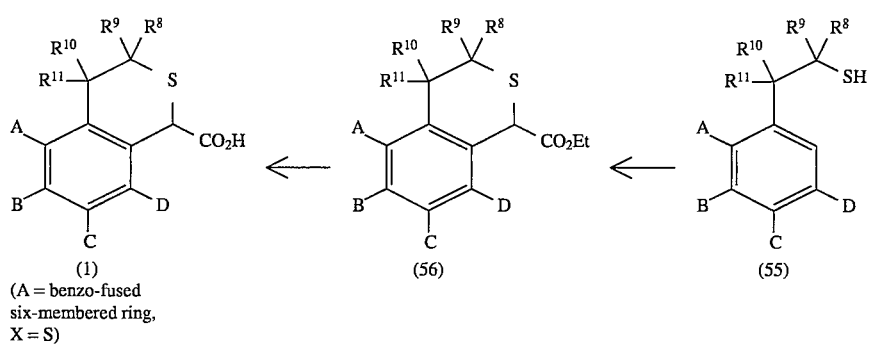

(1)
(A = benzo-fused
six-membered ring,
X = S)

Synthesis of compounds containing a seven-membered ring (both mono- and bicyclic) can be performed by using homologous versions of the strategies discussed above. In particular, the methods shown in Schemes XIV, XV, XVI and XVII may be adapted to the synthesis of seven-membered ring compounds by using the bishomologues of the intermediates displayed. The homologous version of the synthesis shown in Schemes XVIII and XIV also are useful in the preparation of compounds containing a benzo-fused seven-membered ring. For example, Scheme XX shows the preparation of the sulfide case. An appropriately-substituted benzyl bromide compound (57) is used to alkylate a sodiomalonate salt to afford compound (58). The diester may be converted to the mono-ester (59) by hydrolysis as discussed above, followed by decarboxylation using conditions similar to those employed for the transformation (33)–(34). The ester group may be reduced to the hydroxymethyl group of compound (60) using conditions discussed previously. The conversion of compound (60) to (61) to (62) to (63) to (64) to (1) is exactly analogous to the route shown in Scheme XIX.

An alternative approach to compound (59) is presented in Scheme XXI. Widely-available substituted benzaldehyde compounds (65) may be reacted with such reagents as phosphonoacetate compound (66). The reaction is usually performed with the alkali salt of compound (66), but may also be performed in the presence of a base such as potassium fluoride. The resulting olefin compound (67) may then be reduced by such methods as catalytic hydrogenation or dissolving metal reduction to give the ester compound (59).

Scheme XX

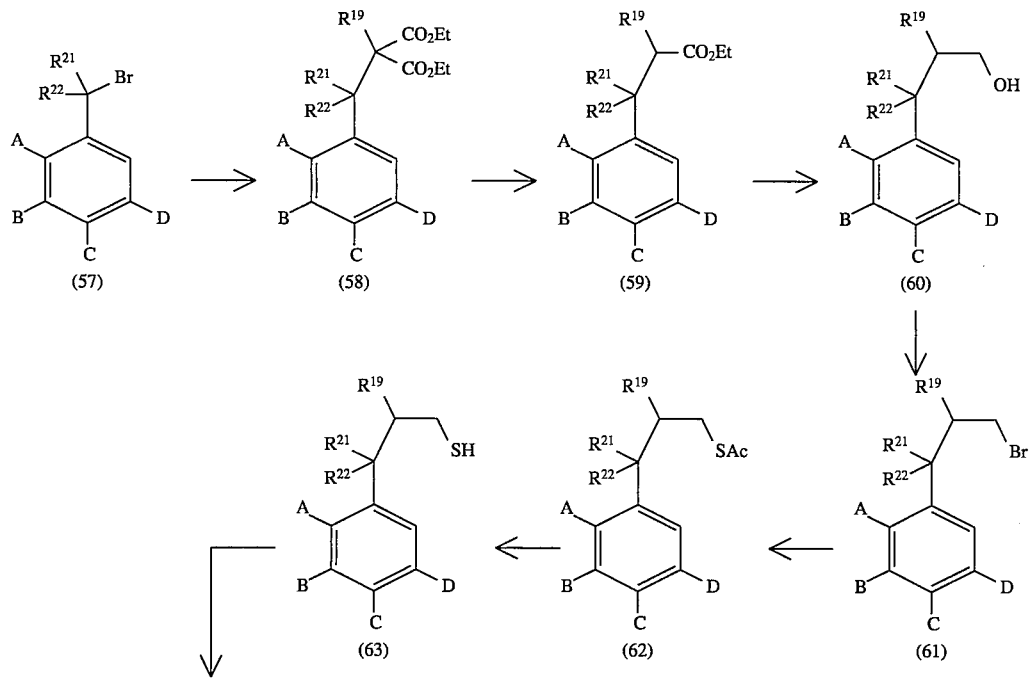

-continued
Scheme XX

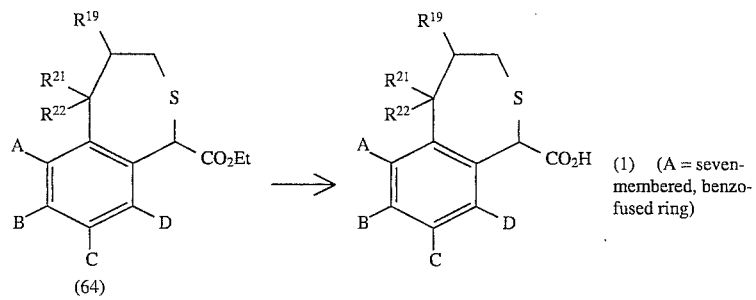

(1) (A = seven-membered, benzo-fused ring)

Scheme XXI

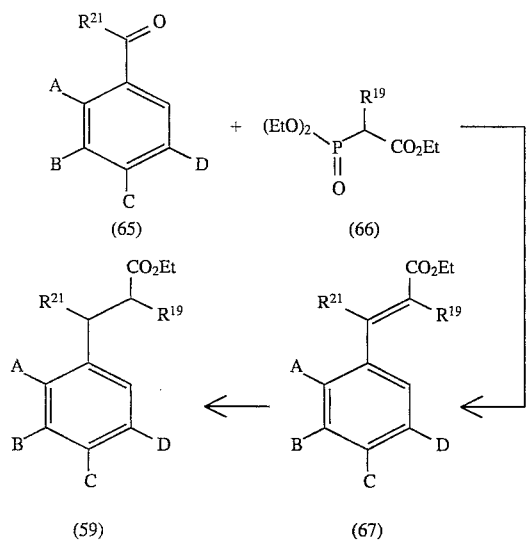

Synthesis of compounds wherein A is

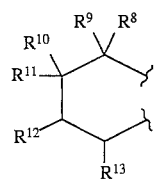

and $R^{12}$ is a oxygen atom of a carbonyl group, may be prepared using the method of Scheme XXII. The ring system is constructed by a hetero-Diels Alder reaction (as described above) with a trialkylsiloxy-substituted butadiene compound (68). Hydrolysis of cycloadduct (69) then gives the ketone (70). Additional functionalization of the ring system may be achieved by using a labile substituent on compound (68), wherein the hydrolysis reaction then gives an enone compound (71). The enone may be functionalized by Michael addition of alkoxy or alkylthio groups, or by cuprate-mediated 1,4-addition of carbon nucleophiles. Ester compounds like (70) or (72) are then transformed as described above to compounds of Formula I.

Scheme XXII

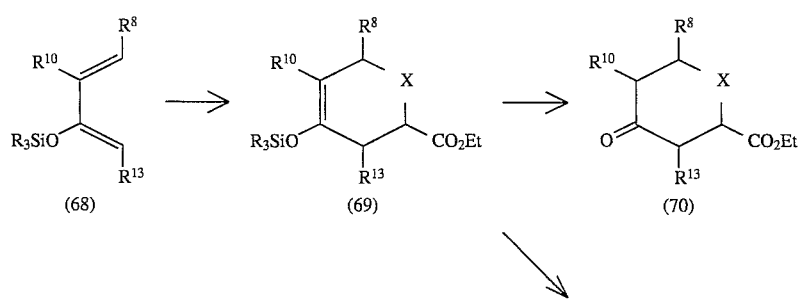

-continued
Scheme XXII

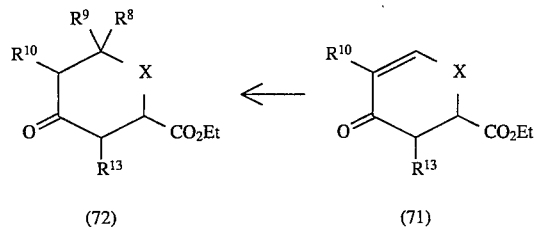

The compounds of Formula I wherein A is

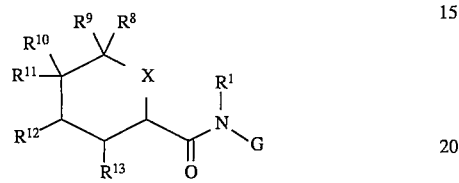

and $R^8$–$R^{13}$ are mostly alkoxy in nature may be prepared using carbohydrates as starting materials and methods of transformation which are well known among those in the area of carbohydrate chemistry using the procedure shown in Scheme XXIII. Preparations of the carbohydrate derivatives (74) are well documented in the carbohydrate literature such as Methods in Carbohydrate Chemistry Vol 1–7, Roy L. Whistler and M. L. Wolfram editors, Academic Press, New York, 1962–1976, and Carbohydrate Chemistry, Vol 1–24, R. J. Ferrier, reporter, The Royal Society of Chemistry, Thomas Graham House, Science Park, Cambridge, 1968–1992. Synthesis of the alcohol (74) from the carbohydrate (73) may require protection and deprotection steps. The alcohol (74) is oxidized with Jones reagent to the corresponding acid (76). I may also be coverted to the aldehyde (75) with pyridinium chlorochromate (PCC) or pyridinium dichromate (PDC), and then the aldehyde is treated with either Jones reagent or sodium chlorite to give the acid (76). The amide bonds are formed as discussed in Scheme I.

Scheme XXIII

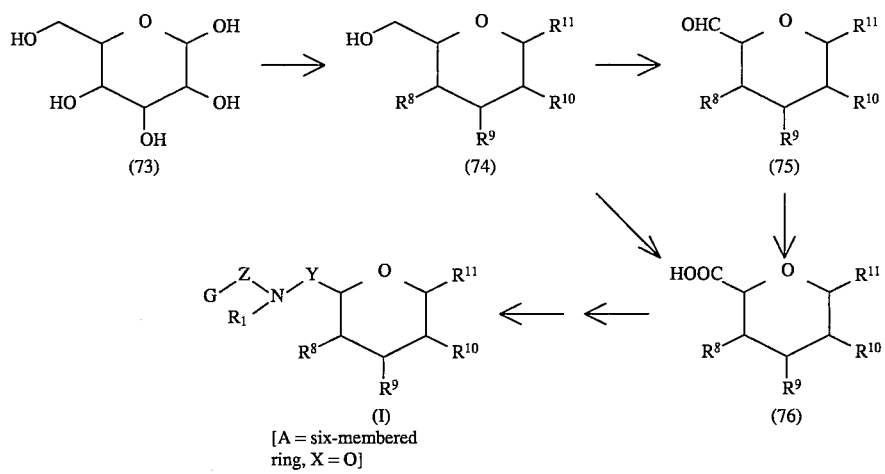

Scheme XXIV

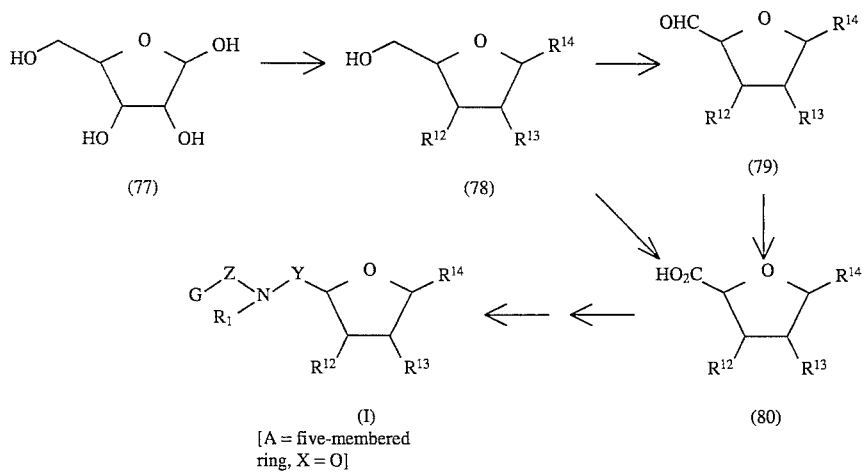

Compounds of Formula I wherein the A group is a five-membered ring, substituted with 1 to 3 alkoxy, aryloxy, arylalkoxy, alkenyloxy or alkynyloxy, and X is oxygen may be prepared from an appropriate carbohydrate using the procedure shown in Scheme XXIV. Preparations of the carbohydrate derivatives (77) are well documented in the carbohydrate literature such as Methods in Carbohydrate Chemistry Vol 1–7, Roy L. Whistler and M. L. Wolfram editors, Academic Press, New York, 1962– 1976, and Carbohydrate Chemistry, Vol 1–24, R. J. Ferrier, reporter, The Royal Society of Chemistry, Thomas Graham House, Science Park, Cambridge, 1968– 1992. Synthesis of the alcohol (78) from the carbohydrate (77) or a hexose (73) may require protection and deprotection steps. The alcohol (78) is oxidized with Jones reagent to the corresponding acid (80). I may also be coverted to the aldehyde (79) with PCC or PDC, and then the aldehyde is treated with either Jones reagent or sodium chlorite to give the acid (108). The amide bonds are formed as discussed in Scheme I.

Scheme XXV

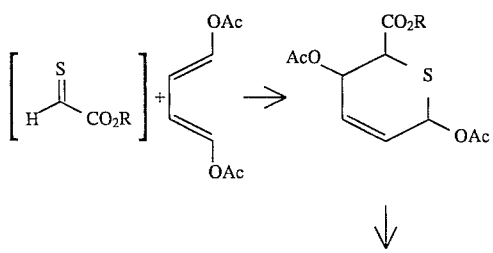

-continued
Scheme XXV

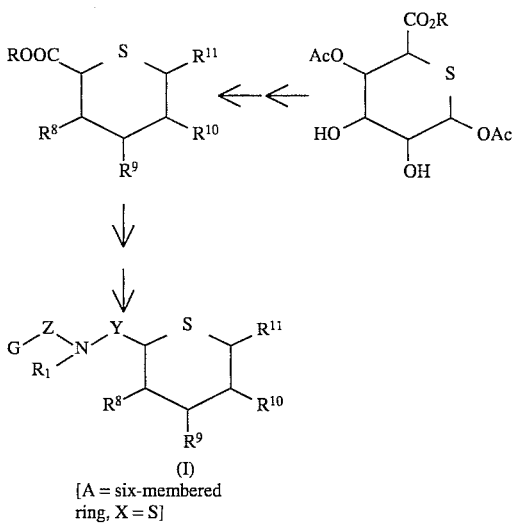

Compounds of Formula I wherein the A group is a six-membered ring, substituted with 1 to 4 alkoxy, aryloxy, arylalkoxy, alkenyloxy or alkynyloxy, and X is sulfur may be prepared using the procedure described in David Adam et al, J. Chem. Soc., Perkin Trans. I, 1261– 1264 (1992) and alkylation reaction with appropriate alkylating agents (Scheme XXV). The amide bonds are formed as discussed in Scheme I.

Scheme XXVI

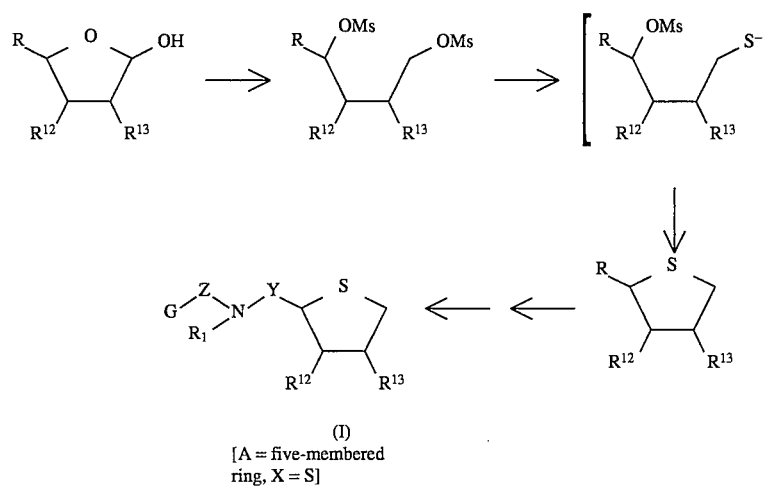

(I)
[A = five-membered ring, X = S]

Compounds of Formula I wherein the A group is a five or six-membered ring, substituted with 1 to 4 alkoxy, aryloxy, arylalkoxy, alkenyloxy or alkynyloxy, and X is sulfur may be prepared using the procedure described in Ohrui and Emoto, Tet. Lett. 2765 (1975) followed by appropriate functional group interchange (Scheme XXVI) and an amide formation reaction discussed in Scheme I.

The compounds from specific example 577 were prepared as shown in Scheme XXVII. The compounds from Examples 426 and 442 are shown in Scheme XXVIII, and that from Ex. 434 is shown in Scheme XXIX.

The compounds of this invention and their preparation can be further understood by the following examples, which exemplify but do not constitute a limit of their invention. In these examples, unless otherwise indicated, all temperatures are in degrees centigrade and parts and percentages are by weight.

Scheme XXVII

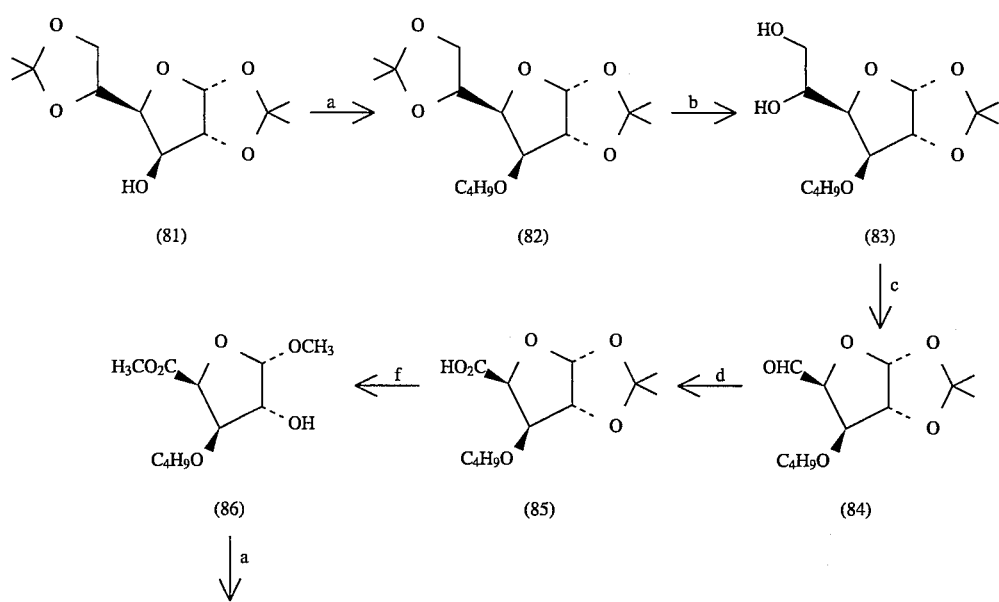

-continued
Scheme XXVII
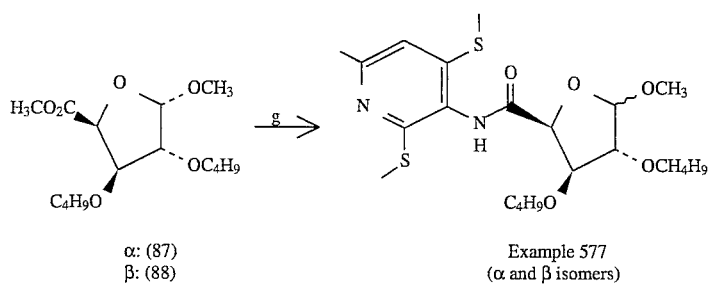
α: (87)
β: (88)
Example 577
(α and β isomers)
a. NaH, n-C$_4$H$_9$I, THF-DMF (4:1), reflux; b. 70% aq AcOH, RT; c. NaIO$_4$, MeOH-H$_2$O, RT; d. NaClO$_2$, sulfamic acid, tBuOH-H$_2$O, RT; e. isobutyl chloroformate, N-methylmorpholine (NMM), 3-amino-2,4-dimethylthio-6-methylpyridine (ADMP), CH$_2$Cl$_2$, 0°~20° C.; f. c-H$_2$SO$_4$, CH$_3$OH, reflux; g. ADMP, Al(CH$_3$)$_3$, CH$_2$Cl$_2$, reflux.
Scheme XXVIII
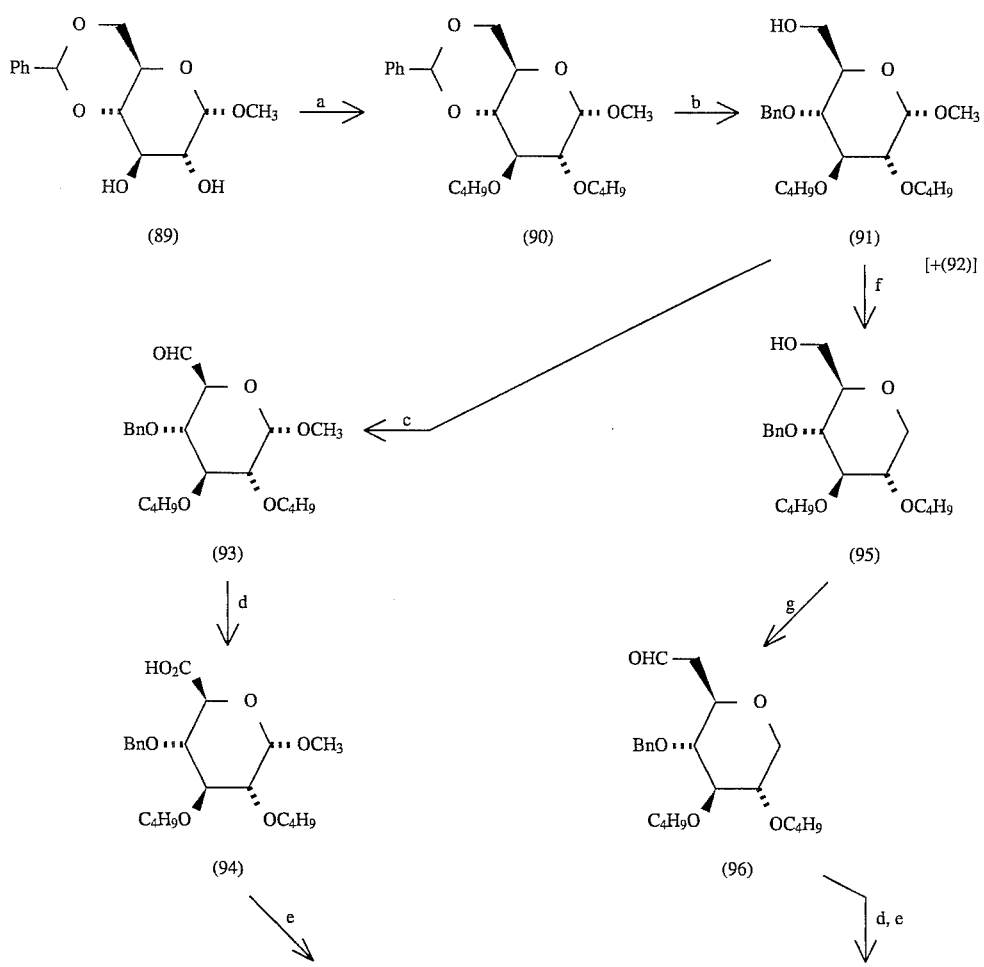

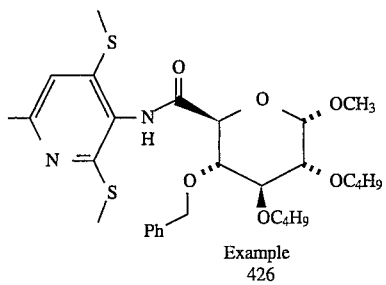

Example 426

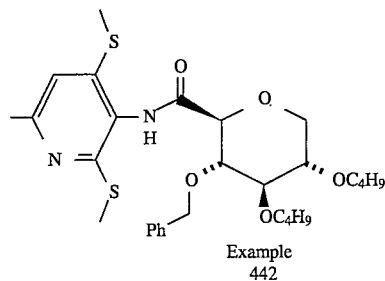

Example 442 a. NaH, n-C₄H₉I, THF-DMF (4:1), reflux; b. LAH, AlCl₃, ether-CH₂Cl₂, RT; c. DMSO, (COCl)₂, NEt₃, −40°~RT; d. NaClO₂, sulfamic acid, tBuOH-H₂O, RT; e. isobutyl chloroformate, N-methylmorpholine (NMM), 3-amino-2,4-dimethylthio-6-methyl-pyridine (ADMP), CH₂Cl₂, 0°~20° C.; f. Et₃SiH, BF₃.Et₂O, CH₂Cl₂, 0° C.; g. PCC, molecular sieves 4A, RT.

CH₂Cl₂, 0°~20° C.; f. CH₃OH, c-H₂SO₄, reflux; g. Et₃SiH, BF₃.Et₂O, CH₂Cl₂, RT; h. 3-amino-2,4-dimethylthio-6-methyl-pyridine, Al(CH₃)₃, ClCH₂CH₂Cl, reflux.

EXAMPLE 70

Preparation of N-[2,4-bis(methylthio)-6-methylpyridin-3-yl] -3,6-dipentyl-2,3-dihydro-2H-thiopyran-2-carboxamide

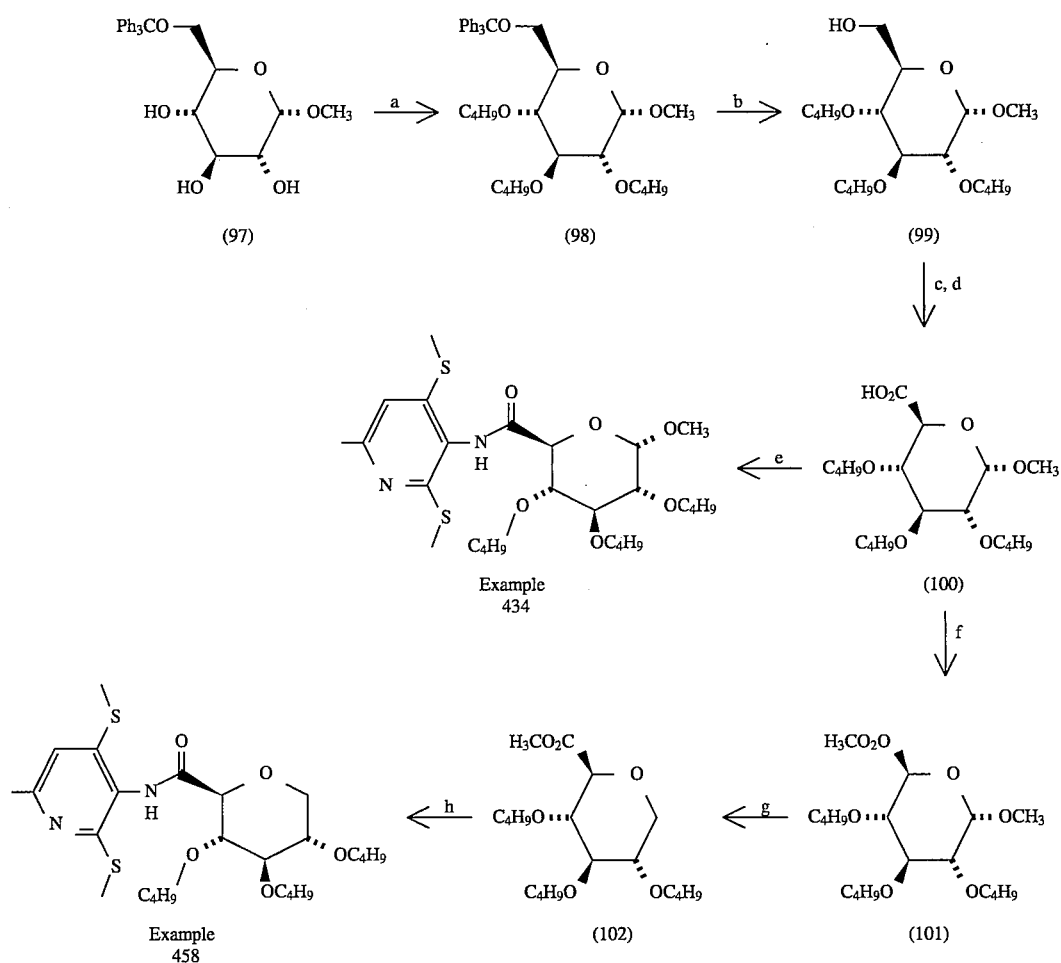

a. NaH, n-C₄H₉I, THF-DMF (4:1), reflux; b. 70% aq AcOH, CHCl₃, 60°; c. DMSO, (COCl)₂, NEt₃, −40°~0° C.; d. NaClO₂, sulfamic acid, tBuOH-H₂O, RT; e. (COCl)₂, NEt₃, DMF, 3-amino-2,4-dimethylthio-6-methyl-pyridine, Method I Part A. A solution of 2-chloroacetophenone (Aldrich, 14.1 g, 91.2 mmol), ethyl 2-mercaptoacetate (Aldrich, 10.0 mL, 91.2 mmol), and potassium carbonate (13.9 g, 100 mmol) in tetrahydrofuran (200 mL) was stirred at ambient temperature for 10 hours. The mixture was poured into water (400 mL), and extracted with methylene chloride (2×400 mL). The extracts were combined, dried over anhydrous magnesium sulfate, filtered and evaporated. The residual oil was separated by flash chromatography (1:4 ethyl acetate-hexane) to afford the product, ethyl 2-phenacylthioacetate, as an oil (16.1 g, 67.7 mmol, 74%). $^1$H NMR (CDCl$_3$): δ 7.97 (2H, dd, J= 8.0, 1.5 Hz); 7.62 (1H, tt, J= 5.1, 1.4 Hz); 7.48 (2H, t, J= 7.7 Hz); 4.19 (2H, q, J= 7.3 Hz); 4.04 (2H, s); 3.33 (2H, s); 1.27 (3H, t, J= 7.3 Hz). Mass spectrum (NH$_3$-CI/DDIP): m/z 256 (100%); 240 (6%); 239 (42%); 210 (1%); 193 (1%).

Part B. Standard Photolysis Procedure: A solution of the sulfide from Part A above (4.00 g, 16.8 mmol) and E,E-6,8-tetradecadiene (prepared according to the method of Zweifel and Miller, *J. Am. Chem. Soc.*, v. 92, p. 6678 (1970), 15.61 g, 80.3 mmol) in benzene (180 mL) was partitioned to 12 100 mL Pyrex roundbottom flasks. The flasks (4 per run; this reaction was performed in 3 runs) were suspended in a Pyrex cooling bath (with a tapwater line for cooling), the bath was filled with 5% aqueous copper sulfate solution (to filter out light wavelengths lower than 310 nm), and the bath was supported above a 270 W sunlamp. The reaction flasks were irradiated for 7 hours (each run); at the end of the three runs, the contents of the flasks were combined and evaporated. The oily residue was separated by flash chromatography (3:97 ethyl acetate-hexane) to afford the product, ethyl 3,6-dipentyl-3,6-dihydro-2H-thiopyran-2 -carboxylate, as an oil (4.53 g, 14.5 mmol, 86%). The material was determined to be a mixture of diastereomers, with one favored to the extent of about 5:1. $^1$H NMR (major isomer, CDCl$_3$): δ 5.80-5.68 (2H, m); 4.19 (2H, q, J= 7.0 Hz); 3.41 (1H, br t, J= 5.9 Hz); 3.33 (1H, d, J= 4.4 Hz); 2.55-2.46 (1H, m); 1.70-1.27 (16H, m); 1.29 (3H, t, J= 7.0 Hz); 0.89 (6H, t, J= 6.8 Hz). Mass spectrum (NH$_3$-CI/DDIP): m/z 330 (30%); 314 (18%); 313 (100%); 279 (2%); 239 (4%).

Part C. A solution of the ester compound from Part B above (4.53 g, 14.5 mmol) and sodium hydroxide (0.25N solution) in 95% ethanol (120 mL, 30.0 mmol NaOH) was stirred for 12 hours at ambient temperature. The reaction mixture was evaporated, and the residue acidified with hydrochloric acid (1N, 150 mL). This was saturated with sodium chloride and extracted with methylene chloride (2×200 mL). The extracts were combined, dried over anhydrous magnesium sulfate, filtered and evaporated to afford the product, 3,6 -dipentyl-3,6-dihydro-2H-thiopyran-2-carboxylic acid, as an oily mixture of diastereomeric products (5:1 by NMR) (4.01 g, 14.1 mmol, 97%). $^1$H NMR (major isomer; CDCl$_3$): δ 5.73 (2H, s); 3.48 (1H, br t, J= 7 Hz); 3.40 (1H, d, J= 3.7 Hz); 2.60-2.52 (1H, m); 1.71-1.24 (16H, m); 0.89 (6H, t, J= 3.7 Hz). Mass spectrum (NH$_3$-CI/DDIP): m/z 287 (6%); 286 (18%); 285 (100%); 239 (25%); 211 (2 %).

Part D. The method of Wang, C. -S., *J. Het. Chem.*, v. 7, p. 389 (1970) was used to convert 4-hydroxy-6-methyl-2 -pyrone (45.5 g, 361 mmol) into 4-hydroxy-6-methyl-2 -pyridone (38.3 g, 306 mmol, 85% for one typical experiment), then 4-hydroxy-6-methyl-2-pyridone (55.6 g, 447 mmol) into 4-hydroxy-6-methyl-3-nitro-2-pyridone (36.3 g, 213 mmol, 48%). The method of Albert, et al., *J. Chem. Soc.*, p. 3832 (1954) was used to convert 4 -hydroxy-6-methyl-3-nitro-2-pyridone (36.3 g, 213 mmol) into 2,4-dichloro-6-methyl-3-nitropyridine (21.2 g, 102 mmol, 48%). This material was dissolved in methanol (150 mL), cooled to 0° C., and treated with sodium thiomethoxide (15.0 g, 214 mmol). After being allowed to stir for 12 hours, the reaction mixture was filtered, and the precipitate was washed with ether. The solid product, 2,4-bis(methylthio)-6-methyl-3-nitropyridine (23.3 g, 101 mmol, 99%), had a melting point of 179°– 180° C. $^1$H NMR (CDCl$_3$): δ 6.79 (1H, s); 2.56 (3H, s); 2.53 (3H, s); 2.47 (3H, s). Mass spectrum (NH$_3$ -CI/DDIP): m/z 233 (10%); 232 (12%); 231 (100%).

Part E. A solution of the nitropyridine compound from Part D above (11.0 g, 47.8 mmol) and hydrochloric acid (conc., 21 mL) in acetic acid (480 mL) was cooled to 0° C., and treated in small portions with zinc powder (36.7 g, 561 mmol). After being allowed to stir for 2 hours, the mixture was filtered and neutralized with sodium bicarbonate. This was extracted twice with methylene chloride, and the extracts were combined, dried over anhydrous sodium sulfate, filtered and evaporated. The residue was separated by flash chromatography (1:9 ethyl acetate-hexane) to afford the product, 3-amino-2,4-bis(methylthio)-6-methylpyridine, as a solid. $^1$H NMR (CDCl$_3$): δ 6.73 (1H, s); 4.03 (2H, s); 2.60 (3H, s); 2.45 (3H, s); 2.43 (3H, s). Mass spectrum (NH$_3$-CI/DDIP): m/z 203 (9%); 202 (12%); 201 (100%); 189 (1%).

An alternate procedure may be used to prepare 3 -amino-2,4-bis(methylthio)-6-methylpyridine. The nitro compound (24.0 g, 30.3 mmol) was suspended in 242 mL of 1:1 water-dioxane, and stirred at ambient temperature while ammonium hydroxide (conc. aqueous, 53 mL) was added. The solution was stirred vigorously for 15 minutes, and sodium hydrosulfite (47.0 g, 270 mmol) was added in portions over 30 minutes. The solution, which warmed and formed a milky white suspension, was stirred for 1 hour, then filtered (with washing with ethyl acetate) and evaporated. The residual liquid was extracted with ethyl acetate (3×), and the extracts were combined, dried over anhydrous magnesium sulfate, filtered and evaporated to afford the product (9.43 g, 45%).

Part F. A solution of the acid compound of Part C above (4.01 g, 14.1 mmol) in benzene (30 mL) was treated with dimethylformamide (0.15 mL), and then oxalyl chloride (4.00 mL, 45.8 mmol). The mixture was stirred for 10 hours, then evaporated. The residue was taken up in tetrahydrofuran (30 mL) under dry nitrogen atmosphere, and delivered dropwise by cannula to an ice-cooled, stirred solution of 3-amino-2,4-bis(methylthio)-6 -methylpyridine (2.80 g, 14.0 mmol) in tetrahydrofuran (30 mL). After being stirred for 14 hours, the mixture was poured into water (200 mL), and extracted with ethyl acetate (2×200 mL). The extracts were washed with saturated brine (200 mL), then combined, dried over anhydrous sodium sulfate, filtered and evaporated. The residue was separated by flash chromatography (3:17 ethyl acetate-hexane) to afford the title product as a waxy solid mixture of two diastereomers (6.46 g, 13.8 mmol, 98%). A portion of the mixture (5 g) was separated by HPLC (column: preparative Pirkle DNBPG, 20× 250 mm; temperature: 20° C.; solvent: 0.1% triethylamine/ 20% isopropanol/80% hexane; flow: 10.0 mL/min; detection: 265 nm UV) to afford the two isomeric products (major: t$_{ret}$ 34 min, weight 3.80 g; minor: t$_{ret}$ 40 min, weight 0.85 g). Major product: mp 88°–89° C. $^1$H NMR (CDCl$_3$): δ 8.31 (1H, br s); 6.65 (1H, s); 5.81 (1H, ddd, J= 11.0, 5.1, 1.8 Hz); 5.69 (1H, br d, J= 11.0 Hz); 3.90-3.81 (1H, m); 3.46 (1H, d, J= 2.2 Hz); 3.08-2.99 (1H, m); 2.50 (3H, s); 2.49 (3H, s); 2.40 (3H, s); 1.75-1.25 (16H, m); 0.89 (6H, t, J= 6.4 Hz). $^{13}$C NMR (CDCl$_3$): δ 169.1, 156.8, 148.7, 133.0, 130.4, 128.1, 123.3, 113.6, 49.5, 41.0, 37.6, 35.3, 32.4, 32.0, 31.7, 27.2, 24.5, 22.7, 22.6, 14.1, 14.0, 13.0, 12.9. IR (KBr): 3440, 3226, 2954, 2922, 2854, 1656, 1564, 1514, 1466, 1432, 1334, 1310, 806 cm$^{-1}$. Mass spectrum (NH$_3$ -CI/DDIP): m/z 469 (17%); 468 (29%); 467 (100%). High-resolution mass spectrum: for C$_{24}$H$_{39}$N$_2$OS$_3$, calculated 467.2225, measured 467.2220, difference 0.9 ppm. Minor product: mp 150°–151° C. $^1$H NMR (CDCl$_3$): δ 7.33 (1H, br s); 6.64 (1H, s); 5.99 (1H, ddd, J= 10.3, 5.2, 2.6 Hz); 5.82 (1H, dr, J= 10.3, 2.0 Hz); 4.03 (1H, d, J= 4.4 Hz); 3.69-3.60 (1H, m); 2.69-2.59 (1H, m); 2.50 (3H, s); 2.48 (3H, s); 2.40 (3H, s); 1.89-1.60 (4H, m); 1.56-1.22 (12H, m); 0.90 (3H, t, J= 7.0 Hz); 0.87 (3H, t, J= 6.9 Hz). $^{13}$C NMR (CDCl$_3$): δ 168.9, 157.3, 156.7, 148.5, 146.1, 133.1, 130.4, 113.7, 49.5, 41.0, 37.6, 35.3, 32.4, 32.0, 31.7, 27.1, 26.7, 24.4, 22.6, 22.5, 14.1 (2C), 14.0, 12.9. Mass spectrum (NH$_3$ -CI/DDIP): m/z 469 (19%); 468 (29%); 467 (100%). Elemental analysis: calculated C 61.76, H 8.21, N 6.00; observed C 61.57, H 8.50, N 6.00.

Method II

Part A. A solution of 3-amino-2,4-bis(methylthio)-6 -methylpyridine (0.38 g, 1.88 mmol) and triethylamine (0.30 mL, 2.07 mmol) in tetrahydrofuran (8 mL) was cooled to 0° C., and treated with a solution of chloroacetyl chloride (0.18 mL, 2.26 mmol) in tetrahydrofuran (4 mL). After being stirred for 10 hours, the mixture was poured into water (100 mL), and this was extracted with ethyl acetate (2×100 mL). The extracts were combined, dried over anhydrous sodium sulfate, filtered and evaporated. The resulting solid was recrystallized to purity from ether, mp 190°–192° C., to afford N-[2,4-bis(methylthio)-6-methyl-pyridin-3-yl] -2-chloroacetamide (0.39 g, 1.41 mmol, 75%). $^1$H NMR (CDCl$_3$): δ 7.69 (1H, br s); 6.68 (1H, s); 4.26 (2H, s); 2.53 (3H, s); 2.51 (3H, s); 2.43 (3H, s). Mass spectrum (NH$_3$- CI/DDIP): m/z 279 (42%); 278 (17%); 277 (100%); 227 (4%).

Part B. Potassium carbonate (19.4 g, 140 mmol) was suspended in tetrahydrofuran (500 mL), and thiolacetic acid (10.0 mL, 140 mmol) was added dropwise. Then, a solution of 2-chloroacetophenone (16.6 g, 108 mmol) in tetrahydrofuran (100 mL) was added dropwise, and the mixture was allowed to stir for 10 hours. It was poured into water (700 mL), and the resulting mixture was extracted with ethyl acetate (700 mL), then methylene chloride (700 mL). The extracts were combined, dried over anhydrous magnesium sulfate, filtered and evaporated. The residual oil was purified by filtration through a short plug of silica gel (1:1 ethyl acetate-hexane) to afford phenacylthioacetate (20.0 g, 103 mmol, 96%) as an oil. $^1$H NMR (CDCl$_3$): δ 7.99 (2H, d, J= 8.4 Hz); 7.60 (1H, t, J= 7.7 Hz); 7.48 (2H, t, J= 8.1 Hz); 4.41 (2H, s); 2.41 (3H, s). Mass spectrum (NH$_3$ -CI/DDIP): m/z 212 (100%); 197 (2%); 196 (4%); 195 (19 %); 153 (1%).

Part C. A solution of the thioacetate from Part B above (8.70 g, 44.8 mmol) in ether (50 mL) was stirred vigorously while aqueous sodium hydroxide solution (50 mL, 2N, 100 mmol) was added. This mixture was stirred for 2 hours, then separated. The aqueous layer was cooled to 0° C. and acidified. This was extracted with methylene chloride (2×100 mL), and the extracts were combined, dried over anhydrous magnesium sulfate, filtered and evaporated. The residual liquid was distilled (110°–120° C., 1 mm Hg, bulb-to-bulb) to afford the pure product, 2-mercaptoacetophenone (6.00 g, 39.4 mmol, 88%). $^1$H NMR (CDCl$_3$ ): δ 7.97 (2H, dd, J= 8.2, 1.2 Hz); 7.63-7.57 (1H, m); 7.52-7.45 (2H, m); 3.97 (2H, d, J=7.3 Hz); 2.14 (1H, t, J=7.3 Hz). Mass spectrum (NH$_3$-CI/DDIP): m/z 172 (5%); 171 (10%); 170 (100%); 153 (20%); 138 (15%).

Part D. A solution of the chloride compound from Part A above (0.49 g, 1.77 mmol), 2-mercaptoacetophenone (0.49 g, 3.22 mmol), and potassium carbonate (0.27 g, 1.95 mmol) in tetrahydrofuran (20 mL) was heated to 50° C. for 6 hours. The mixture was then cooled, and poured into water (100 mL). This was extracted with methylene chloride (2×100 mL). The extracts were combined, dried over anhydrous sodium sulfate, filtered and evaporated. The resulting solid was recrystallized from ether (top 140°–142° C.) to afford pure N-[2,4 -bis(methylthio)-6-methylpyridin-3-yl]-2 -phenacylthioacetamide (0.433 g, 1.10 mmol, 62%). $^1$H NMR (CDCl$_3$): δ 8.11 (1H, br s); 8.02-7.96 (2H, m); 7.65-7.45 (3H, m); 6.66 (1H, s); 4.31 (2H, s); 3.46 (2H, s); 2.49 (3H, s); 2.48 (3H, s); 2.39 (3H, s). Mass spectrum (NH$_3$-CI/DDIP): m/z 395 (17%); 394 (25%); 393 (100%); 285 (1%); 275 (5%).

Part E. The standard photolysis procedure was employed for the sulfide from Part D (280 mg, 0.71 mmol) and E,E-6,8-tetradecadiene (1.11 g, 5.71 mmol) in 1:5 dimethylformamide-benzene solution. Evaporation and flash chromatography gave the title product, which was recrystallized to purity from ether (100 mg, 0.21 mmol, 30%), and which showed identical spectral characteristics to the sample prepared from Method I, above.

EXAMPLE 106

Preparation of N-[2,4-bis(methylthio)-6-methyl-3 -pyridyl] -2,3-dihydro-4,5-dimethyl-2H-pyran-2-carboxamide Part A. The method of Bonjouklian and Ruden, *J. Org. Chem.*, v. 42, p. 4095 (1977), was used here. Thus, a solution of diethylketomalonate (10.0 mL, 65.6 mmol) and 2,3-dimethyl-1,3-butadiene (16.3 mmol, 144 mmol) in acetonitrile (22 mL) was heated in a sealed tube at 140° C. for 6 hours. The contents of the tube was cooled, extracted with methylene chloride washing, evaporated and separated by flash chromatography (1:9 ethyl acetate-hexane) to afford diethyl 3,6-dihydro-4,5 -dimethyl-2H-pyran-2,2-dicarboxylate as an oil (13.6 g, 53.1 mmol, 81%). $^1$H NMR (CDCl$_3$): δ 4.26 (4H, q, J=7.0 Hz); 4.15 (2H, br s); 2.57 (2H, br s); 1.69 (3H, s); 1.51 (3H, s); 1.28 (6H, t, J=7.0 Hz). Mass spectrum (NH$_3$-CI/DDIP): m/z 275 (14%); 274 (100%); 257 (23%); 183 (1%).

Part B. A solution of the ester compound prepared in Part A above (9.63 g, 37.6 mmol) in tetrahydrofuran (150 mL) was treated with an aqueous solution of potassium hydroxide (150 mL, 10N, 1.5 mol), and stirred vigorously at ambient temperature for 48 hours. The solid salt was collected by filtration, and neutralized by dissolving into 1N aqueous hydrochloric acid (200 mL). This was extracted with ethyl acetate (2×200 mL), and the extracts were combined, dried over anhydrous sodium sulfate, filtered and evaporated to afford the product, 3,6-dihydro-4,5-dimethyl-2H-pyran- 2,2-dicarboxylic acid, as a waxy solid (7.46 g, 37.3 mmol, 99%). $^1$H NMR (CDCl$_3$): δ 4.16 (2H, br s); 2.57 (2H, br s); 1.68 (3H, br s); 1.51 (3H, br s). Mass spectrum (NH$_3$-CI/DDIP): no M+H$^+$ observed.

Part C. A solution of the diacid prepared in Part B above (7.46 g, 37.3 mmol) and morpholine (5.00 mL, 57.2 mmol) in pyridine (40 mL) was heated to reflux for 10 hours. The solution was cooled, and evaporated. The oily residue was partitioned between water and ethyl acetate (200 mL each). The ethyl acetate layer was washed with 1N aqueous hydrochloric acid (2×200 mL), then saturated brine (200 mL). The four aqueous layers were back extracted in sequence with ethyl acetate (200 mL). The organic extracts were combined, dried over anhydrous magnesium sulfate, filtered and evaporated to afford the product, 3,6-dihydro-4,5-dimethyl-2H-pyran-2 -carboxylic acid, as a solid, which was recrystallized to purity from ether-hexane, mp 82°–84° C. (3.32 g, 21.3 mmol, 57%). $^1$H NMR (CDCl$_3$): δ 10.45 (1H, br s); 4.24 (1H, dd, J=9.5, 4.8 Hz); 4.12 (2H, br s); 2.40-2.20 (2H, m); 1.69 (3H, br s); 1.55 (3H, br s). Mass spectrum (NH$_3$ -Cl/DDIP): m/z 175 (10%); 174 (100%).

Part D. A solution of the acid prepared in Part C above (1.57 g, 10.0 mmol) and dimethylformamide (2 drops) in benzene (20 mL) was treated dropwise with a solution of oxalyl chloride (3.00 mL, 34.4 mmol) in benzene (10 mL). The solution was stirred for 10 hours, then evaporated. The oily residue was taken up in tetrahydrofuran (5 mL), and added to an ice-cooled stirring solution of 3-amino- 2,4-bis(methylthio)-6-methylpyridine (950 mg, 4.74 mmol) and triethylamine (1.00 mL, 7.17 mmol) in tetrahydrofuran (20 mL). After being stirred for 12 hours, the mixture was poured into water (100 mL). This was extracted with ethyl acetate (2×100 mL), and the extracts were combined, dried over anhydrous sodium sulfate, filtered and evaporated to afford the title product as a solid, which was recrystallized to purity from ether, mp 149°–150° C. (1.27 g, 3.75 mmol, 79%). $^1$H NMR (CDCl$_3$): δ 7.78 (1H, br s); 6.66 (1H, s); 4.21 (1H, dd, J=9.9, 4.7 Hz); 4.17-4.09 (2H, m); 2.51 (3H, s); 2.49 (3H, s); 2.41 (3H, s); 2.40-2.30 (2H, m); 1.71 (3H, br s); 1.58 (3H, br s). $^{13}$C NMR (CDCl$_3$): δ 170.5, 156.8, 156.7, 148.6, 123.9, 123.5, 122.9, 113.7, 74.4, 69.8, 33.2, 24.4, 18.2, 14.0, 13.8, 12.8. IR (KBr): 3334, 2922, 1698, 1566, 1524, 1496, 1438, 1422, 1342, 1112, 810 cm$^{-1}$. Mass spectrum (NH$_3$-Cl/DDIP): m/z 341 (10%); 340 (19%); 339 (100%). Elemental analysis: calculated C 56.78, H 6.55, N 8.28; observed C 56.68, H 6.67, N 8.26.

Compounds 1–185 in Table 1 (below) can be prepared by the procedures described in Examples 70 and 106 employing the appropriately substituted starting materials.

EXAMPLE 186

Preparation of (Endo)-N-(2,6-diisopropylphenyl)-6 -isopropyl-3-methyl-1-thiabicyclo[2.2.2]oct-4-ene-2 -carboxamide Part A. A solution of 2,6-diisopropylaniline (10.0 mL, 53.0 mmol) and triethylamine (10.0 mL, 71.7 mmol) in tetrahydrofuran (100 mL) was cooled to 0° C., and treated dropwise with a solution of chloroacetyl chloride (5.00 mL, 62.8 mmol) in tetrahydrofuran (20 mL). After being stirred for 10 hours, the solution was poured into water (200 mL) and extracted with methylene chloride (2×200 mL). The extracts were combined, dried over anhydrous magnesium sulfate, filtered and evaporated to afford the product, N-(2, 6-diisopropylphenyl)-2-chloroacetamide, as a solid. The solid was purified by trituration in boiling ether, filtration and drying; mp 157°–158° C. (10.7 g, 42.0 mmol, 79%). $^1$H NMR (CDCl$_3$): δ 7.81 (1H, br s); 7.32 (1H, t, J=8.1 Hz); 7.19 (2H, d, J=8 Hz); 4.26 (2H, s); 3.02 (2H, heptet, J=6.6 Hz); 1.21 (12H, d, J= 6.6 Hz). Mass spectrum (NH$_3$-Cl/ DDIP): m/z 271 (100 %); 256 (11%); 255 (6%); 254 (30%); 219 (1%).

Part B. A solution of the chloride prepared in Part A above (4.30 g, 16.9 mmol), 2-mercaptoacetophenone (2.58 g, 16.9 mmol), and potassium carbonate (2.58 g, 18.7 mmol) in tetrahydrofuran (30 mL) was stirred at ambient temperature for 12 hours. The mixture was poured into water (120 mL), and this was extracted with methylene chloride (2×120 mL). The extracts were combined, dried over anhydrous magnesium sulfate, filtered and evaporated to afford the product, N-(2,6 -diisopropylphenyl)-2-phenacylthioacetamide, as a solid. The solid was purified by trituration in boiling ether, filtration and drying; mp 168°–169° C. (5.09 g, 13.8 mmol, 81%). $^1$H NMR (CDCl$_3$): δ 8.14 (1H, br s); 7.99 (2H, dd, J=8.0, 1.5 Hz); 7.63 (1H, tt, J=7.3, 1.1 Hz); 7.50 (2H, tt, J=7.3, 1.5 Hz); 7.30 (1H, dt, J=8.0, 1.4 Hz); 7.18 (2H, d, J=7.0 Hz); 4.15 (2H, s); 3.49 (2H, s); 3.07 (2H, heptet, J=6.6 Hz); 1.19 (12H, d, J=6.6 Hz). Mass spectrum (NH$_3$-CI/ DDIP): m/z 372 (8%); 371 (26%); 370 (100%); 336 (1%); 269 (2%).

Part C. The standard photolysis method was employed here. Thus, the sulfide prepared in Part B above (660 mg, 1.79 mmol) and α-terpinene (3.00 mL, 18.4 mmol) in 20 mL benzene solution were photolyzed as described previously. Chromatography (1:19 ethyl acetate-hexane) gave first the exo isomer of cycloadduct (30 mg, 78 mmol, 4%), then acetophenone (a byproduct), then the title product (300 mg, 0.78 mmol, 43%) as a solid, mp 177°–178° C. $^1$H NMR (CDCl$_3$): δ 7.60 (1H, br s); 7.26 (1H, t, J=8.0 Hz); 7.15 (2H, d, J=8.0 Hz); 6.55 (1H, d, J= 8.8 Hz); 6.01 (1H, d, 8.8 Hz); 3.89 (1H, s); 2.99 (2H, heptet, J=6.6 Hz); 2.17-2.03 (2H, m); 1.80-1.60 (2H, m); 1.56 (3H, s); 1.47-1.37 (1H, m); 1.17 (12H, d, J= 6.6 Hz); 1.13 (3H, d, J=7.0 Hz); 1.12 (3H, d, J=7.0 Hz). $^{13}$C NMR (CDCl$_3$): δ 170.3, 145.9, 136.7, 135.5, 131.6, 128.2, 123.4, 59.2, 38.0, 34.8, 33.8, 33.5, 28.7, 24.8, 23.7, 19.0, 18.8. IR (KBr): 3276, 2960, 2870, 1660, 1512, 1464, 730 cm$^{-1}$. Mass spectrum (NH$_3$ -Cl/DDIP): m/z 388 (9%); 387 (29%); 386 (100%); 269 (2 %); 252 (2%). Elemental analysis: calculated C 74.76, H 9.15, N 3.63; observed C 74.54, H 9.24, N 3.26.

Compounds 186–296 in Table 2 (below) can be prepared by the procedures described in Example 186 employing the appropriately substituted starting materials.

EXAMPLE 314

Preparation of N-[2,4-bis(methylthio)-6-methylpyridin-3 -yl]-3,6-diheptyl-3,4,5,6-tetrahydro-2H-thiopyran-2 -carboxamide (Proposed)

A solution of the compound from Example 164 is dissolved in methanol (ca. 0.3M), and treated with dipotassium diazo-dicarboxylate (10 eq.). To this is added a 1:1 methanol solution of acetic acid (10 eq.) over 4 hours by syringe pump at 20° C. After addition is complete, the reaction mixture is evaporated, and the residue is taken up in methylene chloride and washed 2 times with 1 N sodium hydroxide. The solution is then dried over anhydrous sodium sulfate, filtered and evaporated, and the residue is separated by flash chromatography to afford the title product.

EXAMPLE 402

Preparation of N-[2,4-bis(methylthio)-6-methylpyridin-3 -yl]-6-hexylthio-2,3,5,6-tetrahydro-4H-thiopyran-4-one-2 -carboxamide Part A. A solution of the sulfide from Example 70, Method II, Part D above (0.60 g, 1.53 mmol) and 1 -methoxy-3-trimethylsiloxybutadiene (1.00 g, 5.80 mmol) in 4:1 benzene-dimethylformamide (25 mL) was subjected to sunlamp photolysis as described in Example 70 above. The reaction mixture was evaporated, diluted with tetrahydrofuran (50 mL) and treated with 1N hydrochloric acid (5 mL). This mixture was allowed to stir for 3 hours, then poured into water (200 mL) and extracted with ethyl acetate (2×200 mL). The extracts were combined, dried over anhydrous sodium sulfate, filtered and evaporated. The residue was separated by column chromatography (1:1 ethyl acetate-hexane) to afford the product, N-[2,4-bis(methylthio)-6 -methylpyridin-3-yl]-2,3-dihydro-2H-thiopyran-4-one-2 -carboxamide, as a semisolid material (0.52 g, 1.53 mmol, 100%). $^1$H NMR (CDCl$_3$): δ 7.42 (1H, br s); 7.40 (1H, d, J=10.2 Hz); 6.64 (1H, s); 6.28 (1H, d, J=10.2 Hz); 4.32 (1H, dd, J=8.2, 4.2 Hz); 3.31 (1H, dd, J=16.8, 8.2 Hz); 3.02 (1H, dd, J=16.8, 4.2 Hz); 2.51 (3H, s); 2.49 (3H, s); 2.40 (3H, s). Mass spectrum (NH³-Cl/DDIP): m/z 343 (16%); 342 (19%); 341 (100%); 227 (14%).

Part B. The enone from Part A above (0.52 g, 1.53 mmol) was dissolved in tetrahydrofuran (10 mL), and treated with hexanethiol (0.26 mL, 1.83 mmol) and p-toluenesulfonic acid (0.29 g, 1.53 mmol). The mixture was stirred at ambient temperature for 72 hours, then at reflux for 24 hours. The mixture was cooled, and poured into water (100 mL). This was extracted with methylene chloride (2×100 mL), and the extracts were combined, dried over anhydrous sodium sulfate, filtered and evaporated. The residue was separated by column chromatography (1:1 ethyl acetate-hexane) to afford first, the title product, then unreacted starting material. The product was purified by recrystallization in ether, mp 175°–177° C. $^1$H NMR (CDCl$_3$): δ 7.20 (1H, br s); 6.55 (1H, s); 4.48 (1H, dd, J=9.9, 3.6 Hz); 4.00 (1H, t, J=4.9 Hz); 3.02 (1H, t, J=4.2 Hz); 2.97 (1H, t, J=4.2 Hz); 2.72-2.38 (4H, m); 2.43 (3H, s); 2.41 (3H, s); 2.33 (3H, s); 1.60-1.47 (2H, m); 1.39 -1.18 (6H, m); 0.81 (3H, t, J=6.9 Hz). IR (KBr): 3454, 3222, 2924, 1710, 1650, 1564, 1514, 1440, 1180, 806 cm$^{-1}$. Mass spectrum (NH$_3$-Cl/DDIP): m/z 461 (20%); 460 (25 %); 459 (100%); 425 (25%); 341 (85%). Elemental analysis: calculated C 52.37, H 6.59, N 6.11; observed C 52.89, H 6.73, N 5.92.

EXAMPLE 426

Preparation of (2S,3R,4S,5R,6S)-N-[2,4-bis(methylthio)-6-methylpyridin-3-yl]-3-benzyloxy-4,5-dibutoxy-6 -methoxy-3,4,5,6-tetrahydro-2H-pyran-2-carboxamide Part A. To a stirred solution of (4,6-O-benzylidene) methyl-α-D-glucopyranoside (20 g) in dry tetrahydrofuran (200 ml) and anhydrous N,N-dimethylformamide (50 ml) was added 60% sodium hydride in oil (7.4 g), and the mixture was stirred for an hour at room temperature. Then iodobutane (21 ml) was added and the mixture was refluxed for 1.5 hours. It was cooled to room temperature and were added additional 60% sodium hydride in oil (3.7 g) and iodobutane (10.5 ml). The mixture was continued to stir for additional 45 minutes and cooled to room temperature. After slow addition of water (200 ml), it was extracted with ethyl acetate twice. The combined extracts were washed with water and brine, dried (magnesium sulfate), and evaporated to give an oily residue of a mixture of the mono-butylated product and the di-butylated product. The desired dibutoxy-glucopyranoside was separated by column chromatography on silica gel with elution by 1:9 ethyl acetate—hexane. Rf=0.79 (6:4 ethyl acetate—hexane)

Part B. To a stirred solution of the dibutoxy-glucopyranoside from Part A above (2.63 g) in anhydrous ethyl ether (26 ml) and dry methylene chloride (26 ml) was added lithium aluminum hydride (0.88 g). Then a solution of aluminum chloride (2.63 g) in anhydrous ethyl ether (26 ml) was also added dropwise over a period of 30 minutes. The mixture was continued to stir for 2 hours at room temperature, and the excess lithium aluminum hydride was destroyed by slow addition of ethyl acetate (10 ml) after cooling to 0°. About 10 ml of water was added with stirring and the resulting precipitates were removed by filtration through Celite®. The filtrate was washed with water and brine, dried (sodium sulfate), and evaporated to give a mixture (about 10:1) of 4-O-benzyl-glucopyranoside and 6-O-benzyl-glucopyranoside as a clear oil. The desired 4-O-benzyl-glucopyranoside was separated by column chromatography on silica gel with elution by 2:8 ethyl acetate—hexane followed by 3:7 ethyl acetate—hexane. Rf=0.08 (2:8 ethyl acetate—hexane)

Part C. To a stirred solution of oxalyl chloride (0.45 ml) in dry methylene chloride (25 ml) at −40° was added dimethylsulfoxide (0.4 ml) dropwise and the mixture was stirred for 10 minutes. Then a solution of the 4-O-benzyl-glucopyranoside from Part B above (1.37 g) in dry methylene chloride (25 ml) was added dropwise and the mixture was stirred for 20 minutes at −40°. Finally triethylamine (1.5 ml) was added and the mixture was stirred for 1 hour while gradually raising the temperature to 0°. At the end of the stirring the mixture was added to ethyl ether and the solution was washed with water and brine. It was dried (magnesium sulfate) and evaporated to give an oily residue of the aldehyde.

Part D. To a stirred solution of the aldehyde from Part C above (1.12 g) in t-butanol (50 ml) and water (12.5 ml) were added sodium chlorite (0.42 g) and sulfamic acid (0.45 g) and the mixture was stirred for 1 hour. After addition of water, it was extracted with methylene chloride twice. The combined extracts were washed with water and brine, dried (magnesium sulfate), and evaporated to give a syrupy residue of the acid. The acid was purified by column chromatography on silica gel with elution by 1:9 methanol—methylene chloride.

Part E. To a stirred solution of the carboxylic acid from Part D above (0.83 g) and N-methylmorpholine (0.44 ml) in dry methylene chloride (10 ml) at 0° was added isobutyl chloroformate (0.29 ml) and the mixture was stirred for 25 minutes at the same temperature. Then a solution of 3-amino-2,4-bis(methylthio)-6-methylpyridine (0.445 g) in dry methylene chloride (3 ml) was added to the mixture, and it was stirred for 2.5 hours at room temperature. After addition of ethyl acetate, the solution was washed with water and brine, dried (magnesium sulfate), and evaporated to give an oily residue. The crude product was purified by column chromatography on silica gel with elution by 2:8 ethyl acetate—hexane to give pure title product as a solid. Rf=0.36 (3:7 ethyl acetate—hexane). $^1$H NMR (300 MHz, CDCl$_3$): δ 7.52 (1H, s); 7.41 (2H, d, J=6.2 Hz); 7.29-7.21 (3H, m); 6.65 (1H, s); 4.92 (1H, d, J=9.9 Hz, A of AB); 4.92 (1H, d, J=3.7 Hz); 4.74 (1H, d, J= 9.9 Hz, B of AB); 4.30-4.27 (1H, m); 3.87-3.72 (4H, m); 3.64 (2H, t, J=6.8 Hz); 3.47 (3H, s); 3.41-3.36 (1H, m); 2.48 (6H, s); 2.37 (3H, s); 1.64-1.53 (4H, m); 1.42 -1.33 (4H, m); 0.92 (3H, t, J=7.32 Hz); 0.90 (3H, t, J= 7.32 Hz).

EXAMPLE 434

Preparation of (2S,3R,4S,5R,6S)-N-[2,4-bis(methylthio)-6-methylpyridin-3-yl]-6-methoxy-3,4,5-tributoxy-3,4,5,6 -tetrahydro-2H-pyran-2-carboxamide Part A. To a stirred solution of (6-O-triphenylmethyl)methyl-α -D-glucopyranoside (15 g) in dry tetrahydrofuran (100 ml) and N,N-dimethylformamide (25 ml) was added 60% sodium hydride in oil (5.36 g) and the mixture was stirred for 2 hours at 60°. Then iodobutane (15.9 ml) was added, and the mixture was stirred in a 100° oil bath for 24 hours. After cooling, water (about 100 ml) was added slowly and it was extracted with ethyl acetate twice. The combined extracts were washed with water and brine, dried (MgSO$_4$) and evaporated to give a syrupy residue. It was purified by column chromatography on silica gel with elution by 1:9 ethyl acetate—hexane to afford pure (2,3,4-tri-O-butyl-6-O-triphenylmethyl)methyl-α -D-glucopyranoside as a white solid.

Part B. To a stirred solution of (2,3,4-tri-O-butyl-6 -O-triphenylmethyl)methyl-α-D-glucopyranoside from Part A above (2.4 g) in chloroform (10 ml) was added 70% aqueous acetic acid and the mixture was stirred for 5 hours in a 60° oil bath. At the end of the stirring, the solvent, acid and water were removed by evaporation to give a solid residue. It was purified by column chromatography on silica gel with elution by 1:9 ethyl acetate—hexane followed by 2:8 ethyl acetate—hexane to give (2,3,4-tri-O-butyl)methyl-α-D-glucopyranoside (1.25 g) as a viscous oil.

Part C. To a stirred solution of oxalyl chloride (0.41 ml) in dry methylene chloride (25 ml) at −40° was added dimethylsulfoxide (0.35 ml) dropwise and the mixture was stirred for 10 minutes. Then a solution of the (2,3,4 -O-tributyl)methyl-α-D-glucopyranoside from Part B above (1.13 g) in dry methylene chloride (25 ml) was added dropwise and the mixture was stirred for 20 minutes at −40°. Finally triethylamine (1.35 ml) was added and the mixture was stirred for 1 hour while gradually raising the temperature to 0°. At the end of the stirring the mixture was added to ethyl ether and the solution was washed with water and brine. It was dried (magnesium sulfate) and evaporated to give an oily residue of the aldehyde. The residue was dissolved in t-butanol (50 ml) and water (12.5 ml) and were added sodium chlorite (0.42 g) and sulfamic acid (0.45 g). After stirring for 1 hour was added water, and it was extracted with methyle chloride twice. The combined extracts were washed with water and brine, dried ($MgSO_4$), and evaporated to give a syrupy residue of α-1-O-methyl- 2,3,4-tri-O-butyl-D-glucuronic acid. The acid was purified by column chromatography on silica gel with elution by 1:9 methanol—methylene chloride.

Part D. To a stirred solution of α-1-O-methyl-2,3,4 -tri-O-butyl-D-glucuronic acid from Part C above (0.1 g), triethylamine (0.11 ml) and N,N-dimethylformamide (0.01 ml) in dry methylene chloride (2 ml) at 0° was added oxalyl chloride (0.06 ml), and the mixture was stirred for 16 hours while raising the temperature gradually to 20°. All the volatile material was evaporated off and dried in vacuo to give a solid residue. The residue was redissolved in dry methylene chloride (3 ml), and to the solution were added triethylamine (0.11 ml) and 3-amino- 2,4-dimethylthio-6-methyl-pyridine (0.054 g) at 0°. The mixture was stirred at 0°~20° for 16 hours and was partitioned between ethyl acetate and water. The organic layer was washed with water and brine, dried (magnesium sulfate) and evaporated to give an oily residue, which upon column chromatography on silica gel with elution by 3:7 ethyl acetate—hexane afforded a pure sample of the title product as a solid. Rf=0.014 (3:7 ethyl acetate—hexane). $^1$H NMR (300 MHz, $CDCl_3$): δ 7.49 (1H, s); 6.64 (1H, s); 4.88 (1H, d, J=3.3 Hz); 4.18 (1H, d, J=9.89 Hz); 3.83-3.70 (4H, m); 3.68-3.60 (3H, m); 3.51 (1H, d, J=9.89 Hz); 3.46 (3H, s); 3.33 (1H, dd, J=10.7, 3.48 Hz); 2.49 (3H, s); 2.47 (3H, s); 2.39 (3H, s); 1.62-1.49 (6H, m); 0.91 (6H, t, J=7.32 Hz); 0.85 (3H, t, J=7.32 Hz).

EXAMPLE 442

Preparation of (2S,3R,4S,5R)-N-[2,4-bis(methylthio)-6-methylpyridin-3-yl]-3-benzyloxy-4,5-dibutoxy-3,4,5,6-tetrahydro-2H-pyran-2-carboxamide Part A. To a stirred solution of the 4-O-benzyl-glucopyranoside from Example 426, Part B (2 g) in dry methylene chloride (50 ml) were added triethylsilane (2.42 ml) and boron trifluoride etherate (1.55 ml) and the mixture was refluxed for 3 days. After cooling was added saturated aqueous sodium bicarbonate to quench the reaction. The product was extracted with methylene chloride, and the organic solution was washed with water, dried (magnesium sulfate) and evaporated to give an oily residue. It was purified by column chromatography on silica gel with elution by 2:8 ethyl acetate—hexane to give the 4-O-benzyl-1-deoxy-2,3-di-O-butyl-D-glucopyranose.
Rf=0.35 (4:6 ethyl acetate—hexane)

Part B. To a stirred solution of 4-O-benzyl-1-deoxy-2,3-di-O-butyl-D-glucopyranose from Part A above (0.93 g) in dry methylene chloride (10 ml) were added pyridinium chlorochromate (1.1 g) and powdered molecular sieves 4A (1.1 g), and the mixture was stirred for 2 hours at room temperature. At the end of the stirring was added ethyl ether (about 20 ml), and the mixture was filtered through Celite®. The filtrate was evaporated to give an oily residue of the crude aldehyde.

Part C. The aldehyde from Part B above was converted to the title compound by the same method described for the conversion of the compound of Example 426, Part D to the compound of Example 426. The product was purified by column chromatography on silica gel with elution by 2:8 ethyl acetate—hexane to give pure N-[2,4 -bis(methylthio)-6-methylpyridin-3-yl] 1-deoxy-2,3-di-O-butyl- 4-O-benzyl-D-glucuronamide as a solid. Rf=0.17 (2:8 ethyl acetate—hexane). $^1$H NMR (300 MHz, $CDCl_3$): δ 7.53 (1H, s); 7.41 (1H, d, J=6.59 Hz); 7.30 (1H, s); 7.30-7.20 (3H, m); 6.64 (1H, s); 4.91 (1H, d, J=9,89 Hz, A of AB); 4.72 (1H, d, J=9.89 Hz, B of AB); 4.13 (1H, dd, J=10.99, 4.03 Hz); 3.93 (1H, d, J=9.52 Hz); 3.82-3.77 (2H; m); 3.72 (1H, t, J=8.72 Hz); 3.64-3.59 (2H, m); 3.44-3.37 (2H, m); 3.23 (1H, t, J=10.43 Hz); 2.48 (6H, s); 2.37 (3H, s); 1.64-1.45 (4H, m); 1.43-1.31 (4H, m); 0.92 (3H, t, J=7.32 Hz); 0.91 (3H, t, J= 7.32 Hz).

EXAMPLE 458

Preparation of (2S,3R,4S,5R)-N-[2,4-bis(methylthio)-6 -methylpyridin-3-yl]-3,4,5-tributoxy-3,4,5,6-tetrahydro-2H-pyran-2-carboxamide Part A. To a solution of α-1-O-methyl-2,3,4-tri-O-butyl-D-glucuronic acid from Example 434, Part C (0.34 g) in methanol (5 ml) was added concentrated sulfuric acid (0.5 ml), and the mixture was refluxed for 16 hours. After cooling it was neutralized with saturated sodium bicarbonate and extracted with ethyl acetate twice. The combined extracts were washed with water and brine, dried (magnesium sulfate), and evaporated to give an oily residue of methyl α-1-O-methyl-2,3,4-tri-O-butyl-D-glucuronate (0.29 g).

Part B. To a stirred solution of the methyl α-1-O-methyl-2,3,4-tri-O-butyl-D-glucuronate prepared in Part A above (0.29 g) in dry benzene (5 ml) were added triethylsilane (0.36 ml) and boron trifluoride etherate (0.27 ml) and the mixture was refluxed for 2 hours. After cooling was added saturated sodium bicarbonate to quench the reaction. The product was extracted with ethyl acetate, and the organic solution was washed with water, dried (magnesium sulfate) and evaporated to give an oily residue. It was purified by column chromatography on silica gel with elution by 1:9 ethyl acetate—hexane to give methyl 1-deoxy-2,3,4-tri-O-butyl-D-glucuronate (0.25 g).

Part C. To a stirred solution of methyl 1-deoxy-2,3,4 -tri-O-butyl-D-glucuronate from Part B above (0.25 g) and 3-amino-2,4-bis(methylthio)-6-methylpyridine (0.15 g) in dry dichloroethane (5 ml) was added 2.0M solution of trimethyl aluminium in toluene (0.75 ml) dropwise and the mixture was refluxed for 3 hours. After cooling, ethyl acetate was added and the solution was washed with 1N hydrochloric acid, saturated sodium bicarbonate and brine. The organic solution was dried (magnesium sulfate) and evaporated to give a solid residue. The crude product was purified by column chromatography on silica gel with elution by 2:8 ethyl acetate—hexane to give a crystalline solid of the desired title product. $R_f$=0.24 (3:7 ethyl acetate—hexane). $^1$H NMR (300 MHz, CDCl$_3$): δ 7.52 (1H, s); 6.65 (1H, s); 4.12 (1H, dd, J=11.17, 4.94 Hz); 3.83-3.67 (4H, m); 3.64-3.54 (2H, m); 3.49 (1H, t, J=4.63 Hz); 3.46-3.18 (3H, m); 2.50 (3H, s); 2.48 (3H, s); 2.40 (3H, s); 1.65-1.50 (6H, m), 1.47-1.25 (6H, m), 0.96-0.84 (9H, m).

Compounds 297–471 in Table 3 (below) can be prepared by the procedures described in Examples 314, 402, 426, 434, 442 and 458 employing the appropriately substituted starting materials.

EXAMPLE 476

N-[2,4-bis(methylthio)-6-methylpyridin-3-yl]-4,5 -diheptyl-2,3,4,5-tetrahydrothiophene-2-carboxamide The title compound is expected to be prepared using the methods described below.

Part A. A solution of 2-heptyl-1,3-decanediol (prepared by aldol self-condensation of octanol, followed by sodium borohydride reduction) and carbon tetrabromide (1.3 eq.) in methylene chloride is cooled to 0° C., and a solution of triphenylphosphine (1.3 eq.) is added dropwise with stirring overnight. The reaction mixture is evaporated, and the residue is separated by flash chromatography to afford 1,3-dibromo-2-heptyldecane.

Part B. The method described by Ikegami et al., *Tetrahedron*, v. 30, p. 2087 (1974), is used here. Thus, a solution of sodium ethoxide in ethanol (prepared from metallic sodium and ethanol) is treated with diethylmalonate. After 1.5 hours at reflux temperature, the solution of sodiomalonate is cooled and added to an ethanolic solution of the bromide prepared in Part A above. The resulting solution is heated to reflux for 2 hours, then cooled. Workup as described in the listed reference then affords diethyl 1-(3-bromo-2 -heptyldecyl)malonate.

Part C. The method described by Ikegami et al., *Tetrahedron*, v. 30, p. 2087 (1974), is used here. Thus, a solution of the diester prepared in Part B above in ether is treated with bromine at 0° C. Workup as described in the listed reference then affords diethyl 1-bromo-1-(3-bromo-2-heptyldecyl)malonate.

Part D. The method described by Ikegami et al., *Tetrahedron*, v. 30, p. 2087 (1974), is used here. Thus, an ethanolic solution of the dibromide prepared in Part C above is treated with an ethanolic suspension of sodium sulfide at 0° C. for 2 hours. After workup as described in the listed reference, diethyl 4,5-diheptyl- 2,3,4,5-tetrahydrothiophene-2,2-dicarboxylate is obtained.

Part E. The method described by Ikegami et al., *Tetrahedron*, v. 30, p. 2087 (1974), is used here. Thus, an ethanolic solution of the diester prepared in Part D above is treated with sodium hydroxide. After refluxing for 1 hour, the solution is evaporated, acidified, and extracted with ether 3 times. The ether extracts are combined, dried over anhydrous magnesium sulfate, filtered and evaporated. The residue (containing 4,5 -diheptyl-2,3,4,5-tetrahydrothiophene-2,2-dicarboxylic acid) is subjected to heating (140° C.) to afford, upon workup, 4,5-diheptyl-2,3,4,5-tetrahydrothiophene-2 -carboxylic acid.

Part F. A solution of the acid prepared in Part E above and catalytic dimethylformamide in benzene is treated with a solution of oxalyl chloride (3 eq.) in benzene with stirring at room temperature. After at least 6 hours, the solution is evaporated, and the residue is taken up in tetrahydrofuran. This solution is added to a tetrahydro-furan solution of 3-amino-2,4 -bis(methylthio)-6-methyl-pyridine (1 eq. ) and triethylamine (1.1 eq.) at 0° C. After stirring for at least 4 hours, the solution is poured into 4 volumes of water. This mixture is extracted 2 times with equal volumes of ethyl acetate. The extracts are washed with saturated brine, combined, dried over anhydrous sodium sulfate, filtered and evaporated. The residue is purified by either flash chromatography or recrystallization to afford the title product.

EXAMPLE 540

N-[2,4-bis(methylthio)-6-methylpyridin-3-yl]-3,5 -diheptyl-2,3,4,5-tetrahydrothiophene-2-carboxamide The title compound is expected to be synthesized using the procedures described below.

Part A. 1-Bromo-1-octene is added slowly to an ether suspension of magnesium turnings. The mixture is heated under mild reflux until the magnesium is consumed. The solution is cooled to 0° C. and an ether solution of 1 -heptyloxirane is added. The mixture is stirred until the reaction is complete, then is poured over ice and acidified with 1N sulfuric acid. The layers are separated, and the organic layer is dried over magnesium sulfate, filtered and evaporated to afford 7-heptadecen-10-ol.

Part B. The method of Speckamp et al., *Tetrahedron Letters*, v. 32, p. 1491 (1991), is employed here. Thus, a solution of ethyl 2-chloro-2-(phenylthio)acetate [prepared according to the method of Böhme et al., *Liebigs Annalen der Chemie*, p. 51 (1977)], 7-heptadecen- 10-ol, and catalytic zinc acetate dihydrate in benzene is heated to reflux under a Dean-Stark trap until the formation of hydrogen chloride is complete. Workup according to the listed reference affords ethyl 2-(1 -heptyl-3-decen-1-oxy)-2-(phenylthio)acetate.

Part C. The method of Speckamp et al., *Tetrahedron Letters*, v. 32, p. 1491 (1991), is employed here. Thus, a 0.07M benzene solution of the precursor prepared in Part B above is heated to reflux, and treated with a 0.1 M benzene solution of tri-n-butyltin hydride (1.5 eq.) and 2,2'-azobisisobutyronirile (catalytic) delivered over 6 hours by syringe pump. After the addition is complete, the solution is cooled and evaporated. The residue is separated by flash chromatography to afford ethyl 3,5-diheptyl-2,3,4,5-tetrahydrofuran-2 -carboxylate.

Part D. A solution of the ester prepared in Part C above is stirred for 12 hours at ambient temperature in ethanolic sodium hydroxide (0.25M, 2 eq.). The solution is evaporated, and the residue acidified with 1 N hydrochloric acid. This is extracted with 2 equal volumes of ethyl acetate, and the extracts are washed with brine, combined, dried over anhydrous magnesium sulfate, filtered and evaporated to afford 3,5-diheptyl- 2,3,4,5-tetrahydrofuran-2-carboxylic acid.

Part E. A solution of the acid prepared in Part D above and catalytic dimethylformamide in benzene is treated with a solution of oxalyl chloride (3 eq.) in benzene with stirring at room temperature. After at least 6 hours, the solution is evaporated, and the residue is taken up in tetrahydrofuran. This solution is added to a tetrahydro-furan solution of 3-amino-2,4 -bis(methylthio)-6-methyl-pyridine (1 eq.) and triethylamine (1.1 eq.) at 0° C. After stirring for at least 4 hours, the solution is poured into 4 volumes of water. This mixture is extracted 2 times with equal volumes of ethyl acetate. The extracts are washed with saturated brine, combined, dried over anhydrous sodium sulfate, filtered and evaporated. The residue is purified by either flash chromatography or recrystallization to afford the title product.

EXAMPLE 577

Preparation of (2S,3R,4R,5R)-N-[2,4-bis(methylthio)-6-methylpyridin-3-yl]-3,4-dibutoxy-5-methoxy-2,3,4,5-tetrahydrofuran-2-carboxamide and (2S,3R,4R,5S)-N-[2,4-bis(methylthio)-6-methylpyridin-3-yl]-3,4-dibutoxy-5-methoxy-2,3,4,5-tetrahydrofuran-2-carboxamide Part A. To a stirred suspension of sodium hydride (8 g, 60% in oil, washed with hexane) in dry tetrahydrofuran (200 ml) and anhydrous N,N-dimethylformamide (50 ml) was added 1,2;5,6-di-O-isopropylidene-D-glucofuranose (26.03 g) portionwise and the mixture was stirred for 30 minutes at room temperature. Then iodobutane (22.8 ml) was added slowly and the mixture was stirred at 60° for 18 hours. After cooling to room temperature it was poured into ice water and the product was extracted with ethyl acetate. The organic solution was washed with brine, dried over anhydrous magnesium sulfate and evaporated to give a syrupy residue of 3-butyl-1,2;5,6-di-O-isopropylidene-D-glucofuranose.

Part B. The 3-butyl-glucofuranose from Part A above (20 g) was dissolved in 70% aqueous acetic acid (250 ml) and the solution was stirred for 16 hours at room temperature. After addition of water (about 500 ml), it was extracted with methylene chloride twice and the combined extracts were washed with water, saturated aqueous sodium bicarbonate and brine. The solution was dried (magnesium sulfate) and evaporated to give a syrupy residue of 3-butyl-1,2-O-isopropylidene-D-glucofuranose.

Part C. To a stirred solution of the diol from Part B above (9.9 g) in methanol (200 ml) at 0° was added an aqueous solution of sodium periodate (11.5 g in 50 ml of water) dropwise and the mixture was stirred for 1.5 hours at 0°–20°. The solution was filtered through Celite® and evaporated under reduced pressure. The residue was then filtered through a plug of silica gel with elution by ethyl acetate. Evaporation of the solvent gave the desired aldehyde.

Part D. To a stirred solution of the aldehyde from Part C above (2.2 g) in t-butanol (80 ml) and water (20 ml) at 0° were added sodium chlorite (1.24 g) and sulfamic acid (1.32 g) and the mixture was stirred for 1 hour. After addition of water, it was extracted with methlene chloride twice. The combined extracts were washed with water and brine, dried (magnesium sulfate), and evaporated to give a syrupy residue of the acid.

Part E. To a stirred solution of the carboxylic acid from Part D above (8 g) in methanol (200 ml) was added concentrated sulfuric acid dropwise and the mixture was refluxed for 3 hours. After cooling, it was neutralized with saturated sodium carbonate, and was extracted with ethyl acetate twice. The combined extracts were washed with water and brine, dried (magnesium sulfate) and evaporated to give 6.7 g of syrupy residue of the hydroxy-ester.

Part F. To a stirred solution of the hydroxy-ester from Part E above (2.2 g) in dry tetrahydrofuran (50 ml) and dry N,N-dimethylformamide (12.5 ml) was added 60% sodium hydride in oil (0.53 g) and the mixture was continued to stir for 1 hour. Then iodobutane (1.5 ml) was added, and the mixture was stirred for 18 hours at room temperature. After addition of water, it was extracted with ethyl acetate twice. The combined extracts were washed with water and brine, dried (magnesium sulfate) and evaporated to give a mixture of α and β isomers of the dibutoxy-ester.

Part G. To a stirred solution of the dibutoxy-esters from Part F above (0.54 g) and 3-amino-2,4-dimethylthio- 6-methyl-pyridine (0.43 g) in dry methylene chloride (10 ml) was added 2.0M solution of trimethyl aluminium in toluene (1.15 ml) dropwise and the mixture was refluxed for 18 hours.

After cooling, ethyl acetate was added and the solution was washed with 1N hydrochloric acid, saturated sodium bicarbonate and brine. The organic solution was dried (magnesium sulfate) and evaporated to give a solid residue. The crude product was purified by column chromatography on silica gel with elution by 2:8 ethyl acetate—hexane to give crystalline solids of α and β-methoxy amides.

α Isomer

Rf=0.2 (3:7 ethyl acetate—hexane)

$^1$H NMR (300 MHz, CDCl$_3$): δ 7.72 (1H, s); 6.65 (1H, s); 5.17 (1H, d, J=4.03 Hz); 4.83 (1H, d, J=5.86 Hz); 4.24 (1H, dd, J=5.86, 4.03 Hz); 3.95 (1H, t, J=3.85 Hz); 3.75-3.47 (4H, m); 3.52 (3H, s); 2.49 (3H, s); 2.47 (3H, s); 2.39 (3H, s); 1.66-1.43 (4H, m); 1.42-1.26 (4H, m); 0.92 (3H, t, J=7.32 Hz); 0.86 (3H, t, J=7.32 Hz).

β Isomer

Rf=0.15 (3:7 ethyl acetate—hexane)

$^1$H NMR (300 MHz, CDCl$_3$): δ 7.70 (1H, s); 6.63 (1H, s); 4.99 (1H, d, J=4.39 Hz); 4.41 (1H, d, J=5.86 Hz); 4.34 (1H, t, J=6.41 Hz); 3.94-3.81 (2H, m); 3.63-3.50 (3H, m); 3.59 (3H, s); 2.49 (3H, s); 2.47 (3H, s); 2.38 (3H, s); 1.66-1.50 (4H, m); 0.91 (3H, t, J=7.32 Hz); 0.88 (3H, t, J=7.32 Hz).

Compounds 472–598 in Table 4 (below) can be prepared by the procedures described in Examples 476, 540 and 577 employing the appropriately substituted starting materials.

EXAMPLE 599

Preparation of 1-(2,6-diisopropylphenyl)-3-(4,5-dipentyl-3,6-dihydro-2H-thiopyran-2-yl)-urea Part A. The standard photolysis procedure was employed here. Thus, a solution of the sulfide from Example 70, Method I, Part A (2.80 g, 11.7 mmol) and 2,3-dipentyl-1,3-butadiene (prepared according to the method of Butsugan, et al., *Synthesis*, p. 963 (1985); 6.85 g, 35.2 mmol) in benzene (60 mL) was irradiated for 7 hours at which time the contents of the flasks were combined and evaporated. The oily residue was separated by flask chromatography (3:97 ethyl acetate-hexane) to afford the product, ethyl 4,5-dipentyl-2,3-dihydro-2H-thiopyran-2-carboxylate, as an oil (3.22 g, 10.3 mmol, 88%). $^1$H NMR (CDCl$_3$): δ 4.19 (2H, q, J=7.3 Hz); 3.59 (1H, t, J= 6.6 Hz); 3.12 (2H, br s); 2.47 (2H, d, J=6.6 Hz); 2.11-1.99 (4H, m); 1.42-1.20 (12H, m); 0.89 (6H, t, J= 6.8 Hz). Mass spectrum (NH$_3$-CI/DDIP): m/z 330 (26%); 314 (22%); 313 (100%); 265 (1%); 239 (1%).

Part B. A solution of the ester compound from Part A above (1.11 g, 3.55 mmol) and sodium hydroxide (0.25N solution) in 95% ethanol (28 mL, 7.00 mmol NaOH) was stirred for 12 hours at ambient temperature. The reaction mixture was evaporated, and the residue acidified with hydrochloric acid (1N, 100 mL). This was saturated with sodium chloride and extracted with methylene chloride (2×120 mL). The extracts were combined, dried over anhydrous magnesium sulfate, filtered and evaporated to afford the product, 4,5-dipentyl-2,3-dihydro-2H-thiopyran-2-carboxylic acid, as an oil (0.97 g, 3.41 mmol, 96%). $^1$H NMR (CDCl$_3$): δ 3.65 (1H, t, J=5.5 Hz); 3.16 (1H, d, J=16.1 Hz); 3.07 (1H, d, J=16.1 Hz); 2.50 (2H, d, J=5.8 Hz); 2.10 -2.01 (4H, m); 1.42-1.20 (12H, m); 0.89 (6H, t, J=6.6 Hz). Mass spectrum (NH$_3$-CI/DDIP): m/z 302 (100%); 286 (14%); 285 (75%); 225 (2%); 195 (1%).

Part C. A solution of the acid prepared in Part B above (1.00 g, 3.52 mmol) in toluene (10 mL) was treated with diisopropylethylamine (0.61 mL, 3.52 mmol), and stirred at ambient temperature for 10 minutes. The solution was then treated with diphenyl phosphorylazide (0.76 mL, 3.52), and the mixture was heated to reflux for 2 hours. At this time, the solution was cooled and divided into 2 equal portions. One portion was treated with 2,6 -diisopropyl-aniline (0.37 mL, 1.94 mmol), and the resulting solution was warmed to 50° C. for 10 hours. The solution was cooled, and poured into water (150 mL). This was extracted with methylene chloride (2×150 mL), and the extracts were washed with 1N aqueous hydrochloric acid (150 mL), 1N aqueous sodium bicarbonate (150 mL), and saturated brine (150 mL), then combined, dried over anhydrous magnesium sulfate, filtered and evaporated. The residue was separated by flash chromatography (1:9 ethyl acetate-hexane, then ethyl acetate) to afford the title product as a solid, mp 157°–159° C. (0.22 g, 0.48 mmol, 25%). $^1$H NMR (CDCl$_3$): δ 7.32 (1H, t, J=7.7 Hz); 7.19 (2H, d, J=7.7 Hz); 5.82 (1H, br s); 5.23-5.15 (1H, m); 4.46 (1H, br d, J=6 Hz); 3.26 (2H, heptet, J=6.6 Hz); 3.05 (1H, d, J= 15.7 Hz); 2.95 (1H, d, J=15.7 Hz); 2.45 (1H, br d, J= 16.5 Hz); 2.13 (1H, br dd, J=16.5, 4 Hz); 2.00-1.80 (4H, m); 1.30-1.10 (24H, m); 0.88 (3H, t, J=7.0 Hz); 0.87 (3H, t, J=7.0 Hz). $^{13}$C NMR (CDCl$_3$): δ 156.3, 148.0, 130.1, 130.0, 129.3, 124.1, 49.8, 37.4, 33.8, 33.1, 31.9, 31.8, 28.3, 28.0, 24.5, 24.5, 23.3, 23.2, 23.2, 23.0, 22.5, 22.4, 14.1. IR (KBr): 3310, 3260, 2958, 2928, 2862, 1634, 1576, 1466, 1238, 726 cm$^{-1}$. Mass spectrum (NH$_3$-CI/DDIP): m/z 461 (10%); 460 (34%); 459 (100%); 381 (2%); 221 (10%). Elemental analysis: calculated C 73.31, H 10.11, N 6.11; observed C 73.02, H 10.08, N 6.04.

EXAMPLE 647

Preparation of 1-(2,6-diisopropylphenyl)-3-[(4,5 -dipentyl-3,6-dihydro-2H-thiopyran-2-yl)methyl]-urea Part A. A mixture of 2-mercaptoacetophenone (6.96 g, 45.7 mmol), chloroacetonitrile (3.00 mL, 47.4 mmol), and potassium carbonate (7.21 g, 52.2 mmol) in tetrahydrofuran (100 mL) was stirred at ambient temperature for 12 hours. The mixture was poured into water (400 mL), and this was extracted with ethyl acetate (400 mL), then methylene chloride (400 mL). The extracts were combined, dried over anhydrous magnesium sulfate, filtered and evaporated. The residual oil was separated by flash chromatography (1:4 ethyl acetate-hexane) to afford the product, phenacylthioacetonitrile, as a pale pink oil (7.51 g, 39.3 mmol, 86%). $^1$H NMR (CDCl$_3$): δ 7.96 (2H, dd, J=8.0, 1.1 Hz); 7.65-7.56 (1H, m); 7.50 (2H, t, J=7.7 Hz); 4.13 (2H, s); 3.45 (2H, s). Mass spectrum (NH$_3$-CI/DDIP): m/z 210 (21%); 209 (100%); 192 (2%); 170 (1%); 139 (1%).

Part B. The standard photolysis procedure was employed here. Thus, the sulfide prepared in Part A above (1.47 g, 7.69 mmol) and 2,3-dipentyl-1,3-butadiene (2.05 g, 10.6 mmol) were used to prepare, after chromatography (1:19 ethyl acetate-hexane), the product, 4,5-dipentyl- 3,6-dihydro-2H-thiopyran-2-carbonitrile, as an oil (1.47 g, 5.54 mmol, 72%). $^1$H NMR (CDCl$_3$): δ 3.76 (1H, t, J= 4.6 Hz); 3.50 (1H, d, J=16.8 Hz); 3.03 (1H, d, J= 16.8 Hz); 2.60 (1H, ddd, J=17.4, 2.7, 1.0 Hz); 2.47 (1H, dd, J=17.4, 3.7 Hz); 3.22-2.95 (4H, m); 1.49-1.22 (12H, m); 0.90 (6H, t, J=6.6 Hz). Mass spectrum (NH$_3$ -CI/DDIP): m/z 284 (20%); 283 (100%); 265 (2%); 239 (1 %); 194 (1%).

Part C. A solution of lithium aluminum hydride (12.0 mL in tetrahydrofuran, 1.0M, 12.0 mmol) was cooled to 0° C., and treated dropwise with a solution of the nitrile prepared in Part B above (1.47 g, 5.54 mmol) in tetrahydrofuran (5 mL). After being allowed to warm to ambient temperature over 14 hours with stirring, the reaction mixture was quenched by the slow addition (at 0° C.) with water (1 mL), then 15% aqueous sodium hydroxide (3 mL), then water (3 mL). The resulting mixture was filtered through celite, dried over anhydrous potassium carbonate, refiltered and evaporated to afford the crude product, 2-aminomethyl-4,5-dipentyl- 3,6-dihydro-2H-thiopyran, which was used directly in the next step. $^1$H NMR (CDCl$_3$): δ 3.14 (1H, d, J=16 Hz); 3.00 (1H, d, J=16 Hz); 2.89-2.76 (2H, m); 2.35 (1H, d, J=16 Hz); 2.19-1.97 (6H, m); 1.43-1.15 (14H, m); 0.89 (6H, t, J=6.6 Hz). Mass spectrum (NH$_3$-CI/DDIP): m/z 272 (7%); 271 (19%); 270 (100%); 253 (29%); 239 (2 %).

Part D. The amine product from Part C above (ca. 1.8 mmol) was dissolved in methylene chloride (10 mL), and cooled to 0° C. The solution was treated with 2,6 -diisopropylphenyl-isocyanate (0.50 mL, 2.10 mmol) by syringe. The mixture was allowed to stir for 12 hours, then evaporated, and the residue was separated by flash chromatography (7:93 ethyl acetate-hexane) to afford the title product as a solid, mp 65°–67° C. (490 mg, 1.04 mmol, 58%). $^1$H NMR (CDCl$_3$): δ 7.40-7.07 (3H, m); 6.06 (1H, br s); 5.30 (1H, br s); 3.61-3.46 (2H, m); 3.29 (2H, heptet, J=6.6 Hz); 3.19-2.87 (3H, m); 2.39-2.29 (1H, m); 2.08-1.96 (5H, m); 1.40-1.15 (24H, m); 0.88 (6H, t, J=6 Hz); 0.87 (6H, t, J=6 Hz). $^{13}$C NMR (CDCl$_3$): δ 157.9, 148.1, 131.1, 128.4, 128.0, 124.0, 123.4, 43.7, 40.0, 34.1, 33.9, 33.2, 32.0, 31.9, 28.6, 28.4, 28.3, 28.0, 25.6, 24.1, 23.9, 22.6, 14.1, 14.0. IR (KBr): 3320, 2960, 2928, 1638, 1590, 1556, 1466, 1362, 1256 cm$^{-1}$. Mass spectrum (NH$_3$-CI/DDIP): m/z 475 (10%); 474 (34 %); 473 (100%); 381 (99%); 252 (2%). High-resolution mass spectrum: for C$_{29}$H$_{49}$N$_2$OS, calculated 473.3566, measured 473.3566, difference 0 ppm.

EXAMPLE 695

Preparation of 1-[2,6-bis(1-methylethyl)phenyl]-3-[2 -(3,6-dihydro-4,5-dipentyl-2H-thiopyran-2-yl)ethyl]-urea The title compound is expected to be synthesized using the procedures described below.

Part A. The compound from Example 599, Part A may be treated at 0° C. with lithium aluminum hydride in tetrahydrofuran. After stirring for at least 6 hours, the solution is quenched by the sequential addition of water, 15% aqueous sodium hydroxide, and more water. The solution is filtered through a celite plug, dried over anhydrous magnesium sulfate, refiltered and evaporated to afford 3,6-dihydro-4,5-dipentyl-2H-thiopyran- 2-yl-methanol.

Part B. The alcohol from Part A above is dissolved in methylene chloride along with carbon tetrabromide, and cooled to 0° C. A methylene chloride solution of triphenylphosphine is added dropwise. The mixture is stirred for 14 hours, then evaporated and rapidly eluted through a plug of silica gel with an appropriate solvent system to afford 2-bromomethyl-3,6-dihydro-4,5-dipentyl- 2H-thiopyran. This compound is used directly, and treated with potassium cyanide in dimethylsulfoxide at 80° C. until thin-layer chromatography shows the reaction is complete. At this point, the solution is cooled, and poured into 4 volumes of water. This mixture is extracted with ethyl acetate, and the extract is washed with more water (3× an equal volume), then brine, then dried over anhydrous magnesium sulfate, filtered and evaporated. Chromatography will then purify the product, (3,6-dihydro-4,5-dipentyl-2H-thiopyran-2 -yl)acetonitrile.

Part C. The nitrile from Part B above is treated with lithium aluminum hydride in tetrahydrofuran at reflux temperature until the starting material is consumed. At this point, the reaction mixture is cooled to 0° C., and quenched by sequential addition of water, 15% sodium hydroxide, and more water. The mixture is filtered through celite, dried over anhydrous potassium carbonate, refiltered and evaporated to afford 2-(2-aminoethyl)-3,6-dihydro-4,5-dipentyl-2H-thiopyran.

Part D. The amine from Part C above is dissolved in methylene chloride, and cooled to 0° C. A methylene chloride solution of diisopropylphenylisocyanate is added dropwise. The solution is allowed to stir for at least 4 hours, then evaporated. The title product is purified by either chromatography or recrystallization.

Compounds 599–703 in Table 5 (below) can be prepared by the procedures described in Examples 599, 647 and 695 employing the appropriately substituted starting materials. In addition, carbon chain homologation chemistry, such as that employed in the synthesis of the compound of Example 695, is well familiar to those skilled in the art. Such technology is discussed in the Synthesis section above, and may be used in the preparation of the compounds of Examples 696, 697 and 698.

EXAMPLE 708

Preparation of N-[2,4-bis(methylthio)-6-methylpyridin-3-yl]-6,7-dimethoxy-1,2,3,4-tetrahydro-2-thianaphthalene-1-carboxamide Part A. A solution of 3,4-dimethoxyphenethyl alcohol (7.30 g, 40.1 mmol) and carbon tetrabromide (17.3 g, 52.1 mmol) in methylene chloride (100 mL) was cooled to 0° C., and a solution of triphenylphosphine (13.7 g, 52.1 mmol) in methylene chloride (50 mL) was added dropwise with stirring. After 20 hours, the reaction mixture was evaporated, and separated by flash chromatography (1:9 ethyl acetate-hexane) to afford the product, 1-(2-bromoethyl)-3,4-dimethoxybenzene, as a waxy solid, mp 72°–73° C. (9.48 g, 38.7 mmol, 96%). $^1$H NMR (CDCl$_3$): δ 6.82 (1H, d, J=8.1 Hz); 6.75 (1H, dd, J=8.1, 1.8 Hz); 6.73 (1H, d, J=1.8 Hz); 3.88 (3H, s); 3.87 (3H, s); 3.55 (2H, t, J=7.7 Hz); 3.11 (2H, t, J=7.7 Hz). Mass spectrum (NH$_3$-Cl/DDIP): m/z 264 (93%); 262 (100%); 245 (9%); 165 (6%).

Part B. A solution of the bromide compound prepared in Part A above (3.90 g, 15.9 mmol), thiolacetic acid (1.20 mL, 16.8 mmol), potassium carbonate (2.60 g, 18.8 mmol), and tetra-n-butylammonium iodide (1.30 g) in tetrahydrofuran (50 mL) was heated to reflux for 18 hours, then cooled. The mixture was poured into water (200 mL), and extracted with methylene chloride (2×200 mL). The extracts were combined, dried over anhydrous magnesium sulfate, filtered and evaporated. The oily residue was separated by flash chromatography (1:9 ethyl acetate-hexane) to afford the product, 2-(3,4-dimethoxyphenyl)ethyl thioacetate, as a waxy, low-melting solid (3.37 g, 14.0 mmol, 88%). $^1$H NMR (CDCl$_3$): δ 6.83–6.74 (3H, m); 3.89 (3H, s); 3.86 (3H, s); 3.10 (2H, t, J=7.7 Hz); 2.81 (2H, t, J=7.7 Hz); 2.34 (3H, s). Mass spectrum (NH$_3$-Cl/DDIP): m/z 243 (6%); 242 (14%); 241 (100%); 199 (45%); 165 (59%).

Part C. A solution of the thiolacetate compound from Part B above (3.37 g, 14.0 mmol) in ethanolic sodium hydroxide (0.25N, 125 mL, 31.2 mmol) was stirred for 14 hours. The mixture was evaporated and neutralized to pH 5 with 6N aqueous hydrochloric acid. The resulting mixture was diluted with water (to 200 mL) and extracted with methylene chloride (2×200 mL). The extracts were combined, dried over anhydrous magnesium sulfate, filtered and evaporated. The crude mercaptan thus obtained was dissolved in acetonitrile (30 mL), and treated with ethyl diethoxy-acetate (2.80 mL, 15.6 mmol) and trimethylsilyl trifluoro-methanesulfonate (0.14 mL, 0.72 mmol). This solution was heated to reflux for 12 hours, then cooled and poured into water (200 mL). This was extracted with ethyl acetate (2×200 mL), and the extracts were washed in sequence with saturated brine (200 mL), combined, dried over anhydrous magnesium sulfate, filtered and evaporated. The residue was separated by flash chromatography (3:17 ethyl acetate-hexane) to afford the product, ethyl 6,7-dimethoxy-1,2,3,4-tetrahydro-2-thianaphthalene-1-carboxylate, as a solid, mp 96°–98° C. (2.27 g, 8.04 mmol, 57%). $^1$H NMR (CDCl$_3$): δ 6.63 (1H, s); 6.61 (1H, s); 4.41 (1H, s); 4.20 (1H, dq, J=10, 7.1 Hz); 4.19 (1H, dq, J=10, 7.1 Hz); 3.36 (1H, dr, J=13.2, 7.7 Hz); 3.06 (1H, d, J=4.8 Hz); 3.04 (1H, d, J=4.8 Hz); 2.73 (1H, dr, J=13.2, 4.8 Hz); 1.29 (3H, t, J=7.1 Hz). Mass spectrum (NH$_3$-Cl/DDIP): m/z 300 (100%); 284 (5%); 283 (31%); 209 (9%).

Part D. The ester compound from Part C above (1.88 g, 6.66 mmol) was stirred in ethanolic sodium hydroxide solution (0.25N, 60.0 mL, 15.0 mmol) for 14 hours. The mixture was evaporated, and the residue was taken up in 1N aqueous sodium hydroxide (120 mL). This solution was washed with ether (2×120 mL), then cooled to 0° C. and neutralized to pH 5 with 6N aqueous hydrochloric acid. This was then extracted with ethyl acetate (2×120 mL), and the extracts were combined, dried over anhydrous magnesium sulfate, filtered and evaporated to afford the product, 6,7-dimethoxy-1,2,3,4-tetrahydro-2-thianaphthalene-1-carboxylic acid, as a solid, mp 167°–169° C. (1.66 g, 6.53 mmol, 98%). $^1$H NMR (CDCl$_3$): δ 6.63 (2H, s); 4.43 (1H, s); 3.86 (3H, s); 3.85 (3H, s); 3.34 (1H, ddd, J=13.8, 8.0, 5.2 Hz); 3.09 (1H, dd, J=10, 4.5 Hz); 3.03 (1H, dd, J=10, 4.9 Hz); 2.74 (1H, dt, J=13.8, 4.7 Hz). Mass spectrum (NH$_3$-Cl/DDIP): m/z 272 (100%); 256 (1%); 255 (8%); 209 (3%); 106 (1%).

Part E. A solution of the acid compound from Part D above (1.66 g, 6.53 mmol) and dimethylformamide (3 drops) in 2:1 benzene-methylene chloride (30 mL) was cooled to 0° C. and treated with a solution of oxalyl chloride (2.00 mL, 22.9 mmol) in benzene (10 mL) dropwise with stirring. After 14 hours, the solution was evaporated, then taken up in tetrahydrofuran (20 mL), and added dropwise to a stirred, ice-cooled solution of 3-amino-2,4-bis(methylthio)-6-methylpyridine (400 mg, 2.00 mmol) and triethylamine (0.50 mL, 3.59 mmol) in tetrahydrofuran (20 mL). The mixture was allowed to stir for 12 hours, then poured into water (120 mL). This was extracted with ethyl acetate (2× 120 mL), and the extracts were combined, dried over anhydrous sodium sulfate, filtered and evaporated. The resulting solid was recrystallized from ethyl acetate (mp 218°–219° C.) to afford the pure title product (600 mg, 1.37 mmol, 69%). $^1$H NMR (CDCl$_3$): δ 7.33 (1H, br s); 6.92 (1H, s); 6.65 (1H, s); 6.63 (1H, s); 4.59 (1H, s); 3.90 (3H, s); 3.88 (3H, s); 3.41 (1H, dt, J=13.2, 6.8 Hz); 3.14-3.08 (2H, m); 2.86 (1H, dt, J=12.8, 5.2 Hz); 2.49 (3H, s); 2.47 (3H, s); 2.39 (3H, s). $^{13}$C NMR (CDCl$_3$): δ 170.0, 156.9, 156.5, 148.8, 148.7, 147.5, 128.5, 123.4, 123.1, 113.6, 113.3, 112.7, 56.0, 55.9, 46.0, 30.2, 25.0, 24.5, 14.0, 12.9. IR (KBr): 3204, 2924, 1648, 1562, 1520, 1466, 1440, 1340, 1254, 1230, 1112, 810 cm$^{-1}$. Mass spectrum (NH$_3$-Cl/DDIP): m/z 439 (16%); 438 (24%); 437 (100%). Elemental analysis: calculated C 55.02, H 5.54, N 6.42; observed C 54.67, H 5.52, N 6.34.

EXAMPLE 711

Preparation of N-[2,6-bis(1-methylethyl)phenyl]-6,7-dimethoxy-1,2,3,4-tetrahydro-2-thianaphthalene-1-carboxamide Part A. A solution of 3,4-dimethoxyphenethyl alcohol (4.63 g, 25.4 mmol), ethyl diethoxyacetate (5.00 mL, 28.0 mmol) and trimethylsilyl trifluoromethanesulfonate (0.50 mL, 2.58 mmol) in acetonitrile (50 mL) was stirred at ambient temperature for 12 hours, then heated to reflux for 18 hours. The solution was cooled, and poured into water (200 mL). This was extracted with ethyl acetate (2×200 mL), and the extracts were washed with brine (200 mL), combined, dried over anhydrous magnesium sulfate, filtered and evaporated. The residual oil was separated by flash chromatography (1:9 ethyl acetate/hexane—1:4 ethyl acetate/hexane) to afford the product, ethyl 6,7-dimethoxy-1,2,3,4-tetrahydro-2-thianaphthalene-1-carboxylate, as an oil (1.68 g, 6.31 mmol, 25%). $^1$H NMR (CDCl$_3$): δ 6.92 (1H, s); 6.62 (1H, s); 4.32-4.22 (3H, m); 4.04-3.96 (1H, m); 3.87 (3H, s); 3.86 (3H, s); 2.90-2.79 (2H, m); 1.32 (3H, t, J=7.0 Hz). Mass spectrum (NH$_3$-CI/DDIP): m/z 269 (1 %); 268 (7%); 267 (53%); 233 (5%); 193 (100%).

Part B. A solution of the ester prepared in Part A above (1.68 g, 6.31 mmol) in ethanolic sodium hydroxide (60.0 mL, 0.25M in 95% ethanol, 15.0 mmol) was stirred at ambient temperature for 14 hours. The solution was evaporated, and the residue neutralized to pH 5 with 1N aqueous hydrochloric acid. This was diluted to 100 mL with water, and extracted with ethyl acetate (2×100 mL). The extracts were washed with brine, combined, dried over anhydrous magnesium sulfate, filtered and evaporated to afford the product, 6,7-dimethoxy-1,2,3,4-tetrahydro-2-thianaphthalene-1-carboxylic acid, as an oil (1.42 g, 5.96 mmol, 94%). $^1$H NMR (CDCl$_3$): δ 7.06 (1H, s); 6.62 (1H, s); 5.30 (1H, s); 4.34-4.24 (1H, m); 4.02-3.92 (1H, m); 3.87 (6H, s); 2.94-2.72 (2H, m). Mass spectrum (NH$_3$-CI/DDIP): m/z 241 (2%); 240 (11%); 239 (87%); 221 (8%); 193 (100%).

Part C. A solution of the acid compound prepared in Part B above (1.42 g, 5.96 mmol) and dimethylformamide (2 drops) in benzene (30 mL) was treated with a solution of oxalyl chloride (1.60 mL, 18.3 mmol) in benzene (5 mL). The solution was stirred at ambient temperature for 12 hours, then evaporated. The residual material represented sufficiently pure product, 6,7-dimethoxy-1,2,3,4-tetrahydro-2-thianaphthalene-1-carboxylic acid chloride.

Part D. A solution of the acid chloride compound prepared in Part C above (3 mmol) in tetrahydrofuran (10 mL) was added to an ice-cooled solution of diisopropylaniline (0.60 mL, 3.18 mmol) and triethylamine (1.00 mL, 7.17 mmol) in tetrahydrofuran (20 mL) dropwise over 5 minutes. The solution was stirred for an additional 12 hours, then poured into water (100 mL) and extracted with ethyl acetate (2×100 mL). The extracts were washed with saturated brine (100 mL), then combined, dried over anhydrous magnesium sulfate, filtered and evaporated. The resulting solid was recrystallized to purity from ether to afford the title product, mp 72°–74° C. (760 mg, 1.91 mmol, 64%). $^1$H NMR (CDCl$_3$): δ 7.87 (1H, s); 7.34 (1H, s); 7.27 (1H, t, J=8.0 Hz); 7.14 (2H, d, J=8.0 Hz); 6.64 (1H, s); 5.33 (1H, s); 4.36 (1H, ddd, J=11.3, 5.8, 1.4 Hz); 3.98-3.88 (1H, m); 3.89 (3H, s); 3.82 (3H, s); 3.20-3.08 (1H, m); 2.98-2.82 (2H, m); 2.66 (1H, br d, J=16.1 Hz); 1.09 (12H, d, J=7.0 Hz). $^{13}$C NMR (CDCl$_3$): δ 170.5, 148.3, 147.7, 146.3, 130.4, 128.4, 124.8, 123.8, 123.5, 111.3, 108.4, 77.1, 64.5, 55.9, 55.8, 28.6, 28.2, 23.5, 23.4. IR (KBr): 3402, 2962, 2934, 1688, 1514, 1466, 1362, 1330, 1258, 1222, 1098, 796 cm$^{-1}$. Mass spectrum (NH$_3$-CI/DDIP): m/z 400 (4%); 399 (27%); 398 (100%); 284 (1%); 193 (2%). Elemental analysis: calculated C 72.52, H 7.86, N 3.52; observed C 72.14, H 7.89, N 3.41.

Compounds 704–872 in Table 6 (below) can be prepared by the procedures described in Examples 708 and 711 employing the appropriately substituted starting materials.

EXAMPLE 899

Preparation of N-[2,4-bis(methylthio)-6-methylpyridin-3-yl]-4-butyl-7,8-dimethoxy-1,3,4,5-tetrahydro-2-benzothiepin-1-carboxamide Part A. Sodium hydride suspension in mineral oil (2.40 g, 50% w/w) was washed with hexane, allowed to settle, decanted by cannula and dried under vacuum. Dimethylsulfoxide (50 mL) was added, and a solution of diethyl butylmalonate (10.0 mL, 45.5 mmol) in dimethylsulfoxide (10 mL) was added dropwise with stirring over 30 minutes. The mixture was stirred for 1 hour more, then treated with a solution of 3,4-dimethoxybenzyl bromide (9.55 g, 41.3 mmol) in dimethylsulfoxide (10 mL). This solution was allowed to stir for 12 hours, then poured over ice. The mixture was allowed to melt, and extracted with ethyl acetate (2× 400 mL). The extracts were washed in sequence with water (3×400 mL) and brine (400 mL), then combined, dried over anhydrous magnesium sulfate, filtered and evaporated. The oily residue was separated by flash chromatography (1:9 ethyl acetate-hexane) to afford the product, diethyl 1-butyl-1-(3,4-dimethoxybenzyl)malonate, as an oil (9.68 g, 26.4 mmol, 64%). $^1$H NMR (CDCl$_3$): δ 6.79-6.60 (3H, m); 4.26-4.08 (4H, m); 3.85 (3H, s); 3.83 (3H, s); 3.19 (2H, s); 1.81-1.74 (2H, m); 1.39-1.20 (4H, m); 1.25 (6H, t, J=7.1 Hz); 0.91 (3H, t, J=7.0 Hz). Mass spectrum (NH$_3$-CI/DDIP): m/z 384 (14%); 368 (21%); 367 (100%); 321 (3%); 151 (1%).

Part B. The ester from Part A above (9.68 g, 26.4 mmol) was dissolved in 95% ethanol (300 mL) and treated with sodium hydroxide (75 mmol). This solution was heated to reflux for 12 hours, then cooled and evaporated. The residue was acidified with 1N hydrochloric acid, and extracted with ethyl acetate (2×200 mL). The extracts were washed in sequence with brine (200 mL), then combined, dried over anhydrous magnesium sulfate, filtered and evaporated to afford the product, monoethyl 1-butyl-1-(3,4-dimethoxybenzyl)malonate, as an oil (8.10 g, 23.9 mmol, 91%). $^1$H NMR (CDCl$_3$): δ 6.79-6.60 (3H, m); 4.31 (1H, dq, J=11.0, 7.3 Hz); 4.23 (1H, dq, J= 11.0, 7.3 Hz); 3.84 (3H, s); 3.83 (3H, s); 3.35 (1H, d, J=14.0 Hz); 3.07 (1H, d, J=14.0 Hz); 2.16-1.89 (2H, m); 1.35 (3H, t, J=7.3 Hz); 1.35-1.21 (4H, m); 0.90 (3H, t, J=7.0 Hz).

Part C. The acid compound from Part B above (5.15 g, 15.2 mmol) was dissolved in pyridine (15 mL), and treated with morpholine (2.00 mL, 22.9 mmol). The mixture was heated to reflux for 14 hours, then cooled and evaporated. The residue was taken up in ethyl acetate (200 mL), and washed with 1N hydrochloric acid (3×200 mL) and brine (200 mL). The solution was dried over magnesium sulfate, filtered and evaporated, and the residual oil was separated by flash chromatography (1:9 ethyl acetate-hexane) to afford the product, ethyl 2-(3,4-dimethoxybenzyl)hexanoate, as an oil (4.00 g, 13.6 mmol, 89%). $^1$H NMR (CDCl$_3$): δ 6.80-6.68 (3H, m); 4.06 (2H, br q, J=7 Hz); 3.86 (3H, s); 3.85 (3H, s); 2.87 (1H, dd, J=13.2, 8.4 Hz); 2.75-2.55 (2H, m); 1.70-1.58 (1H, m); 1.57-1.42 (1H, m); 1.37-1.21 (4H, m); 1.17 (3H, t, J=7.0 Hz); 0.87 (3H, t, J=6.8 Hz).

Part D. A solution of the ester prepared in Part C above (4.00 g, 13.6 mmol) in tetrahydrofuran (20 mL) was added dropwise to an ice-cooled solution of lithium aluminum hydride (30 mmol) in tetrahydrofuran (30 mL). The ice bath was removed, and the mixture was warmed to ambient temperature for 14 hours. The solution was then recooled to 0° C., and quenched by the slow addition of 1 mL water, 3 mL 15% sodium hydroxide, and 3 mL water. The resulting mixture was filtered through a plug of celite, and the filtrate was dried over anhydrous potassium carbonate, filtered and evaporated. The residue was separated by flash chromatography (1:4 ethyl acetate-hexane) to afford the product, 2-(3,4-dimethoxybenzyl)-1-hexanol, as an oil (3.39 g, 13.4 mmol, 99%). $^1$H NMR (CDCl$_3$): δ 6.81-6.70 (3H, m); 3.87 (3H, s);

3.86 (3H, s); 3.54 (2H, t, J=5.1 Hz); 2.59 (2H, d, J=7.0 Hz); 1.80–1.71 (1H, m); 1.39–1.17 (7H, m); 0.89 (3H, t, J=7.0 Hz). Mass spectrum (NH$_3$-CI/DDIP): m/z 254 (5%); 253 (33%); 235 (100%); 151 (43%).

Part E. The alcohol compound from Part D above (3.39 g, 13.4 mmol) and carbon tetrabromide (5.78 g, 17.4 mmol) were dissolved in methylene chloride (30 mL). This solution was cooled to 0° C. and treated with a 20 mL methylene chloride solution of triphenylphosphine (4.57 g, 17.4 mmol). The solution was allowed to stir for 14 hours, then evaporated. The residual oil was separated by flash chromatography (1:9 ethyl acetate-hexane) to afford the product, 1-bromo-2-(3,4-dimethoxybenzyl)hexane, as an oil (4.01 g, 12.7 mmol, 95%). $^1$H NMR (CDCl$_3$): δ 6.81–6.71 (3H, m); 3.88 (3H, s); 3.87 (3H, s); 3.41 (1H, dd, J=9.9, 4,4 Hz); 3.33 (1H, dd, J=9.9, 4.0 Hz); 2.64 (1H, dd, J=13.5, 6.2 Hz); 2.58 (1H, dd, J=13.5, 8.0 Hz); 1.90–1.80 (1H, m); 1.48–1.24 (6H, m); 0.91 (3H, t, J=6.8 Hz). Mass spectrum (NH$_3$-CI/DDIP): m/z 334 (98%); 332 (100%); 317 (33%); 315 (34%); 252 (3%).

Part F. A solution of the bromide from Part E above (4.01 g, 12.7 mmol), thioacetic acid (1.50 mL, 21.0 mmol), potassium carbonate (2.90 g, 21.0 mmol) and tetra-n-butylammonium iodide (1.45 g) in tetrahydrofuran (50 mL) was heated to reflux for 12 hours. The solution was cooled, and poured into water (200 mL). This was extracted with methylene chloride (2×200 mL), and the extracts were combined, dried over magnesium sulfate, filtered and evaporated. The residual oil was purified by elution through a plug of silica gel with 1:4 ethyl acetate-hexane. Evaporation gave the product, 2-(3,4-dimethoxybenzyl)-1-thioacetoxyhexane, as an oil (3.62 g, 11.7 mmol, 92%) $^1$H NMR (CDCl$_3$): δ 6.79 (1H, d, J=7.7 Hz); 6.68 (1H, d, J=7.7 Hz); 6.66 (1H, s); 3.87 (3H, s); 3.86 (3H, s); 2.89 (2H, d, J=5.9 Hz); 2.54 (2H, d, J=7.0 Hz); 2.34 (3H, s); 1.91–1.81 (1H, m); 1.39–1.22 (6H, m); 0.88 (3H, t, J=7.0 Hz). Mass spectrum (NH$_3$-CI/DDIP): m/z 329 (19%); 328 (100%); 311 (11%).

Part G. A solution of the thioacetate from Part F (3.62 g, 11.7 mmol) and sodium hydroxide (35 mmol) in 95% ethanol (140 mL) was stirred for 4 hours, then evaporated. The residue was separated with 1N hydrochloric acid, and extracted with methylene chloride (2×200 mL). The extracts were combined, dried over magnesium sulfate, filtered and evaporated. The residual oil was taken up in 25 mL acetonitrile, and 20 mL of the resulting solution was treated with ethyl diethoxyacetate (2.00 mL, 11.2 mmol) and trimethylsilyl trifluoromethanesulfonate (0.10 mL, 0.52 mmol). The resulting solution was heated to reflux for 12 hours, then cooled and poured into water (100 mL). This mixture was extracted with ethyl acetate (2×100 mL), and the extracts were washed in sequence with brine (100 mL), combined, dried over anhydrous magnesium sulfate, filtered and evaporated. The oil was separated by flash chromatography (1:9 ethyl acetate-hexane) to afford the product, ethyl 4-butyl-7,8-dimethoxy-1,3,4,5-tetrahydro-2-benzothiepin-1-carboxylate, as an inseparable 1.1:1 mixture of E and Z isomers (1.28 g, 3.63 mmol, 41%). Mass spectrum (NH$_3$-CI/DDIP): m/z 370 (71%); 354 (22%); 353 (100%); 279 (19%).

Part H. The ester from Part G above (1.28 g, 3.63 mmol) was dissolved in 95% ethanol (32 mL), and treated with sodium hydroxide (8.00 mmol). The mixture was stirred at ambient temperature for 10 hours, then evaporated. The residue was acidified with 1N hydrochloric acid (100 mL), and extracted with ethyl acetate (2×100 mL). The extracts were washed in sequence with brine (100 mL), then combined, dried over anhydrous magnesium sulfate, filtered and evaporated to afford the product, 4-butyl-7,8-dimethoxy-1, 3,4,5-tetrahydro-2-benzothiepin-1-carboxylic acid, as a 1.1:1 mixture of diastereomers (1.11 g, 3.42 mmol, 94%). Mass spectrum (NH$_3$-CI/DDIP): m/z 343 (19%); 342 (100%); 325 (44%); 277 (6%).

Part I. A solution of the acid prepared in Part H above (1.11 g, 3.42 mmol) and one drop dimethylformamide in methylene chloride (5 mL) was treated by syringe with a solution of oxalyl chloride (1.00 mL, 11.5 mmol) in benzene (5 mL). The solution was stirred at ambient temperature for 12 hours, then evaporated. The residue was taken up in tetrahydrofuran (10 mL), and added to an ice-cooled solution of 3-amino-2,4-bis(methylthio)-6-methylpyridine (680 mg, 3.39 mmol) and triethylamine (1.00 mL, 7.17 mmol) in tetrahydrofuran (10 mL). The resulting solution was stirred for 12 hours, then poured into water (100 mL), and extracted with ethyl acetate (2×100 mL). The extracts were combined, dried over anhydrous sodium sulfate, filtered and evaporated. The residual material was separated by flash chromatography (1:1 ethyl acetate-hexane) to afford the title product as an inseparable mixture of E and Z diastereomers as a solid, mp 143°–145° C. (970 mg, 1.91 mmol, 56%). $^1$H NMR (CDCl$_3$, major isomer): δ 8.07 (1H, br s); 6.92 (1H, s); 6.69 (1H, s); 6.63 (1H, s); 4.92 (1H, s); 3.90 (3H, s); 3.88 (3H, s); 3.18 (1H, dd, J=5.0, 2 Hz); 2.95–2.27 (3H, m); 2.52 (3H, s); 2.49 (3H, s); 2.42 (3H, s); 2.02 –1.92 (1H, m); 1.50–1.24 (6H, m); 0.90 (3H, t, J=6.6 Hz). $^1$H NMR (CDCl$_3$, minor isomer): δ 8.07 (1H, br s); 6.85 (1H, s); 6.66 (1H, s); 6.65 (1H, s); 4.82 (1H, s); 3.89 (3H, s); 3.88 (3H, s); 2.95–2.27 (4H, m); 2.52 (3H, s); 2.49 (3H, s); 2.42 (3H, s); 1.89–1.79 (1H, m); 1.50 –1.24 (6H, m); 0.92 (3H, t, J=6.6 Hz). $^{13}$C NMR (CDCl$_3$, major isomer): δ 168.6, 156.8, 156.3, 148.5, 148.4, 147.6, 131.2, 127.3, 123.7, 114.4, 113.9, 113.4, 56.2, 56.1, 52.4, 38.0, 36.6, 35.3, 32.5, 29.5, 24.4, 22.8, 14.1 (2C), 12.9. $^{13}$C NMR (CDCl$_3$, minor isomer): δ 168.5, 156.8, 156.5, 148.5, 148.3, 147.4, 132.3, 127.6, 123.7, 114.2, 114.0, 113.8, 56.2, 56.1, 52.6, 39.0, 37.9, 35.9, 34.5, 29.3, 24.4, 22.9, 14.1 (2C), 12.9. IR (KBr): 3210, 2954, 2924, 1654, 1564, 1516, 1464, 1440, 1338, 1292, 1274, 1226, 1204, 1172, 1094, 812 cm$^{-1}$. Mass spectrum (NH$_3$-CI/DDIP): m/z 509 (18%); 508 (30%); 507 (100%). Elemental analysis: calculated C 59.26, H 6.76, N 5.53; observed C 59.09, H 6.83, N 5.36.

Compounds 873–971 in Table 7 (below) can be prepared by the procedures described in Example 899 employing the appropriately substituted starting materials.

Compounds 972–1050 in Table 8 (below) can be prepared by the procedures described in the Synthesis section above. All the starting materials for these compounds have already been introduced; in addition, the following compounds are needed (all are commercially available): α-methylbenzylisocyanate, benzylisocyanate, α-methylbenzylamine, and veratryl amine. Using the previously discussed synthetic strategies, it is obvious for those skilled in the art the manner in which the compounds of Examples 972–1050 are prepared.

Utility

The compounds of this invention possess antiatherosclerotic and antihypercholesteolemic efficacy, as evidenced by their activity in the ACAT assays, as described below.

The compounds of the invention are effective antiatherosclerotic agents that act in a variety of ways. The compounds may be inhibitors of the enzyme acyl CoA:cholesterol acyl transferase (ACAT). Inhibition of ACAT has a variety of antiatherosclerotic effects, including inhibiting esterification and transport of cholesterol across the intestinal wall. In addition, by inhibiting cholesterol ester formation, the compounds may be useful in preventing the formation of cholesterol ester rich macrophages (foam cells) in the arterial wall. Foam cells are a source of the large quantity of cholesterol ester found in atheromatous lesions, as compared to the surrounding undiseased tissue. Other compounds of the invention may be inhibitors of cholesterol biosynthesis in the liver. Some compounds of the invention are both ACAT inhibitors and inhibitors of cholesterol biosynthesis.

A. Assay of the Inhibition of Acyl-CoA: Cholesterol Acyltransferase (ACAT) in Hepatic Microsomes (In Vitro Assay)

The ability of the compounds to inhibit ACAT, the enzyme responsible for the intracellular synthesis of cholesteryl esters, was tested as follows. Male Sprague Dawley rats weighing 150–300 g, were fed rat chow ad libitum. The animals were fasted for twenty-four hours prior to being euthanized by $CO_2$. The livers were perfused in situ with 50 ml of cold 0.25 sucrose, excised, and homogenized in three volumes of 0.1M phosphate buffer, pH 7.4, that contained 0.5 mM EDTA (ethylenediamine-tetraacetic acid), 1.0 mM glutathione, 0.25M sucrose and 20 mM leupeptin. Microsomes were obtained by differential centrifugation; the supernatant from an initial spin at 15,000× g for 15 minutes was centrifuged at 105,000× g for 1 hour to pellet the microsomes. The microsomes were suspended in 0.1M phosphate buffer, pH 7.4 with 1 mM GSH and stored at –70° C. Microsomes were used within one month of preparation.

The control assay in a final volume of 200 µl consisted of 200 µg of microsomal protein, 75 µM $^{14}C$-oleoyl-CoA (10,000 dpm/nmol) in 0.1M phosphate, pH 7.4, that contained 1 mM glutathione. Compounds were added in 5 µl of DMSO (dimethyl sulfoxide) and additional controls were run with DMSO only. All components, except the oleoyl-CoA, were preincubated for 15 min. at 37° C. prior to the initiation of the reaction by the addition of oleoyl-CoA. The assay was terminated after 10 min by the addition of 4 ml of chloroform:methanol (2:1, v/v). 20,000 dpm of $^3H$-cholesteryl oleate and 10 µg of unlabeled cholesteryl oleate and oleic acid were added as an internal standard and carriers, respectively. After allowing 10 min. for lipid extraction, the samples were centrifuged at 1,000× g for 10 min to separate the solvent layers. The chloroform layer containing the neutral lipids was spotted onto a Baker SI250-Pa silica gel TLC plate and the plate developed using a hexane:diethyl ether:acetic acid (170:30:1) v/v/v mobile phase. The lipids were visualized by their interaction with iodine vapor and the cholesteryl ester spot was scraped into a scintillation vial and counted. The specific activity of ACAT in the control incubation averaged 260 pmol/min/mg microsomal protein. The data obtained are expressed as the concentration at which ACAT activity is inhibited by 50% ($IC_{50}$).

B. Assay for the Systemic Availability of ACAT Inhibitors (Ex Vivo Assay)

The inhibition of ACAT activity in livers obtained from rats orally dosed with an inhibitor was used as a determination of the compound's systemic availability. The ability of ACAT inhibitors to affect cholesterol esterification in livers obtained from dosed animals was tested as follows. This assay is also referred to herein as the Ex Vivo Assay. Male (CD) Sprague Dawley rats weighing from 190–210 g were fed purina lab chow ad libitum. Rats, three per group, were orally gavaged with 10 mg/kg of active ACAT inhibitor. The compounds were dissolved in ethanol (10% of final volume); a PEG solution (80 propylene glycol:20 polyethylene glycol 400, w:w) was added and the compound was mixed completely prior to dosing. A control group received the dosing vehicle alone. The animals were dosed once on Day 1 (am), twice on Day 2 (am and pm) and once on the morning of Day 3. Three hours after the last dose animals were euthanized using $CO_2$. Livers were perfused with a 0.25M sucrose solution, excised, and frozen. Livers were thawed and resuspended in buffer (2 mL/g, 0.1M Phosphate, pH 7.4, 1.0 mM glutathione, 0.5 mM EDTA, 20 µM leupeptin, 60 µM benzamidine, and 0.25M sucrose). The samples were homogenized and post nuclear microsomes were obtained by centrifugation: 1.000× g for 5 min. and the resulting supernatant, 100,000× g for 1 hr. Microsomes were resuspended in phosphate buffer to approximately 25 mg/mL and frozen at –70° C. until assayed for ACAT activity.

ACAT assays contained in a final volume of 200 µl: 100 ug microsomal protein, 75 µM $^{14}C$-oleoyl-CoA (10,000 dpm/nmol), 0.75 mg bovine serum albumin, 0.1M phosphate buffer, pH 7.4, and 1 mM glutathione. All components, except the oleoyl-CoA, were preincubated for 15 min at 37° C. prior to the initiation of the reaction by the addition of oleoyl-CoA. The assay was terminated after 10 min and ACAT activity determined as described in section A above. The average specific activity of ACAT in the vehicle control group was 661 +/– 64 pmol/min/mg (SEM). The data (% inhibition) are expressed as 100 minus the % ACAT activity in livers from dosed animals versus those from a vehicle control group.

Table A below sets forth the ACAT inhibitory activity of representative compounds of the present invention.

TABLE A

| Ex. No. | Inhibition of ACAT In Vitro ($IC_{50}$, µM) | Ex Vivo Assay (% inhibition) |
|---|---|---|
| 1 | +++ | |
| 2 | +++ | |
| 3 | ++ | |
| 17 | + | |
| 27 | +++ | |
| 28 | +++ | |
| 29 | +++ | |
| 30 | + | |
| 31 | +++ | <10 |
| 32 | ++ | |
| 33 | + | |
| 34 | + | |
| 35 | +++ | |
| 39 | +++ | |
| 40 | +++ | |
| 41 | +++ | |
| 42 | +++ | + |
| 53 | ++ | |
| 57 | +++ | |
| 66 | +++ | ++ |
| 67 | +++ | |
| 68 | +++ | |
| 69 | ++ | |
| 70 | +++ | ++ |
| 79 | +++ | |
| 104 | + | |
| 106 | + | |
| 120 | +++ | |
| 132 | +++ | |
| 136 | +++ | |
| 140 | +++ | <10 |
| 160 | +++ | ++ |
| 164 | +++ | ++ |
| 168 | ++ | |
| 180 | +++ | |
| 184 | +++ | |
| 402 | +++ | |
| 426 | + | |
| 613 | + | |
| 907 | +++ | |

In Table A, ACAT inhibition activity in the In Vitro Assay is represented as follows: +++=<2 µM; ++ =3–10 µM;

+=11–50 µM. In Table A, ACAT inhibition activity in the Ex Vivo Assay is represented as follows: ++=>50%; +=10–49%.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences,* Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiatherosclerotic and antihypercholesteolemic agent.

The compounds of this invention can be administered by any means that produces contact of the active agent with the agent's site of action, ACAT, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | Wt. % |
|---|---|
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | Wt. % |
|---|---|
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | Wt. % |
|---|---|
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | Wt. % |
|---|---|
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | Wt. % |
|---|---|
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | Wt % |
|---|---|
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent. The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of atherosclerosis or hypercholesteolemia, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

The term "consisting essentially of" where used in the present disclosure is intended to have its customary meaning; namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited references may provide further useful information, however, these cited materials are hereby incorporated by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

The Tables below set forth representative compounds of the invention.

TABLE 1

| Ex. No. | $R^1$ | $R^2$ | $R^4$ | $R^6$ | $R^7$ | X | G | mp, °C. |
|---|---|---|---|---|---|---|---|---|
| 1 | H | H | H | $C_6H_{13}$ | $C_6H_{13}$ | S | a | 60–63 |
| 2 | H | H | H | $C_6H_{13}$ | $C_6H_{13}$ | S | b | 79–81 |
| 3 | H | H | H | $C_6H_{13}$ | $C_6H_{13}$ | S | c | 91–93 |
| 4 | H | H | H | $C_6H_{13}$ | $C_6H_{13}$ | S | d | — |
| 5 | H | H | H | $C_6H_{13}$ | $C_6H_{13}$ | S | e | — |
| 6 | H | H | H | $C_6H_{13}$ | $C_6H_{13}$ | S | f | — |
| 7 | H | H | H | $C_6H_{13}$ | $C_6H_{13}$ | S | g | — |
| 8 | H | H | H | $C_6H_{13}$ | $C_6H_{13}$ | S | h | — |
| 9 | H | H | H | $C_6H_{13}$ | $C_6H_{13}$ | S | i | — |
| 10 | H | H | H | $C_6H_{13}$ | $C_6H_{13}$ | S | j | — |
| 11 | H | H | H | $C_6H_{13}$ | $C_6H_{13}$ | S | k | — |
| 12 | H | H | H | $C_6H_{13}$ | $C_6H_{13}$ | S | l | — |
| 13 | H | H | H | $C_6H_{13}$ | $C_6H_{13}$ | S | m | — |
| 14 | H | $(CH_3)_2CH$ | H | H | H | S | a | — |
| 15 | H | $(CH_3)_3C$ | H | H | H | S | b | — |
| 16 | H | $(CH_3)_3C$ | H | H | H | S | c | — |
| 17 | H | $(CH_3)_3C$ | H | H | H | S | d | 107–109 |
| 18 | H | $(CH_3)_3C$ | H | H | H | S | e | — |
| 19 | H | $(CH_3)_3C$ | H | H | H | S | f | — |
| 20 | H | $(CH_3)_3C$ | H | H | H | S | g | — |
| 21 | H | $(CH_3)_3C$ | H | H | H | S | h | — |
| 22 | H | $(CH_3)_3C$ | H | H | H | S | i | — |
| 23 | H | $(CH_3)_3C$ | H | H | H | S | j | — |
| 24 | H | $(CH_3)_3C$ | H | H | H | S | k | — |
| 25 | H | $(CH_3)_3C$ | H | H | H | S | l | — |
| 26 | H | $(CH_3)_3C$ | H | H | H | S | m | — |
| 27 | H | H | H | $C_5H_{11}$ | $C_5H_{11}$ | S | a | 88–89 |
| 28 | H | H | H | $C_5H_{11}$ | $C_5H_{11}$ | S | b | 95–77 |
| 29 | H | H | H | $C_5H_{11}$ | $C_5H_{11}$ | S | c | 93–94 |
| 30 | H | H | H | $C_5H_{11}$ | $C_5H_{11}$ | S | d | oil[n] |
| 31 | H | H | H | $C_5H_{11}$ | $C_5H_{11}$ | S | e | 80–82 |
| 32 | H | H | H | $C_5H_{11}$ | $C_5H_{11}$ | S | f | 82–84 |
| 33 | H | H | H | $C_5H_{11}$ | $C_5H_{11}$ | S | g | oil[o] |
| 34 | H | H | H | $C_5H_{11}$ | $C_5H_{11}$ | S | h | 99–100 |
| 35 | H | H | H | $C_8H_{17}$ | $C_8H_{17}$ | S | c | 77–79 |
| 36 | H | H | H | $C_5H_{11}$ | $C_5H_{11}$ | S | j | 84–86 |
| 37 | H | H | H | $C_5H_{11}$ | $C_5H_{11}$ | S | k | 94–96 |
| 38 | H | H | H | $C_8H_{17}$ | $C_8H_{17}$ | S | l | — |
| 39 | H | H | H | $C_5H_{11}$ | $C_5H_{11}$ | S | m | 94–95 |
| 40 | H | H | H | $C_4H_9$ | $C_4H_9$ | S | a | 111–113 |
| 41 | H | H | H | $C_4H_9$ | $C_4H_9$ | S | b | 115–117 |
| 42 | H | H | H | $C_4H_9$ | $C_4H_9$ | S | c | 105–107 |
| 43 | H | H | H | $C_4H_9$ | $C_4H_9$ | S | d | — |
| 44 | H | H | H | $C_4H_9$ | $C_4H_9$ | S | e | — |
| 45 | H | H | H | $C_4H_9$ | $C_4H_9$ | S | f | — |
| 46 | H | H | H | $C_4H_9$ | $C_4H_9$ | S | g | — |
| 47 | H | H | H | $C_4H_9$ | $C_4H_9$ | S | h | — |
| 48 | H | H | H | $C_4H_9$ | $C_4H_9$ | S | i | — |
| 49 | H | H | H | $C_4H_9$ | $C_4H_9$ | S | j | — |
| 50 | H | H | H | $C_4H_9$ | $C_4H_9$ | S | k | — |
| 51 | H | H | H | $C_4H_9$ | $C_4H_9$ | S | l | — |
| 52 | H | H | H | $C_4H_9$ | $C_4H_9$ | S | m | — |
| 53 | H | H | H | $CH_3$ | $CH_3$ | S | a | 189–191 |
| 54 | H | H | H | $CH_3$ | $CH_3$ | S | b | — |
| 55 | H | H | H | $CH_3$ | $CH_3$ | S | c | — |
| 56 | H | H | H | $CH_3$ | $CH_3$ | S | d | — |
| 57 | H | H | H | $CH_3$ | $CH_3$ | S | e | 188–190 |
| 58 | H | H | H | $CH_3$ | $CH_3$ | S | f | — |
| 59 | H | H | H | $CH_3$ | $CH_3$ | S | g | — |
| 60 | H | H | H | $CH_3$ | $CH_3$ | S | h | — |
| 61 | H | H | H | $CH_3$ | $CH_3$ | S | i | — |
| 62 | H | H | H | $CH_3$ | $CH_3$ | S | j | — |
| 63 | H | H | H | $CH_3$ | $CH_3$ | S | k | — |
| 64 | H | H | H | $CH_3$ | $CH_3$ | S | l | — |
| 65 | H | H | H | $CH_3$ | $CH_3$ | S | m | — |
| 66 | H | $C_5H_{11}$ | $C_5H_{11}$ | H | H | S | a | 99–101 |
| 67 | H | $C_5H_{11}$ | $C_5H_{11}$ | H | H | S | b | 125–127 |

TABLE 1-continued

| Ex. No. | R¹ | R² | R⁴ | R⁶ | R⁷ | X | G | mp, °C. |
|---|---|---|---|---|---|---|---|---|
| 68 | H | $C_5H_{11}$ | $C_5H_{11}$ | H | H | S | c | 110–112 |
| 69 | H | $C_5H_{11}$ | $C_5H_{11}$ | H | H | S | d | 106–108 |
| 70 | H | $C_5H_{11}$ | $C_5H_{11}$ | H | H | S | e | p |
| 71 | H | $C_5H_{11}$ | $C_5H_{11}$ | H | H | S | f | — |
| 72 | H | $C_5H_{11}$ | $C_5H_{11}$ | H | H | S | g | — |
| 73 | H | $C_5H_{11}$ | $C_5H_{11}$ | H | H | S | h | — |
| 74 | H | $C_5H_{11}$ | $C_5H_{11}$ | H | H | S | i | — |
| 75 | H | $C_5H_{11}$ | $C_5H_{11}$ | H | H | S | j | — |
| 76 | H | $C_5H_{11}$ | $C_5H_{11}$ | H | H | S | w | oil |
| 77 | H | $C_5H_{11}$ | $C_5H_{11}$ | H | H | S | x | 83–85 |
| 78 | H | $C_5H_{11}$ | $C_5H_{11}$ | H | H | S | y | 55–57 |
| 79 | H | H | $C_5H_{11}$ | $C_5H_{11}$ | H | S | a | 85–86 |
| 80 | H | H | $C_5H_{11}$ | $C_5H_{11}$ | H | S | b | — |
| 81 | H | H | $C_5H_{11}$ | $C_5H_{11}$ | H | S | c | — |
| 82 | H | H | $C_5H_{11}$ | $C_5H_{11}$ | H | S | d | — |
| 83 | H | H | $C_5H_{11}$ | $C_5H_{11}$ | H | S | e | — |
| 84 | H | H | $C_5H_{11}$ | $C_5H_{11}$ | H | S | f | — |
| 85 | H | H | $C_5H_{11}$ | $C_5H_{11}$ | H | S | g | — |
| 86 | H | H | $C_5H_{11}$ | $C_5H_{11}$ | H | S | h | — |
| 87 | H | H | $C_5H_{11}$ | $C_5H_{11}$ | H | S | i | — |
| 88 | H | H | $C_5H_{11}$ | $C_5H_{11}$ | H | S | j | — |
| 89 | H | H | $C_5H_{11}$ | $C_5H_{11}$ | H | S | k | — |
| 90 | H | H | $C_5H_{11}$ | $C_5H_{11}$ | H | S | l | — |
| 91 | H | H | $C_5H_{11}$ | $C_5H_{11}$ | H | S | m | — |
| 92 | H | H | H | $C_6H_{13}$ | $C_6H_{13}$ | O | a | — |
| 93 | H | H | H | $C_6H_{13}$ | $C_6H_{13}$ | O | b | — |
| 94 | H | H | H | $C_6H_{13}$ | $C_6H_{13}$ | O | c | — |
| 95 | H | H | H | $C_6H_{13}$ | $C_6H_{13}$ | O | m | — |
| 96 | H | H | H | $C_5H_{11}$ | $C_5H_{11}$ | O | a | — |
| 97 | H | H | H | $C_5H_{11}$ | $C_5H_{11}$ | O | b | — |
| 98 | H | H | H | $C_5H_{11}$ | $C_5H_{11}$ | O | c | — |
| 99 | H | H | H | $C_5H_{11}$ | $C_5H_{11}$ | O | m | — |
| 100 | H | H | H | $C_4H_9$ | $C_4H_9$ | O | a | — |
| 101 | H | H | H | $C_4H_9$ | $C_4H_9$ | O | b | — |
| 102 | H | H | H | $C_4H_9$ | $C_4H_9$ | O | c | — |
| 103 | H | H | H | $C_4H_9$ | $C_4H_9$ | O | m | — |
| 104 | H | H | H | $CH_3$ | $CH_3$ | O | a | 150–151 |
| 105 | H | H | H | $CH_3$ | $CH_3$ | O | b | — |
| 106 | H | H | H | $CH_3$ | $CH_3$ | O | c | 149–150 |
| 107 | H | H | H | $CH_3$ | $CH_3$ | O | m | — |
| 108 | H | $C_5H_{11}$ | $C_5H_{11}$ | H | H | O | a | — |
| 109 | H | $C_5H_{11}$ | $C_5H_{11}$ | H | H | O | b | — |
| 110 | H | $C_5H_{11}$ | $C_5H_{11}$ | H | H | O | c | — |
| 111 | H | $C_5H_{11}$ | $C_5H_{11}$ | H | H | O | m | — |
| 112 | H | H | $C_5H_{11}$ | $C_5H_{11}$ | H | O | a | — |
| 113 | H | H | $C_5H_{11}$ | $C_5H_{11}$ | H | O | b | — |
| 114 | H | H | $C_5H_{11}$ | $C_5H_{11}$ | H | O | c | — |
| 115 | H | H | $C_5H_{11}$ | $C_5H_{11}$ | H | O | m | — |
| 116 | $CH_3$ | H | H | $C_5H_{11}$ | $C_5H_{11}$ | S | a | — |
| 117 | $CH_3$ | H | H | $C_5H_{11}$ | $C_5H_{11}$ | S | b | — |
| 118 | $CH_3$ | H | H | $C_5H_{11}$ | $C_5H_{11}$ | S | c | — |
| 119 | $CH_3$ | H | H | $C_5H_{11}$ | $C_5H_{11}$ | S | m | — |
| 120 | H | $C_5H_{11}$ | $C_5H_{11}$ | H | H | SO | e | oil$^q$ |
| 121 | H | H | H | $C_5H_{11}$ | $C_5H_{11}$ | $SO_2$ | a | — |
| 122 | H | H | H | $CH_3(O(CH_2)_2)_2$ | $CH_3(O(CH_2)_2)_2$ | S | a | — |
| 123 | H | H | H | $CH_3(O(CH_2)_2)_2$ | $CH_3(O(CH_2)_2)_2$ | S | b | — |
| 124 | H | H | H | $CH_3(O(CH_2)_2)_2$ | $CH_3(O(CH_2)_2)_2$ | S | c | — |
| 125 | H | H | H | $CH_3(O(CH_2)_2)_2$ | $CH_3(O(CH_2)_2)_2$ | S | m | — |
| 126 | H | $(CH)_2CH(CH_3)_2$ | $(CH)_2CH(CH_3)_2$ | H | H | S | a | — |
| 127 | H | $(CH)_2CH(CH_3)_2$ | $(CH)_2CH(CH_3)_2$ | H | H | S | b | — |
| 128 | H | $(CH)_2CH$ | $(CH)_2CH$ | H | H | S | c | 52–54 |

TABLE 1-continued

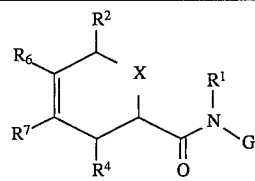

| Ex. No. | R¹ | R² | R⁴ | R⁶ | R⁷ | X | G | mp, °C. |
|---|---|---|---|---|---|---|---|---|
| 129 | H | (CH)₂CH(CH₃)₂ | (CH)₂CH(CH₃)₂ | H | H | S | m | — |
| 130 | H | C₆H₅ | C₆H₅ | H | H | O | a | — |
| 131 | H | C₆H₅ | C₆H₅ | H | H | O | b | — |
| 132 | H | C₆H₅ | C₆H₅ | H | H | S | c | 83–85 |
| 133 | H | C₆H₅ | C₆H₅ | H | H | O | m | — |
| 134 | H | CH₃ | CH₃ | H | H | S | a | — |
| 135 | H | CH₃ | CH₃ | H | H | S | b | — |
| 136 | H | CH₃ | CH₃ | H | H | S | c | 147–149 |
| 137 | H | CH₃ | CH₃ | H | H | S | m | — |
| 138 | H | C₃H₇ | C₃H₇ | H | H | S | a | — |
| 139 | H | C₃H₇ | C₃H₇ | H | H | S | b | — |
| 140 | H | C₃H₇ | C₃H₇ | H | H | S | c | oilʳ |
| 141 | H | C₃H₇ | C₃H₇ | H | H | S | m | — |
| 142 | H | C₄H₉ | C₄H₉ | H | H | S | a | — |
| 143 | H | C₄H₉ | C₄H₉ | H | H | S | b | — |
| 144 | H | C₄H₉ | C₄H₉ | H | H | S | c | 117–118 |
| 145 | H | C₄H₉ | C₄H₉ | H | H | S | m | — |
| 146 | H | C₆H₁₃ | C₆H₁₃ | H | H | S | a | — |
| 147 | H | C₆H₁₃ | C₆H₁₃ | H | H | S | b | — |
| 148 | H | C₆H₁₃ | C₆H₁₃ | H | H | S | c | oilˢ |
| 149 | H | C₆H₁₃ | C₆H₁₃ | H | H | S | m | — |
| 150 | H | C₁₀H₂₁ | C₁₀H₂₁ | H | H | S | a | — |
| 151 | H | C₁₀H₂₁ | C₁₀H₂₁ | H | H | S | b | — |
| 152 | H | C₁₀H₂₁ | C₁₀H₂₁ | H | H | S | c | — |
| 153 | H | C₁₀H₂₁ | C₁₀H₂₁ | H | H | S | m | — |
| 154 | H | CH₃OCH₂ | CH₃OCH₂ | H | H | S | a | — |
| 155 | H | CH₃OCH₂ | CH₃OCH₂ | H | H | S | b | — |
| 156 | H | CH₃OCH₂ | CH₃OCH₂ | H | H | S | c | — |
| 157 | H | CH₃OCH₂ | CH₃OCH₂ | H | H | S | m | — |
| 158 | H | C₈H₁₇ | C₈H₁₇ | H | H | S | a | — |
| 159 | H | C₈H₁₇ | C₈H₁₇ | H | H | S | b | — |
| 160 | H | C₈H₁₇ | C₈H₁₇ | H | H | S | c | oilᵗ |
| 161 | H | C₈H₁₇ | C₈H₁₇ | H | H | S | m | — |
| 162 | H | C₇H₁₅ | C₇H₁₅ | H | H | S | a | — |
| 163 | H | C₇H₁₅ | C₇H₁₅ | H | H | S | b | — |
| 164 | H | C₇H₁₅ | C₇H₁₅ | H | H | S | c | oilᵘ |
| 165 | H | C₇H₁₅ | C₇H₁₅ | H | H | S | m | — |
| 166 | H | H | CH₃CO₂ | H | H | S | a | — |
| 167 | H | H | CH₃CO₂ | H | H | S | b | — |
| 168 | H | H | CH₃CO₂ | H | H | S | c | 158–160 |
| 169 | H | H | CH₃CO₂ | H | H | S | m | — |
| 170 | H | CH₂OC₄H₉ | CH₂OC₄H₉ | H | H | S | a | — |
| 171 | H | CH₂OC₄H₉ | CH₂OC₄H₉ | H | H | S | b | — |
| 172 | H | CH₂OC₄H₉ | CH₂OC₄H₉ | H | H | S | c | — |
| 173 | H | CH₂OC₄H₉ | CH₂OC₄H₉ | H | H | S | m | — |
| 174 | H | CH₂S—(cC₆H₁₁) | CH₂S—(cC₆H₁₁) | H | H | S | a | — |
| 175 | H | CH₂S—(cC₆H₁₁) | CH₂S—(cC₆H₁₁) | H | H | S | b | — |
| 176 | H | CH₂S—(cC₆H₁₁) | CH₂S—(cC₆H₁₁) | H | H | S | c | — |
| 177 | H | CH₂S—(cC₆H₁₁) | CH₂S—(cC₆H₁₁) | H | H | S | m | — |
| 178 | H | (CH₂)₃Cl | (CH₂)₃Cl | H | H | S | a | — |
| 179 | H | (CH₂)₃Cl | (CH₂)₃Cl | H | H | S | b | — |
| 180 | H | (CH₂)₃Cl | (CH₂)₃Cl | H | H | S | c | 87–89 |
| 181 | H | (CH₂)₃Cl | (CH₂)₃Cl | H | H | S | m | — |
| 182 | H | (CH₂)₃S—(cC₆H₁₁) | (CH₂)₃S—(cC₆H₁₁) | H | H | S | a | — |
| 183 | H | (CH₂)₃S—(cC₆H₁₁) | (CH₂)₃S—(cC₆H₁₁) | H | H | S | b | — |
| 184 | H | (CH₂)₃S—(cC₆H₁₁) | (CH₂)₃S—(cC₆H₁₁) | H | H | S | c | oilᵛ |
| 185 | H | (CH₂)₃S—(cC₆H₁₁) | (CH₂)₃S—(cC₆H₁₁) | H | H | S | m | — |

TABLE 1-continued
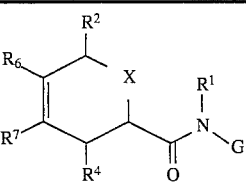
| Ex. No. | R¹ | R² | R⁴ | R⁶ | R⁷ | X | G | mp, °C. |
|---------|----|----|----|----|----|---|---|---------|
Key:
a: 2,6-di-isopropylphenyl (i-Pr, i-Pr)
b: 2,6-dimethylphenyl (Me, Me)
c: 2,6-dichlorophenyl (Cl, Cl)
d: 2,4-difluorophenyl (F, F)
e: 2-methylthio-6-methylpyridin-3-yl (MeS, Me)
f: 4,6-bis(methylthio)pyrimidin-5-yl (MeS, MeS)
g: 2-methylthiopyridin-3-yl (MeS)
h: 6-methylthiopyridin-3-yl (SMe)
i: 2-methylthio-6-methylthiopyridin-3-yl (MeS, SMe)

TABLE 1-continued

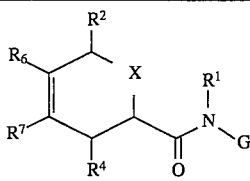

| Ex. No. | R¹ | R² | R⁴ | R⁶ | R⁷ | X | G | mp, °C. |
|---|---|---|---|---|---|---|---|---| j ![Br-pyrazole with N-Me]

k ![Me-pyrazole with N-Me and Me]

l ![pyrazole with N-Me and Me]

m ![MeS-pyrazole with N-Me and Me]

$^{n1}$H NMR(CDCl$_3$): δ8.95(1H, br s); 8.25(1H, dt, J=8.8, 6.2Hz); 6.90–6.81(2H, m); 3.80(1H, t, J=5.0Hz); 3.17(1H, d, J=15.0Hz); 3.07(1H, d, J=15.0Hz); 2.84(1H, dd, J=15.7, 4.8Hz); 2.47(1H, dd, J=15.7, 5.1Hz); 2.13–197(4H, m); 1.45–1.17(12H, m); 0.86(6H, t, J=6.8Hz). $^{13}$C NMR(CDCl$_3$): δ169.8, 158.6, 152.7, 132.6, 130.0, 128.3, 122.4, 111.1, 103.3, 44.4, 33.7, 33.0, 32.4, 32.0, 31.9, 28.3, 28.1, 27.9, 22.6(2C), 14.0(2C). IR (KBr):3 326, 2958, 2928, 1690, 1610, 1530, 1432, 1140, 1096, 964, 846 cm$^{-1}$. Mass spectrum(NH$_3$ CI/ DDIP): m/z 398(8%); 397(28%); 396(100%); 362(1%); 313(1%). Elemental analysis: calculated C 66.8, H 7.9, N 3.5; observed C 67.2, H 7.9, N 3.3.
$^{o1}$H NMR(CDCl$_3$): δ9.08(1H, br s); 8.32(1H, dd, J=8.0, 1.5Hz); 8.24(1H, dd, J=4.7, 1.5Hz); 7.05(1H, dd, J=8.0, 4.7Hz); 3.80(1H, t, J=5.0Hz); 3.28(1H, d, J=15.4Hz); 3.07(1H, d, J=15.4Hz); 2.87(1H, dd, J=15.9, 4.4Hz); 2.63(3H, s); 2.50(1H, dd, J=15.9, 5.5Hz); 2.20–2.02(4H, m); 1.43–1.20(12H, m; 0.86(3H, t, J=6.6Hz); 0.84(3H, t, J=6.9Hz). $^{13}$C NMR(CDCl$_3$): δ170.2, 149.3, 144.9, 132.3, 131.9, 129.6, 127.2, 119.8, 44.3, 33.8, 33.2, 32.2, 32.0, 31.9, 28.4, 28.1, 27.9, 22.6, 22.5, 14.1, 14.0, 13.5. IR(NaCl): 3280, 2955, 2926, 2857, 1688, 1578, 1566, 1510, 1467, 1450, 1387, 1291, 1204, 1086, 795, 738 cm$^{-1}$. Mass spectrum(NH$_3$ CI/ DDIP): m/z 409(13%); 408(27%); 407(100%); 329(1%). High-resolution mass spectrum: for C$_{22}$H$_{35}$N$_2$OS$_2$, calculated 407.2191 observed 407.2175, difference 3.9 ppm.
$^p$mp of major diastereomer 88–89° C.; mp of minor diastereomer 150–151° C.
$^{q1}$H NMR(CDCl$_3$): δ8.74(1H, br s); 6.65(1H, s); 5.88(1H, br d, J=11Hz); 5.49(1H, br d, J=11Hz); 4.09–4.00(1H, m); 3.74(1H, d, J=5Hz); 3.39–3.30(1H, m); 2.51(3H, s); 2.49(3H, s); 2.41(3H s); 1.80–1.25(16H, m); 0.91(3H, t, J=6Hz); 0.90(3H, t, J=6Hz).
$^r$Mixture of (2R*, 3S*, 6R*) and (2R*, 3R*, 6S*)isomers. For (2R*, 3S*, 6R*), $^1$H NMR(CDCl$_3$): δ8.31(1H, br s); 6.66(1H, s); 6.02–5.68 (2H, m); 3.93–3.83(1H, m); 3.46(1H, d, J=3Hz); 3.11–3.01(1H, m); 2.51(3H, s); 2.49(3H, s); 2.40(3H, s); 1.80–1.35(8H, m); 0.96(6H, t, J=6.4Hz). For (2R*, 3R*, 6S*), $^1$H NMR(CDCl$_3$): δ7.33(1H, br s); 6.66(1H, s); 6.02–5.68(2H, m); 4.03(1H, d, J=4.0Hz); 3.70–3.61(1H, m); 2.67–2.58(1H, m); 2. 50(3H, s); 2.48(3H, s); 2.39(3H, s); 1.80–1.35(8H, m); 0.96(6H, t, J=6.4Hz).
$^{s1}$H NMR(CDCl$_3$): 8.32(1H, br s); 6.65(1H, s); 5.81(1H, ddd, J=10.9, 5.2, 1.9Hz); 5.69(1H, dt, J=10.9, 1.8Hz); 3.90–3.82(1H, m); 3.45(1H, d, J=2.6Hz); 3.09–3.00(1H, m); 2.50(3H, s); 2.49(3H, s); 2.40(3H, s); 1.77–1.26(22H, m); 0.89(6H, t, J=7Hz).
$^t$Mixture of (2R*, 3S*, 6R*) and (2R*, 3R*, 6S*) isomers. For (2R*, 3S*, 6R*), $^1$H NMR(CDCl$_3$): δ8.32(1H, br s); 6.65(1H, s); 5.88–5.78(1H, m); 5.73–5.63(1H, m); 3.90–3.81(1H, m); 3.45(1H, d, J=2.6Hz); 3.07–2.99(1H, m); 2.50(3H, s); 2.49(3H, s);2.40(3H, s); 1.70–1.29(28H, m); 0.88(3H, t, J=6Hz); 0.87(3H, t, J=6Hz). For (2R*, 3R*, 6S*), $^1$H NMR(CDCl$_3$): δ7.33(1H, br s); 6.64(1H, s); 6.02–5.92(1H, m); 5.88–5.78(1H, m); 4.0 3(1H, d, J=4.4Hz); 3.69–3.60(1H, m); 2.67–2.58(1H, m); 2.50(3H, s); 2.48(3H, s); 2.40(3H, s); 1.70–1.20(28H, m); 0.87(3H, t, J=6Hz); 0.86(3H, t, J=6Hz).
$^{u1}$H NMR(CDCl$_3$): δ8.31(1H, br s); 6.64(1H, s); 5.81(1H, ddd, J=11.0, 4.3, 1.8Hz); 5.69(1H, d, J=11.0Hz); 3.90–3.81(1H, m); 3.45(1H, d, J=2.2Hz); 3.07–2.99(1H, m); 2.50(3H, s); 2.49(3H, s); 2.39(3H, s); 1.75–1.20(24H, m); 0.88(6H, t, J=6.3Hz).

TABLE 1-continued

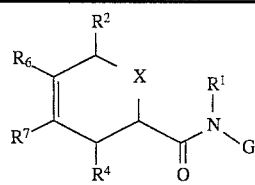

| Ex. No. | $R^1$ | $R^2$ | $R^4$ | $R^6$ | $R^7$ | X | G | mp, °C. |
|---|---|---|---|---|---|---|---|---|

$^v$ $^1$H NMR(CDCl$_3$): δ8.30(1H, br s); 6.65(1H, s); 5.81(1H, dt, J=11.3, 3Hz); 5.69(1H, d, J=11.3Hz); 3.93–3.84(1H, m); 3.46(1H, br s); 3.12–3.03(1H, m); 2.70–2.50(6H, m); 2.50(3H, s); 2.49(3H, s); 2.40(3H, s); 2.00–1.90(4H, m); 1.80–1.58(14H, m); 1.39–1.19(10H, m).

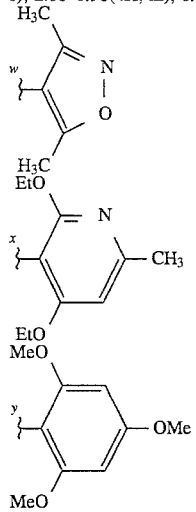

TABLE 2

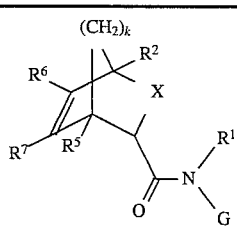

| Ex. No. | $R^1$ | $R^2$ | $R^4$ | $R^6$ | $R^7$ | k | X | G | mp, °C. |
|---|---|---|---|---|---|---|---|---|---|
| 186 | H | i-Pr | CH$_3$ | H | H | 2 | S | a | 177–178 |
| 187 | H | i-Pr | CH$_3$ | H | H | 2 | S | b | 159–160 |
| 188 | H | i-Pr | CH$_3$ | H | H | 2 | S | c | 140–141 |
| 189 | H | i-Pr | CH$_3$ | H | H | 2 | S | d | oil$^h$ |
| 190 | H | i-Pr | CH$_3$ | H | H | 2 | S | e | 149–150 |
| 191 | H | i-Pr | CH$_3$ | H | H | 2 | S | f | — |
| 192 | H | i-Pr | CH$_3$ | H | H | 2 | S | g | — |
| 193 | H | CH$_3$ | i-Pr | H | H | 2 | S | a | — |
| 194 | H | CH$_3$ | i-Pr | H | H | 2 | S | b | 155–156 |
| 195 | H | CH$_3$ | i-Pr | H | H | 2 | S | c | — |
| 196 | H | CH$_3$ | i-Pr | H | H | 2 | S | d | oil$^i$ |
| 197 | H | CH$_3$ | i-Pr | H | H | 2 | S | e | oil$^j$ |
| 198 | H | CH$_3$ | i-Pr | H | H | 2 | S | f | — |
| 199 | H | CH$_3$ | i-Pr | H | H | 2 | S | g | — |
| 200 | H | i-Pr | CH$_3$ | H | H | 2 | O | a | — |
| 201 | H | i-Pr | CH$_3$ | H | H | 2 | O | b | — |
| 202 | H | i-Pr | CH$_3$ | H | H | 2 | O | c | — |
| 203 | H | i-Pr | CH$_3$ | H | H | 2 | O | d | — |
| 204 | H | i-Pr | CH$_3$ | H | H | 2 | O | e | — |
| 205 | H | i-Pr | CH$_3$ | H | H | 2 | O | f | — |
| 206 | H | i-Pr | CH$_3$ | H | H | 2 | O | g | — |
| 207 | H | CH$_3$ | i-Pr | H | H | 2 | O | a | — |

TABLE 2-continued

| Ex. No. | $R^1$ | $R^2$ | $R^4$ | $R^6$ | $R^7$ | k | X | G | mp, °C. |
|---|---|---|---|---|---|---|---|---|---|
| 208 | H | CH$_3$ | i-Pr | H | H | 2 | O | b | — |
| 209 | H | CH$_3$ | i-Pr | H | H | 2 | O | c | — |
| 210 | H | CH$_3$ | i-Pr | H | H | 2 | O | d | — |
| 211 | H | CH$_3$ | i-Pr | H | H | 2 | O | e | — |
| 212 | H | CH$_3$ | i-Pr | H | H | 2 | O | f | — |
| 213 | H | CH$_3$ | i-Pr | H | H | 2 | O | g | — |
| 214 | H | C$_5$H$_{11}$ | C$_5$H$_{11}$ | H | H | 2 | S | a | — |
| 215 | H | C$_5$H$_{11}$ | C$_5$H$_{11}$ | H | H | 2 | S | b | — |
| 216 | H | C$_5$H$_{11}$ | C$_5$H$_{11}$ | H | H | 2 | S | c | — |
| 217 | H | C$_5$H$_{11}$ | C$_5$H$_{11}$ | H | H | 2 | S | d | — |
| 218 | H | C$_5$H$_{11}$ | C$_5$H$_{11}$ | H | H | 2 | S | e | — |
| 219 | H | C$_5$H$_{11}$ | C$_5$H$_{11}$ | H | H | 2 | S | f | — |
| 220 | H | C$_5$H$_{11}$ | C$_5$H$_{11}$ | H | H | 2 | S | g | — |
| 221 | H | H | H | C$_5$H$_{11}$ | C$_5$H$_{11}$ | 2 | S | a | — |
| 222 | H | H | H | C$_5$H$_{11}$ | C$_5$H$_{11}$ | 2 | S | b | — |
| 223 | H | H | H | C$_5$H$_{11}$ | C$_5$H$_{11}$ | 2 | S | c | — |
| 224 | H | H | H | C$_5$H$_{11}$ | C$_5$H$_{11}$ | 2 | S | d | — |
| 225 | H | H | H | C$_5$H$_{11}$ | C$_5$H$_{11}$ | 2 | S | e | — |
| 226 | H | H | H | C$_5$H$_{11}$ | C$_5$H$_{11}$ | 2 | S | f | — |
| 227 | H | H | H | C$_5$H$_{11}$ | C$_5$H$_{11}$ | 2 | S | g | — |
| 228 | H | C$_6$H$_5$ | C$_6$H$_5$ | C$_6$H$_5$ | C$_6$H$_5$ | 1 | O | a | — |
| 229 | H | C$_6$H$_5$ | C$_6$H$_5$ | C$_6$H$_5$ | C$_6$H$_5$ | 1 | O | b | — |
| 230 | H | C$_6$H$_5$ | C$_6$H$_5$ | C$_6$H$_5$ | C$_6$H$_5$ | 1 | O | c | — |
| 231 | H | C$_6$H$_5$ | C$_6$H$_5$ | C$_6$H$_5$ | C$_6$H$_5$ | 1 | O | d | — |
| 232 | H | C$_6$H$_5$ | C$_6$H$_5$ | C$_6$H$_5$ | C$_6$H$_5$ | 1 | O | e | — |
| 233 | H | C$_6$H$_5$ | C$_6$H$_5$ | C$_6$H$_5$ | C$_6$H$_5$ | 1 | O | f | — |
| 234 | H | C$_6$H$_5$ | C$_6$H$_5$ | C$_6$H$_5$ | C$_6$H$_5$ | 1 | O | g | — |
| 235 | H | i-Pr | CH$_3$ | H | H | 2 | SO$_2$ | a | — |
| 236 | H | i-Pr | CH$_3$ | H | H | 2 | SO$_2$ | b | — |
| 237 | H | i-Pr | CH$_3$ | H | H | 2 | SO$_2$ | c | — |
| 238 | H | i-Pr | CH$_3$ | H | H | 2 | SO$_2$ | d | — |
| 239 | CH$_3$ | i-Pr | CH$_3$ | H | H | 2 | S | e | — |
| 240 | CH$_3$ | i-Pr | CH$_3$ | H | H | 2 | S | f | — |
| 241 | CH$_3$ | i-Pr | CH$_3$ | H | H | 2 | S | g | — |
| 242 | H | CH$_3$ | i-Pr | H | H | 2 | SO | a | — |
| 243 | H | CH$_3$ | i-Pr | H | H | 2 | SO | b | — |
| 244 | H | CH$_3$ | i-Pr | H | H | 2 | SO | c | — |
| 245 | H | CH$_3$ | i-Pr | H | H | 2 | SO | d | — |
| 246 | H | CH$_3$ | CH$_3$ | H | H | 3 | S | e | — |
| 247 | H | CH$_3$ | CH$_3$ | H | H | 3 | S | f | — |
| 248 | H | H | H | H | H | 1 | S | a | — |
| 249 | H | H | H | H | H | 1 | S | b | 139–140 |
| 250 | H | H | H | H | H | 1 | S | c | — |
| 251 | H | H | H | H | H | 1 | S | d | — |
| 252 | H | H | H | H | H | 1 | S | e | 158–159 |
| 253 | H | H | H | H | H | 1 | S | f | — |
| 254 | H | H | H | H | H | 1 | S | g | — |
| 255 | H | H | H | H | H | 1 | O | a | — |
| 256 | H | H | H | H | H | 1 | O | b | — |
| 257 | H | H | H | H | H | 1 | O | c | — |
| 258 | H | H | H | H | H | 1 | O | d | — |
| 259 | H | H | H | H | H | 1 | O | e | — |
| 260 | H | H | H | H | H | 1 | O | f | — |
| 261 | H | H | H | H | H | 1 | O | g | — |
| 262 | H | H | H | H | H | 2 | S | a | — |
| 263 | H | H | H | H | H | 2 | S | b | — |
| 264 | H | H | H | H | H | 2 | S | c | — |
| 265 | H | H | H | H | H | 2 | S | d | — |
| 266 | H | H | H | H | H | 2 | S | e | — |
| 267 | H | H | H | H | H | 2 | S | f | — |
| 268 | H | H | H | H | H | 2 | S | g | — |
| 269 | H | H | H | H | H | 2 | O | a | — |
| 270 | H | H | H | H | H | 2 | O | b | — |
| 271 | H | H | H | H | H | 2 | O | c | — |
| 272 | H | H | H | H | H | 2 | O | d | — |

TABLE 2-continued

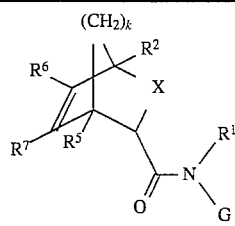

| Ex. No. | $R^1$ | $R^2$ | $R^4$ | $R^6$ | $R^7$ | k | X | G | mp, °C. |
|---|---|---|---|---|---|---|---|---|---|
| 273 | H | H | H | H | H | 2 | O | e | — |
| 274 | H | H | H | H | H | 2 | O | f | — |
| 275 | H | H | H | H | H | 2 | O | g | — |
| 276 | H | H | OCH$_3$ | H | H | 2 | S | a | — |
| 277 | H | H | OCH$_3$ | H | H | 2 | S | b | 147–148 |
| 278 | H | H | OCH$_3$ | H | H | 2 | S | c | — |
| 279 | H | H | OCH$_3$ | H | H | 2 | S | d | — |
| 280 | H | H | OCH$_3$ | H | H | 2 | S | e | 75–77 |
| 281 | H | H | OCH$_3$ | H | H | 2 | S | f | — |
| 282 | H | H | OCH$_3$ | H | H | 2 | S | g | — |
| 283 | H | H | OCH$_3$ | H | H | 2 | O | a | — |
| 284 | H | H | OCH$_3$ | H | H | 2 | O | b | — |
| 285 | H | H | OCH$_3$ | H | H | 2 | O | c | — |
| 286 | H | H | OCH$_3$ | H | H | 2 | O | d | — |
| 287 | H | H | OCH$_3$ | H | H | 2 | O | e | — |
| 288 | H | H | OCH$_3$ | H | H | 2 | O | f | — |
| 289 | H | H | OCH$_3$ | H | H | 2 | O | g | — |
| 290 | H | OCH$_3$ | H | H | H | 2 | S | a | — |
| 291 | H | OCH$_3$ | H | H | H | 2 | S | b | — |
| 292 | H | OCH$_3$ | H | H | H | 2 | S | c | — |
| 293 | H | OCH$_3$ | H | H | H | 2 | S | d | — |
| 294 | H | OCH$_3$ | H | H | H | 2 | S | e | 72–74 |
| 295 | H | OCH$_3$ | H | H | H | 2 | S | f | — |
| 296 | H | OCH$_3$ | H | H | H | 2 | S | g | — |

Key:

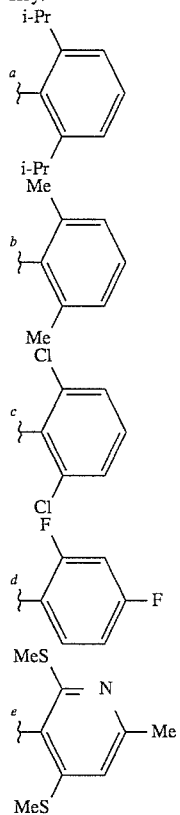

TABLE 2-continued

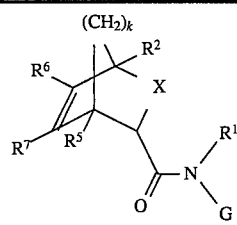

| Ex. No. | R¹ | R² | R⁴ | R⁶ | R⁷ | k | X | G | mp, °C. |
|---|---|---|---|---|---|---|---|---|---|

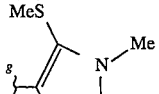

$^h$¹H NMR(CDCl$_3$): δ8.29(1H, br s); 8.22(1H, dt, J=8.8, 5.8Hz); 6.91–6.80(2H, m); 6.58(1H, d, J=8.8Hz); 5.92(1H, d, J=8.8Hz); 3.81(1H, s); 2.18–2.05(2H, m); 1.80–1.60(2H, m); 1.44(3H, s); 1.43–1.33(1H, m); 1.15(3H, d, J=6.6Hz); 1.13(3H, d, J=7.0Hz). ¹³C NMR(CDCl$_3$): δ169.2, 158.2, 152.4, 136.9, 135.1, 122.8, 122.0, 111.0, 103.5, 59.8, 52.5, 38.0, 34.3, 33.7, 33.3, 24.6, 18.9, 18.7. Mass spectrum(NH$_3$—CI/DDIP): m/z 340(7%); 339(22%); 338(100%); 137(3%).
$^i$¹H NMR(CDCl$_3$): δ8.23–8.12(2H, m); 6.88–6.79(2H, m); 6.52(1H, d, J=8.8Hz); 5.99(1H, d, J=8.8Hz); 4.22(1H, s); 2.23–2.03(2H, m); 1.67–1.44(3H, m); 1.57(3H, s); 1.13(3H, d, J=6.6Hz); 1.01(3H, d, J=7.0Hz). ¹³C NMR(CDCl$_3$): δ169.1, 140.2, 133.8, 122.3, 110.0, 103.3, 57.8, 45.3, 43.5, 38.1, 32.0, 24.2, 23.2, 19.4, 16.7. Mass spectrum(NH$_3$—CI/DDIP): m/z 340(7%); 339(21%); 338(100%); 255(1%); 137(3%).
$^j$¹H NMR(CDCl$_3$): δ7.46(1H, br s); 6.60(1H, s); 6.49(1H, d, J=8.8Hz); 6.28(1H, d, J=8.8Hz); 4.29(1H, s); 2.49(3H, s); 2.46(3H, s); 2.39(3H, s); 2.17–2.03(2H, m); 1.81–1.40(3H, m); 1.55(3H, s); 1.11(3H, d, J=6.6Hz); 1.04(3H, d, J=6.6Hz). ¹³C NMR(CDCl$_3$): δ175.4, 156.6, 154.0, 149.8, 139.6, 134.9, 120.2, 113.5, 57.7, 50.0, 38.2, 31.6, 30.0, 24.5, 24.2, 23.0, 19.6, 16.8, 14.1, 13.0. Mass spectrum(NH$_3$—CI/DDIP): m/z 411(15%); 410(23%) ; 409(100%); 275(7%); 227(7%).

TABLE 3

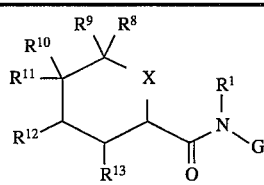

| Ex. No. | R¹ | R⁸ | R⁹ | R¹⁰ | R¹¹ | R¹² | R¹³ | X | G | mp, °C. |
|---|---|---|---|---|---|---|---|---|---|---|
| 297 | H | H | H | C₇H₁₅ | H | C₇H₁₅ | H | S | a | — |
| 298 | H | H | H | C₇H₁₅ | H | C₇H₁₅ | H | S | b | — |
| 299 | H | H | H | C₇H₁₅ | H | C₇H₁₅ | H | S | c | — |
| 300 | H | H | H | C₇H₁₅ | H | C₇H₁₅ | H | S | d | — |
| 301 | H | H | H | C₇H₁₅ | H | C₇H₁₅ | H | S | e | — |
| 302 | H | H | H | C₇H₁₅ | H | C₇H₁₅ | H | S | f | — |
| 303 | H | H | H | C₇H₁₅ | H | C₇H₁₅ | H | S | g | — |
| 304 | H | H | H | C₇H₁₅ | H | C₇H₁₅ | H | S | h | — |
| 305 | H | H | H | C₇H₁₅ | H | C₇H₁₅ | H | S | i | — |
| 306 | H | H | H | C₇H₁₅ | H | C₇H₁₅ | H | S | j | — |
| 307 | H | H | H | C₇H₁₅ | H | C₇H₁₅ | H | S | k | — |
| 308 | H | H | H | C₇H₁₅ | H | C₇H₁₅ | H | S | l | — |
| 309 | H | H | H | C₇H₁₅ | H | C₇H₁₅ | H | S | m | — |
| 310 | H | C₇H₁₅ | H | H | H | H | C₇H₁₅ | S | a | — |
| 311 | H | C₇H₁₅ | H | H | H | H | C₇H₁₅ | S | b | — |
| 312 | H | C₇H₁₅ | H | H | H | H | C₇H₁₅ | S | c | — |
| 313 | H | C₇H₁₅ | H | H | H | H | C₇H₁₅ | S | d | — |
| 314 | H | C₇H₁₅ | H | H | H | H | C₇H₁₅ | S | e | — |
| 315 | H | C₇H₁₅ | H | H | H | H | C₇H₁₅ | S | f | — |
| 316 | H | C₇H₁₅ | H | H | H | H | C₇H₁₅ | S | g | — |

TABLE 3-continued

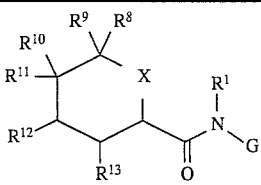

| Ex. No. | $R^1$ | $R^8$ | $R^9$ | $R^{10}$ | $R^{11}$ | $R^{12}$ | $R^{13}$ | X | G | mp, °C. |
|---|---|---|---|---|---|---|---|---|---|---|
| 317 | H | $C_7H_{15}$ | H | H | H | H | $C_7H_{15}$ | S | h | — |
| 318 | H | $C_7H_{15}$ | H | H | H | H | $C_7H_{15}$ | S | i | — |
| 319 | H | $C_7H_{15}$ | H | H | H | H | $C_7H_{15}$ | S | j | — |
| 320 | H | $C_7H_{15}$ | H | H | H | H | $C_7H_{15}$ | S | k | — |
| 321 | H | $C_7H_{15}$ | H | H | H | H | $C_7H_{15}$ | S | l | — |
| 322 | H | $C_7H_{15}$ | H | H | H | H | $C_7H_{15}$ | S | m | — |
| 323 | H | H | H | $C_7H_{15}$ | H | $C_7H_{15}$ | H | O | a | — |
| 324 | H | H | H | $C_7H_{15}$ | H | $C_7H_{15}$ | H | O | b | — |
| 325 | H | H | H | $C_7H_{15}$ | H | $C_7H_{15}$ | H | O | c | — |
| 326 | H | H | H | $C_7H_{15}$ | H | $C_7H_{15}$ | H | O | d | — |
| 327 | H | H | H | $C_7H_{15}$ | H | $C_7H_{15}$ | H | O | e | — |
| 328 | H | H | H | $C_7H_{15}$ | H | $C_7H_{15}$ | H | O | f | — |
| 329 | H | H | H | $C_7H_{15}$ | H | $C_7H_{15}$ | H | O | g | — |
| 330 | H | H | H | $C_7H_{15}$ | H | $C_7H_{15}$ | H | O | h | — |
| 331 | H | H | H | $C_7H_{15}$ | H | $C_7H_{15}$ | H | O | i | — |
| 332 | H | H | H | $C_7H_{15}$ | H | $C_7H_{15}$ | H | O | j | — |
| 333 | H | H | H | $C_7H_{15}$ | H | $C_7H_{15}$ | H | O | k | — |
| 334 | H | H | H | $C_7H_{15}$ | H | $C_7H_{15}$ | H | O | l | — |
| 335 | H | H | H | $C_7H_{15}$ | H | $C_7H_{15}$ | H | O | m | — |
| 336 | H | $C_7H_{15}$ | H | H | H | H | $C_7H_{15}$ | O | a | — |
| 337 | H | $C_7H_{15}$ | H | H | H | H | $C_7H_{15}$ | O | b | — |
| 338 | H | $C_7H_{15}$ | H | H | H | H | $C_7H_{15}$ | O | c | — |
| 339 | H | $C_7H_{15}$ | H | H | H | H | $C_7H_{15}$ | O | d | — |
| 340 | H | $C_7H_{15}$ | H | H | H | H | $C_7H_{15}$ | O | e | — |
| 341 | H | $C_7H_{15}$ | H | H | H | H | $C_7H_{15}$ | O | f | — |
| 342 | H | $C_7H_{15}$ | H | H | H | H | $C_7H_{15}$ | O | g | — |
| 343 | H | $C_7H_{15}$ | H | H | H | H | $C_7H_{15}$ | O | h | — |
| 344 | H | $C_7H_{15}$ | H | H | H | H | $C_7H_{15}$ | O | i | — |
| 345 | H | $C_7H_{15}$ | H | H | H | H | $C_7H_{15}$ | O | j | — |
| 346 | H | $C_7H_{15}$ | H | H | H | H | $C_7H_{15}$ | O | k | — |
| 347 | H | $C_7H_{15}$ | H | H | H | H | $C_7H_{15}$ | O | l | — |
| 348 | H | $C_7H_{15}$ | H | H | H | H | $C_7H_{15}$ | O | m | — |
| 349 | H | H | H | $C_8H_{17}$ | H | $C_8H_{17}$ | H | S | a | — |
| 350 | H | H | H | $C_8H_{17}$ | H | $C_8H_{17}$ | H | S | b | — |
| 351 | H | H | H | $C_8H_{17}$ | H | $C_8H_{17}$ | H | S | c | — |
| 352 | H | H | H | $C_8H_{17}$ | H | $C_8H_{17}$ | H | S | d | — |
| 353 | H | H | H | $C_8H_{17}$ | H | $C_8H_{17}$ | H | S | e | — |
| 354 | H | H | H | $C_8H_{17}$ | H | $C_8H_{17}$ | H | S | f | — |
| 355 | H | H | H | $C_8H_{17}$ | H | $C_8H_{17}$ | H | S | g | — |
| 356 | H | H | H | $C_8H_{17}$ | H | $C_8H_{17}$ | H | S | h | — |
| 357 | H | H | H | $C_8H_{17}$ | H | $C_8H_{17}$ | H | S | i | — |
| 358 | H | H | H | $C_8H_{17}$ | H | $C_8H_{17}$ | H | S | j | — |
| 359 | H | H | H | $C_8H_{17}$ | H | $C_8H_{17}$ | H | S | k | — |
| 360 | H | H | H | $C_8H_{17}$ | H | $C_8H_{17}$ | H | S | l | — |
| 361 | H | H | H | $C_8H_{17}$ | H | $C_8H_{17}$ | H | S | m | — |
| 362 | H | $C_8H_{17}$ | H | H | H | H | $C_8H_{17}$ | S | a | — |
| 363 | H | $C_8H_{17}$ | H | H | H | H | $C_8H_{17}$ | S | b | — |
| 364 | H | $C_8H_{17}$ | H | H | H | H | $C_8H_{17}$ | S | c | — |
| 365 | H | $C_8H_{17}$ | H | H | H | H | $C_8H_{17}$ | S | d | — |
| 366 | H | $C_8H_{17}$ | H | H | H | H | $C_8H_{17}$ | S | e | — |
| 367 | H | $C_8H_{17}$ | H | H | H | H | $C_8H_{17}$ | S | f | — |
| 368 | H | $C_8H_{17}$ | H | H | H | H | $C_8H_{17}$ | S | g | — |
| 369 | H | $C_8H_{17}$ | H | H | H | H | $C_8H_{17}$ | S | h | — |
| 370 | H | $C_8H_{17}$ | H | H | H | H | $C_8H_{17}$ | S | i | — |
| 371 | H | $C_8H_{17}$ | H | H | H | H | $C_8H_{17}$ | S | j | — |
| 372 | H | $C_8H_{17}$ | H | H | H | H | $C_8H_{17}$ | S | k | — |
| 373 | H | $C_8H_{17}$ | H | H | H | H | $C_8H_{17}$ | S | l | — |
| 374 | H | $C_8H_{17}$ | H | H | H | H | $C_8H_{17}$ | S | m | — |
| 375 | H | H | H | $C_8H_{17}$ | H | $C_8H_{17}$ | H | O | a | — |
| 376 | H | H | H | $C_8H_{17}$ | H | $C_8H_{17}$ | H | O | b | — |
| 377 | H | H | H | $C_8H_{17}$ | H | $C_8H_{17}$ | H | O | c | — |
| 378 | H | H | H | $C_8H_{17}$ | H | $C_8H_{17}$ | H | O | d | — |
| 379 | H | H | H | $C_8H_{17}$ | H | $C_8H_{17}$ | H | O | e | — |
| 380 | H | H | H | $C_8H_{17}$ | H | $C_8H_{17}$ | H | O | f | — |
| 381 | H | H | H | $C_8H_{17}$ | H | $C_8H_{17}$ | H | O | g | — |
| 382 | H | H | H | $C_8H_{17}$ | H | $C_8H_{17}$ | H | O | h | — |
| 383 | H | H | H | $C_8H_{17}$ | H | $C_8H_{17}$ | H | O | i | — |

TABLE 3-continued

Structure: cyclohexane ring with R⁸, R⁹ on one carbon; R¹⁰, R¹¹ on next; R¹² on next; R¹³ on next; X linked to carbon bearing CH(—)C(=O)—N(R¹)—G

| Ex. No. | R¹ | R⁸ | R⁹ | R¹⁰ | R¹¹ | R¹² | R¹³ | X | G | mp, °C. |
|---|---|---|---|---|---|---|---|---|---|---|
| 384 | H | H | H | C₈H₁₇ | H | C₈H₁₇ | H | O | j | — |
| 385 | H | H | H | C₈H₁₇ | H | C₈H₁₇ | H | O | k | — |
| 386 | H | H | H | C₈H₁₇ | H | C₈H₁₇ | H | O | l | — |
| 387 | H | H | H | C₈H₁₇ | H | C₈H₁₇ | H | O | m | — |
| 388 | H | C₈H₁₇ | H | H | H | H | C₈H₁₇ | O | a | — |
| 389 | H | C₈H₁₇ | H | H | H | H | C₈H₁₇ | O | b | — |
| 390 | H | C₈H₁₇ | H | H | H | H | C₈H₁₇ | O | c | — |
| 391 | H | C₈H₁₇ | H | H | H | H | C₈H₁₇ | O | d | — |
| 392 | H | C₈H₁₇ | H | H | H | H | C₈H₁₇ | O | e | — |
| 393 | H | C₈H₁₇ | H | H | H | H | C₈H₁₇ | O | f | — |
| 394 | H | C₈H₁₇ | H | H | H | H | C₈H₁₇ | O | g | — |
| 395 | H | C₈H₁₇ | H | H | H | H | C₈H₁₇ | O | h | — |
| 396 | H | C₈H₁₇ | H | H | H | H | C₈H₁₇ | O | i | — |
| 397 | H | C₈H₁₇ | H | H | H | H | C₈H₁₇ | O | j | — |
| 398 | H | C₈H₁₇ | H | H | H | H | C₈H₁₇ | O | k | — |
| 399 | H | C₈H₁₇ | H | H | H | H | C₈H₁₇ | O | L | — |
| 400 | H | SC₆H₁₃ | H | H | H | O= | H | S | a | — |
| 401 | H | SC₆H₁₃ | H | H | H | O= | H | S | b | — |
| 402 | H | SC₆H₁₃ | H | H | H | O= | H | S | c | 175–177 |
| 403 | H | SC₆H₁₃ | H | H | H | O= | H | S | m | — |
| 404 | H | OC₆H₁₃ | H | H | H | O= | H | S | a | — |
| 405 | H | OC₆H₁₃ | H | H | H | O= | H | S | b | — |
| 406 | H | OC₆H₁₃ | H | H | H | O= | H | S | c | — |
| 407 | H | OC₆H₁₃ | H | H | H | O= | H | S | m | — |
| 408 | H | SC₆H₁₃ | H | H | H | O= | H | O | a | — |
| 409 | H | SC₆H₁₃ | H | H | H | O= | H | O | b | — |
| 410 | H | SC₆H₁₃ | H | H | H | O= | H | O | c | — |
| 411 | H | SC₆H₁₃ | H | H | H | O= | H | O | m | — |
| 412 | H | OC₆H₁₃ | H | H | H | O= | H | O | a | — |
| 413 | H | OC₆H₁₃ | H | H | H | O= | H | O | b | — |
| 414 | H | OC₆H₁₃ | H | H | H | O= | H | O | c | — |
| 415 | H | OC₆H₁₃ | H | H | H | O= | H | O | m | — |
| 416 | H | C₆H₁₃ | H | H | H | O= | H | S | a | — |
| 417 | H | C₆H₁₃ | H | H | H | O= | H | S | b | — |
| 418 | H | C₆H₁₃ | H | H | H | O= | H | S | c | — |
| 419 | H | C₆H₁₃ | H | H | H | O= | H | S | m | — |
| 420 | H | C₆H₁₃ | H | H | H | O= | H | O | a | — |
| 421 | H | C₆H₁₃ | H | H | H | O= | H | O | b | — |
| 422 | H | C₆H₁₃ | H | H | H | O= | H | O | c | — |
| 423 | H | C₆H₁₃ | H | H | H | O= | H | O | m | — |
| 424 | H | CH₃O | H | C₄H₉O | H | C₄H₉O | C₆H₅CH₂O | O | a | — |
| 425 | H | CH₃O | H | C₄H₉O | H | C₄H₉O | C₆H₅CH₂O | O | b | — |
| 426 | H | CH₃O | H | C₄H₉O | H | C₄H₉O | C₆H₅CH₂O | O | c | oilⁿ |
| 427 | H | CH₃O | H | C₄H₉O | H | C₄H₉O | C₆H₅CH₂O | O | m | — |
| 428 | H | CH₃O | H | C₄H₉O | H | C₄H₉O | C₆H₅CH₂O | S | a | — |
| 429 | H | CH₃O | H | C₄H₉O | H | C₄H₉O | C₆H₅CH₂O | S | b | — |
| 430 | H | CH₃O | H | C₄H₉O | H | C₄H₉O | C₆H₅CH₂O | S | c | — |
| 431 | H | CH₃O | H | C₄H₉O | H | C₄H₉O | C₆H₅CH₂O | S | m | — |
| 432 | H | CH₃O | H | C₄H₉O | H | C₄H₉O | C₄H₉O | O | a | — |
| 433 | H | CH₃O | H | C₄H₉O | H | C₄H₉O | C₄H₉O | O | b | — |
| 434 | H | CH₃O | H | C₄H₉O | H | C₄H₉O | C₄H₉O | O | c | oilº |
| 435 | H | CH₃O | H | C₄H₉O | H | C4H90 | C₄H₉O | O | m | — |
| 436 | H | CH₃O | H | C₄H₉O | H | C₄H₉O | C₄H₉O | S | a | — |
| 437 | H | CH₃O | H | C₄H₉O | H | C₄H₉O | C₄H₉O | S | b | — |
| 438 | H | CH₃O | H | C₄H₉O | H | C₄H₉O | C₄H₉O | S | c | — |
| 439 | H | CH₃O | H | C₄H₉O | H | C₄H₉O | C₄H₉O | S | m | — |
| 440 | H | H | H | C₄H₉O | H | C₄H₉O | C₆H₅CH₂O | O | a | — |
| 441 | H | H | H | C₄H₉O | H | C₄H₉O | C₆H₅CH₂O | O | b | — |
| 442 | H | H | H | C₄H₉O | H | C₄H₉O | C₆H₅CH₂O | O | c | oilᵖ |
| 443 | H | H | H | C₄H₉O | H | C₄H₉O | C₆H₅CH₂O | O | m | — |
| 444 | H | H | H | C₄H₉O | H | C₄H₉O | C₆H₅CH₂O | S | a | — |
| 445 | H | H | H | C₄H₉O | H | C₄H₉O | C₆H₅CH₂O | S | b | — |
| 446 | H | H | H | C₄H₉O | H | C₄H₉O | C₆H₅CH₂O | S | c | — |
| 447 | H | H | H | C₄H₉O | H | C₄H₉O | C₆H₅CH₂O | S | m | — |
| 448 | H | CH₃CO₂ | H | CH₃CO₂ | H | CH₃CO₂ | CH₃CO₂ | O | a | — |
| 449 | H | CH₃CO₂ | H | CH₃CO₂ | H | CH₃CO₂ | CH₃CO₂ | O | b | — |
| 450 | H | CH₃CO₂ | H | CH₃CO₂ | H | CH₃CO₂ | CH₃CO₂ | O | c | — |

TABLE 3-continued

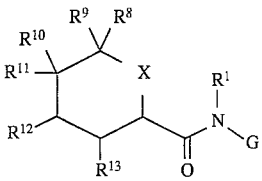

| Ex. No. | R¹ | R⁸ | R⁹ | R¹⁰ | R¹¹ | R¹² | R¹³ | X | G | mp, °C. |
|---|---|---|---|---|---|---|---|---|---|---|
| 451 | H | $CH_3CO_2$ | H | $CH_3CO_2$ | H | $CH_3CO_2$ | $CH_3CO_2$ | O | m | — |
| 452 | H | $C_6H_{13}S$ | H | $CH_3CO_2$ | H | $CH_3CO_2$ | $CH_3CO_2$ | O | a | — |
| 453 | H | $C_6H_{13}S$ | H | $CH_3CO_2$ | H | $CH_3CO_2$ | $CH_3CO_2$ | O | b | — |
| 454 | H | $C_6H_{13}S$ | H | $CH_3CO_2$ | H | $CH_3CO_2$ | $CH_3CO_2$ | O | c | — |
| 455 | H | $C_6H_{13}S$ | H | $CH_3CO_2$ | H | $CH_3CO_2$ | $CH_3CO_2$ | O | m | — |
| 456 | H | H | H | $C_4H_9O$ | H | $C_4H_9O$ | $C_4H_9O$ | O | a | — |
| 457 | H | H | H | $C_4H_9O$ | H | $C_4H_9O$ | $C_4H_9O$ | O | b | — |
| 458 | H | H | H | $C_4H_9O$ | H | $C_4H_9O$ | $C_4H_9O$ | O | c | oil$^q$ |
| 459 | H | H | H | $C_4H_9O$ | H | $C_4H_9O$ | $C_4H_9O$ | O | m | — |
| 460 | H | H | H | $C_4H_9O$ | H | $C_4H_9O$ | $C_4H_9O$ | S | a | — |
| 461 | H | H | H | $C_4H_9O$ | H | $C_4H_9O$ | $C_4H_9O$ | S | b | — |
| 462 | H | H | H | $C_4H_9O$ | H | $C_4H_9O$ | $C_4H_9O$ | S | c | — |
| 463 | H | H | H | $C_4H_9O$ | H | $C_4H_9O$ | $C_4H_9O$ | S | m | — |
| 464 | H | H | H | $C_7H_{15}O$ | H | $C_7H_{15}O$ | $C_4H_9O$ | O | a | — |
| 465 | H | H | H | $C_7H_{15}O$ | H | $C_7H_{15}O$ | $C_4H_9O$ | O | b | — |
| 466 | H | H | H | $C_7H_{15}O$ | H | $C_7H_{15}O$ | $C_4H_9O$ | O | c | — |
| 467 | H | H | H | $C_7H_{15}O$ | H | $C_7H_{15}O$ | $C_4H_9O$ | O | m | — |
| 468 | H | H | H | $C_7H_{15}O$ | H | $C_7H_{15}O$ | $C_4H_9O$ | S | a | — |
| 469 | H | H | H | $C_7H_{15}O$ | H | $C_7H_{15}O$ | $C_4H_9O$ | S | b | — |
| 470 | H | H | H | $C_7H_{15}O$ | H | $C_7H_{15}O$ | $C_4H_9O$ | S | c | — |
| 471 | H | H | H | $C_7H_{15}O$ | H | $C_7H_{15}O$ | $C_4H_9O$ | S | m | — |

Key:

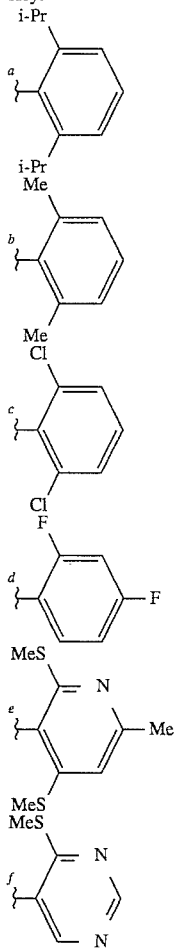

TABLE 3-continued

[Structure: R⁹, R⁸ on a ring with R¹⁰, R¹¹, R¹², R¹³ substituents, X linker to CH-C(=O)-N(R¹)-G]

| Ex. No. | R¹ | R⁸ | R⁹ | R¹⁰ | R¹¹ | R¹² | R¹³ | X | G | mp, °C. |
|---|---|---|---|---|---|---|---|---|---|---| g: [3-(MeS)pyridin-2-yl group]

h: [6-(SMe)pyridin-3-yl group]

i: [3-MeS,6-SMe-pyridin-2-yl group]

j: [4-Br-1-methyl-pyrazol-5-yl group]

k: [1,3,5-trimethyl-pyrazol-4-yl group]

l: [1,3-dimethyl-pyrazol-5-yl group]

m: [4-MeS-1,3-dimethyl-pyrazol-5-yl group] with Me

ⁿ¹H NMR(300MHz, CDCl₃): δ7.52(1H, s); 7.41(2H, d, J=6.2Hz); 7.29–7.21(3H, m); 6.65(1H, s); 4.92(1H, d, J=9.9Hz, A of AB); 4.92(1H, d, J=3.7Hz); 4.74(1H, d, J=9.9Hz, B of AB); 4.30–4.27(1H, m); 3.87–3.72(4H, m); 3.64(2H, t, J=6.8Hz); 3.47(3H, s); 3.41–3.36(1H, m); 2.48(6H, s); 2.37(3H, s); 1.64–1.53(4H, m); 1.42–1.33(4H, m); 0.92(3H, t, J=7.32Hz); 0.90(3H, t, J=7.32Hz).

ᵒ¹H NMR(300MHz, CDCl₃): δ7.49(1H, s); 6.64(1H, s); 4.88(1H, d, J=3.3Hz); 4.18(1H, d, J=9.89Hz); 3.83–3.70(4H, m); 3.68–3.60(3H, m); 3.51(1H, d, J=9.89Hz); 3.46(3H, s); 3.33(1H, dd, J=10.7, 3.48Hz); 2.49(3H, s); 2.47(3H, s); 2.39(3H, s); 1.62–1.49(6H, m); 0.91(6H, t, J=7.32Hz); 0.85(3H, t, J=7.32Hz).

ᵖ¹H NMR(300MHz, CDCl₃): δ7.53(1H, s); 7.41(1H, d, J=6.59Hz); 7.30(1H, s); 7.30–7.20(3H, m); 6.64(1H, s); 4.91(1H, d, J=9,89Hz, A of AB); 4.72(1H, d, J=9.89Hz, B of AB); 4.13(1H, dd, J=10.99, 4.03Hz); 3.93(1H, d, J=9.52Hz); 3.82–3.77(2H, m); 3.72(1H, t, J=8.72Hz); 3.64–3.59(2H, m); 3.44–3.37(2H, m); 3.23(1H, t, J=10.43Hz); 2.48(6H, s); 2.37(3H, s); 1.64–1.45(4H, m); 1.43–1.31(4H, m); 0.92(3H, t, J=7.32Hz); 0.91(3H, t, J=7.32Hz).

ᑫ¹H NMR(300MHz, CDCl₃): δ7.52(1H, s); 6.65(1H, s); 4.12(1H, dd, J=11.17, 4.94Hz); 3.83–3.67(4H, m); 3.64–3.54(2H, m); 3.49(1H, t, J=4.63Hz); 3.46–3.18(3H, m); 2.50(3H, s); 2.48(3H, s); 2.40(3H, s); 1.65–1.50(6H, m), 1.47–1.25(6H, m), 0.96–0.84(9H, m).

TABLE 4

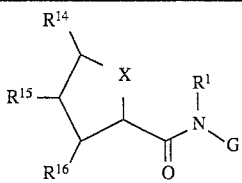

| Ex. No. | $R^1$ | $R^{14}$ | $R^{15}$ | $R^{16}$ | X | G | m.p. |
|---|---|---|---|---|---|---|---|
| 472 | H | $C_7H_{15}$ | $C_7H_{15}$ | H | S | a | — |
| 473 | H | $C_7H_{15}$ | $C_7H_{15}$ | H | S | b | — |
| 474 | H | $C_7H_{15}$ | $C_7H_{15}$ | H | S | c | — |
| 475 | H | $C_7H_{15}$ | $C_7H_{15}$ | H | S | d | — |
| 476 | H | $C_7H_{15}$ | $C_7H_{15}$ | H | S | e | — |
| 477 | H | $C_7H_{15}$ | $C_7H_{15}$ | H | S | f | — |
| 478 | H | $C_7H_{15}$ | $C_7H_{15}$ | H | S | g | — |
| 479 | H | $C_7H_{15}$ | $C_7H_{15}$ | H | S | h | — |
| 480 | H | $C_7H_{15}$ | $C_7H_{15}$ | H | S | i | — |
| 481 | H | $C_7H_{15}$ | $C_7H_{15}$ | H | S | j | — |
| 482 | H | $C_7H_{15}$ | $C_7H_{15}$ | H | S | k | — |
| 483 | H | $C_7H_{15}$ | $C_7H_{15}$ | H | S | l | — |
| 484 | H | $C_7H_{15}$ | $C_7H_{15}$ | H | S | m | — |
| 485 | H | $C_7H_{15}$ | $C_7H_{15}$ | H | SO | a | — |
| 486 | H | $C_7H_{15}$ | $C_7H_{15}$ | H | SO | b | — |
| 487 | H | $C_7H_{15}$ | $C_7H_{15}$ | H | SO | c | — |
| 488 | H | $C_7H_{15}$ | $C_7H_{15}$ | H | SO | m | — |
| 489 | H | $C_7H_{15}$ | $C_7H_{15}$ | H | $SO_2$ | a | — |
| 490 | H | $C_7H_{15}$ | $C_7H_{15}$ | H | $SO_2$ | b | — |
| 491 | H | $C_7H_{15}$ | $C_7H_{15}$ | H | $SO_2$ | c | — |
| 492 | H | $C_7H_{15}$ | $C_7H_{15}$ | H | $SO_2$ | m | — |
| 493 | $CH_3$ | $C_7H_{15}$ | $C_7H_{15}$ | H | S | a | — |
| 494 | $CH_3$ | $C_7H_{15}$ | $C_7H_{15}$ | H | S | b | — |
| 495 | $CH_3$ | $C_7H_{15}$ | $C_7H_{15}$ | H | S | c | — |
| 496 | $CH_3$ | $C_7H_{15}$ | $C_7H_{15}$ | H | S | m | — |
| 497 | H | $C_7H_{15}$ | H | $C_7H_{15}$ | S | a | — |
| 498 | H | $C_7H_{15}$ | H | $C_7H_{15}$ | S | b | — |
| 499 | H | $C_7H_{15}$ | H | $C_7H_{15}$ | S | c | — |
| 500 | H | $C_7H_{15}$ | H | $C_7H_{15}$ | S | d | — |
| 501 | H | $C_7H_{15}$ | H | $C_7H_{15}$ | S | e | — |
| 502 | H | $C_7H_{15}$ | H | $C_7H_{15}$ | S | f | — |
| 503 | H | $C_7H_{15}$ | H | $C_7H_{15}$ | S | g | — |
| 504 | H | $C_7H_{15}$ | H | $C_7H_{15}$ | S | h | — |
| 505 | H | $C_7H_{15}$ | H | $C_7H_{15}$ | S | i | — |
| 506 | H | $C_7H_{15}$ | H | $C_7H_{15}$ | S | j | — |
| 507 | H | $C_7H_{15}$ | H | $C_7H_{15}$ | S | k | — |
| 508 | H | $C_7H_{15}$ | H | $C_7H_{15}$ | S | l | — |
| 509 | H | $C_7H_{15}$ | H | $C_7H_{15}$ | S | m | — |
| 510 | H | $C_{10}H_{21}$ | $C_{10}H_{21}$ | H | S | a | — |
| 511 | H | $C_{10}H_{21}$ | $C_{10}H_{21}$ | H | S | b | — |
| 512 | H | $C_{10}H_{21}$ | $C_{10}H_{21}$ | H | S | c | — |
| 513 | H | $C_{10}H_{21}$ | $C_{10}H_{21}$ | H | S | d | — |
| 514 | H | $C_{10}H_{21}$ | $C_{10}H_{21}$ | H | S | e | — |
| 515 | H | $C_{10}H_{21}$ | $C_{10}H_{21}$ | H | S | f | — |
| 516 | H | $C_{10}H_{21}$ | $C_{10}H_{21}$ | H | S | g | — |
| 517 | H | $C_{10}H_{21}$ | $C_{10}H_{21}$ | H | S | h | — |
| 518 | H | $C_{10}H_{21}$ | $C_{10}H_{21}$ | H | S | i | — |
| 519 | H | $C_{10}H_{21}$ | $C_{10}H_{21}$ | H | S | j | — |
| 520 | H | $C_{10}H_{21}$ | $C_{10}H_{21}$ | H | S | k | — |
| 521 | H | $C_{10}H_{21}$ | $C_{10}H_{21}$ | H | S | l | — |
| 522 | H | $C_{10}H_{21}$ | $C_{10}H_{21}$ | H | S | m | — |
| 523 | H | $C_{10}H_{21}$ | H | $C_{10}H_{21}$ | S | a | — |
| 524 | H | $C_{10}H_{21}$ | H | $C_{10}H_{21}$ | S | b | — |
| 525 | H | $C_{10}H_{21}$ | H | $C_{10}H_{21}$ | S | c | — |
| 526 | H | $C_{10}H_{21}$ | H | $C_{10}H_{21}$ | S | d | — |
| 527 | H | $C_{10}H_{21}$ | H | $C_{10}H_{21}$ | S | e | — |
| 528 | H | $C_{10}H_{21}$ | H | $C_{10}H_{21}$ | S | f | — |
| 529 | H | $C_{10}H_{21}$ | H | $C_{10}H_{21}$ | S | g | — |
| 530 | H | $C_{10}H_{21}$ | H | $C_{10}H_{21}$ | S | h | — |
| 531 | H | $C_{10}H_{21}$ | H | $C_{10}H_{21}$ | S | i | — |
| 532 | H | $C_{10}H_{21}$ | H | $C_{10}H_{21}$ | S | j | — |
| 533 | H | $C_{10}H_{21}$ | H | $C_{10}H_{21}$ | S | k | — |
| 534 | H | $C_{10}H_{21}$ | H | $C_{10}H_{21}$ | S | l | — |
| 535 | H | $C_{10}H_{21}$ | H | $C_{10}H_{21}$ | S | m | — |
| 536 | H | $C_7H_{15}$ | H | $C_7H_{15}$ | O | a | — |
| 537 | H | $C_7H_{15}$ | H | $C_7H_{15}$ | O | b | — |
| 538 | H | $C_7H_{15}$ | H | $C_7H_{15}$ | O | c | — |
| 539 | H | $C_7H_{15}$ | H | $C_7H_{15}$ | O | d | — |
| 540 | H | $C_7H_{15}$ | H | $C_7H_{15}$ | O | e | — |
| 541 | H | $C_7H_{15}$ | H | $C_7H_{15}$ | O | f | — |
| 542 | H | $C_7H_{15}$ | H | $C_7H_{15}$ | O | g | — |
| 543 | H | $C_7H_{15}$ | H | $C_7H_{15}$ | O | h | — |
| 544 | H | $C_7H_{15}$ | H | $C_7H_{15}$ | O | i | — |
| 545 | H | $C_7H_{15}$ | H | $C_7H_{15}$ | O | j | — |
| 546 | H | $C_7H_{15}$ | H | $C_7H_{15}$ | O | k | — |
| 547 | H | $C_7H_{15}$ | H | $C_7H_{15}$ | O | l | — |
| 548 | H | $C_7H_{15}$ | H | $C_7H_{15}$ | O | m | — |
| 549 | H | H | $C_7H_{15}$ | $C_7H_{15}$ | O | a | — |
| 550 | H | H | $C_7H_{15}$ | $C_7H_{15}$ | O | b | — |
| 551 | H | H | $C_7H_{15}$ | $C_7H_{15}$ | O | c | — |
| 552 | H | H | $C_7H_{15}$ | $C_7H_{15}$ | O | d | — |
| 553 | H | H | $C_7H_{15}$ | $C_7H_{15}$ | O | e | — |
| 554 | H | H | $C_7H_{15}$ | $C_7H_{15}$ | O | f | — |
| 555 | H | H | $C_7H_{15}$ | $C_7H_{15}$ | O | g | — |
| 556 | H | H | $C_7H_{15}$ | $C_7H_{15}$ | O | h | — |
| 557 | H | H | $C_7H_{15}$ | $C_7H_{15}$ | O | i | — |
| 558 | H | H | $C_7H_{15}$ | $C_7H_{15}$ | O | j | — |
| 559 | H | H | $C_7H_{15}$ | $C_7H_{15}$ | O | k | — |
| 560 | H | H | $C_7H_{15}$ | $C_7H_{15}$ | O | l | — |
| 561 | H | H | $C_7H_{15}$ | $C_7H_{15}$ | O | m | — |
| 562 | H | $C_{10}H_{21}$ | H | $C_{10}H_{21}$ | O | a | — |
| 563 | H | $C_{10}H_{21}$ | H | $C_{10}H_{21}$ | O | b | — |
| 564 | H | $C_{10}H_{21}$ | H | $C_{10}H_{21}$ | O | c | — |
| 565 | H | $C_{10}H_{21}$ | H | $C_{10}H_{21}$ | O | d | — |
| 566 | H | $C_{10}H_{21}$ | H | $C_{10}H_{21}$ | O | e | — |
| 567 | H | $C_{10}H_{21}$ | H | $C_{10}H_{21}$ | O | f | — |
| 568 | H | $C_{10}H_{21}$ | H | $C_{10}H_{21}$ | O | g | — |
| 569 | H | $C_{10}H_{21}$ | H | $C_{10}H_{21}$ | O | h | — |
| 570 | H | $C_{10}H_{21}$ | H | $C_{10}H_{21}$ | O | i | — |
| 571 | H | $C_{10}H_{21}$ | H | $C_{10}H_{21}$ | O | j | — |
| 572 | H | $C_{10}H_{21}$ | H | $C_{10}H_{21}$ | O | k | — |
| 573 | H | $C_{10}H_{21}$ | H | $C_{10}H_{21}$ | O | l | — |
| 574 | H | $C_{10}H_{21}$ | H | $C_{10}H_{21}$ | O | m | — |
| 575 | H | $CH_3O$ | $C_4H_9O$ | $C_4H_9O$ | O | a | — |
| 576 | H | $CH_3O$ | $C_4H_9O$ | $C_4H_9O$ | O | b | — |
| 577 | H | $CH_3O$ | $C_4H_9O$ | $C_4H_9O$ | O | c | n |
| 578 | H | $CH_3O$ | $C_4H_9O$ | $C_4H_9O$ | O | m | — |
| 579 | H | $CH_3O$ | $C_4H_9O$ | $C_4H_9O$ | S | a | — |
| 580 | H | $CH_3O$ | $C_4H_9O$ | $C_4H_9O$ | S | b | — |
| 581 | H | $CH_3O$ | $C_4H_9O$ | $C_4H_9O$ | S | c | — |
| 582 | H | $CH_3O$ | $C_4H_9O$ | $C_4H_9O$ | S | m | — |
| 583 | H | $C_4H_9O$ | $C_4H_9O$ | $C_4H_9O$ | O | a | — |
| 584 | H | $C_4H_9O$ | $C_4H_9O$ | $C_4H_9O$ | O | b | — |
| 585 | H | $C_4H_9O$ | $C_4H_9O$ | $C_4H_9O$ | O | c | — |
| 586 | H | $C_4H_9O$ | $C_4H_9O$ | $C_4H_9O$ | O | m | — |
| 587 | H | $C_4H_9O$ | $C_4H_9O$ | $C_4H_9O$ | S | a | — |
| 588 | H | $C_4H_9O$ | $C_4H_9O$ | $C_4H_9O$ | S | b | — |
| 589 | H | $C_4H_9O$ | $C_4H_9O$ | $C_4H_9O$ | S | c | — |
| 590 | H | $C_4H_9O$ | $C_4H_9O$ | $C_4H_9O$ | S | m | — |
| 591 | H | $CH_3O$ | $C_8H_{17}O$ | $C_8H_{17}O$ | O | a | — |
| 592 | H | $CH_3O$ | $C_8H_{17}O$ | $C_8H_{17}O$ | O | b | — |
| 593 | H | $CH_3O$ | $C_8H_{17}O$ | $C_8H_{17}O$ | O | c | — |
| 594 | H | $CH_3O$ | $C_8H_{17}O$ | $C_8H_{17}O$ | O | m | — |
| 595 | H | $CH_3O$ | $C_8H_{17}O$ | $C_8H_{17}O$ | S | a | — |
| 596 | H | $CH_3O$ | $C_8H_{17}O$ | $C_8H_{17}O$ | S | b | — |
| 597 | H | $CH_3O$ | $C_8H_{17}O$ | $C_8H_{17}O$ | S | c | — |
| 598 | H | $CH_3O$ | $C_8H_{17}O$ | $C_8H_{17}O$ | S | m | — |

TABLE 4-continued

[Structure diagram with R14, R15, R16 substituents on ring containing X, with carbonyl linked to N(R1)-G]

| Ex. No. | R¹ | R¹⁴ | R¹⁵ | R¹⁶ | X | G | m.p. |
|---|---|---|---|---|---|---|---|

Key:

*a*: 2,6-di(i-Pr)phenyl

*b*: 2,3-dimethylphenyl

*c*: 2,3-dichlorophenyl

*d*: 2,4-difluorophenyl

*e*: 3-MeS-6-Me-pyridin-2-yl

*f*: 3-MeS-pyrimidin-2-yl (MeS, N, N ring)

*g*: 3-MeS-pyridin-2-yl

*h*: 6-SMe-pyridin-3-yl

TABLE 4-continued

[Structure diagram with R14, R15, R16 substituents on ring containing X, with carbonyl linked to N(R1)-G]

| Ex. No. | R¹ | R¹⁴ | R¹⁵ | R¹⁶ | X | G | m.p. |
|---|---|---|---|---|---|---|---|

*i*: 2-MeS-6-SMe-pyridin-3-yl

*j*: 4-Br-1-Me-pyrazol-5-yl

*k*: 1,3,5-trimethyl-4-Me-pyrazolyl (Me, Me, Me substituents)

*l*: 1-Me-pyrazol-5-yl

*m*: 5-MeS-1,3-dimethyl-pyrazol-4-yl (MeS, Me, Me)

ⁿFor (2S, 3R, 4R, 5R) isomer: ¹H NMR(300MHz, CDCl₃): δ7.70(1H, s); 6.63(1H, s); 4.99(1H, d, J=4.39Hz); 4.41(1H, d, J=5.86Hz); 4.34(1H, t, J=6.41Hz); 3.94–3.81(2H, m); 3.63–3.50(3H, m); 3.59(3H, s); 2.49(3H, s); 2.47(3H, s); 2.38(3H, s); 1.66–1.50(4H, m); 0.91(3H, t, J=7.32Hz); 0.88(3H, t, J=7.32Hz).
For (2S, 3R, 4R, 5S) isomer: ¹H NMR(300MHz, CDCl₃): δ7.72(1H, s); 6.65(1H, s); 5.17(1H, d, J=4.03Hz); 4.83(1H, d, J=5.86Hz); 4.24(1H, dd, J=5.86, 4.03Hz); 3.95(1H, t, J=3.85Hz); 3.75–3.47(4H, m); 3.52(3H, s); 2.49(3H, s); 2.47(3H, s); 2.39(3H, s); 1.66–1.43(4H, m); 1.42–1.26(4H, m); 0.92(3H, t, J=7.32Hz); 0.86(3H, t, J=7.32Hz).

TABLE 5

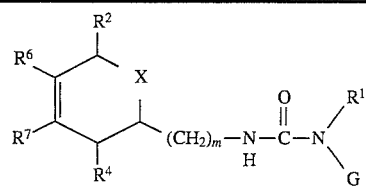

| Ex. No. | R¹ | R² | R⁴ | R⁶ | R⁷ | X | m | G | m.p. |
|---|---|---|---|---|---|---|---|---|---|
| 599 | H | H | H | C₅H₁₁ | C₅H₁₁ | S | 0 | a | 157–159 |
| 600 | H | H | H | C₅H₁₁ | C₅H₁₁ | S | 0 | b | — |
| 601 | H | H | H | C₅H₁₁ | C₅H₁₁ | S | 0 | c | — |
| 602 | H | H | H | C₅H₁₁ | C₅H₁₁ | S | 0 | d | 117–119 |
| 603 | H | H | H | C₅H₁₁ | C₅H₁₁ | S | 0 | e | — |
| 604 | H | H | H | C₅H₁₁ | C₅H₁₁ | S | 0 | f | — |
| 605 | H | C₅H₁₁ | C₅H₁₁ | H | H | S | 0 | a | — |
| 606 | H | C₅H₁₁ | C₅H₁₁ | H | H | S | 0 | b | — |
| 607 | H | C₅H₁₁ | C₅H₁₁ | H | H | S | 0 | c | — |
| 608 | H | C₅H₁₁ | C₅H₁₁ | H | H | S | 0 | d | — |
| 609 | H | C₅H₁₁ | C₅H₁₁ | H | H | S | 0 | e | — |
| 610 | H | C₅H₁₁ | C₅H₁₁ | H | H | S | 0 | f | — |
| 611 | H | H | H | CH₃ | CH₃ | S | 0 | a | — |
| 612 | H | H | H | CH₃ | CH₃ | S | 0 | b | — |
| 613 | H | H | H | CH₃ | CH₃ | S | 0 | c | — |
| 614 | H | H | H | CH₃ | CH₃ | S | 0 | d | — |
| 615 | H | H | H | CH₃ | CH₃ | S | 0 | e | — |
| 616 | H | H | H | CH₃ | CH₃ | S | 0 | f | — |
| 617 | H | CH₃ | CH₃ | H | H | S | 0 | a | — |
| 618 | H | CH₃ | CH₃ | H | H | S | 0 | b | — |
| 619 | H | CH₃ | CH₃ | H | H | S | 0 | c | — |
| 620 | H | CH₃ | CH₃ | H | H | S | 0 | d | — |
| 621 | H | CH₃ | CH₃ | H | H | S | 0 | e | — |
| 622 | H | CH₃ | CH₃ | H | H | S | 0 | f | — |
| 623 | H | H | H | C₅H₁₁ | C₅H₁₁ | O | 0 | a | — |
| 624 | H | H | H | C₅H₁₁ | C₅H₁₁ | O | 0 | b | — |
| 625 | H | H | H | C₅H₁₁ | C₅H₁₁ | O | 0 | c | — |
| 626 | H | H | H | C₅H₁₁ | C₅H₁₁ | O | 0 | d | — |
| 627 | H | H | H | C₅H₁₁ | C₅H₁₁ | O | 0 | e | — |
| 628 | H | H | H | C₅H₁₁ | C₅H₁₁ | O | 0 | f | — |
| 629 | H | C₅H₁₁ | C₅H₁₁ | H | H | O | 0 | a | — |
| 630 | H | C₅H₁₁ | C₅H₁₁ | H | H | O | 0 | b | — |
| 631 | H | C₅H₁₁ | C₅H₁₁ | H | H | O | 0 | c | — |
| 632 | H | C₅H₁₁ | C₅H₁₁ | H | H | O | 0 | d | — |
| 633 | H | C₅H₁₁ | C₅H₁₁ | H | H | O | 0 | e | — |
| 634 | H | C₅H₁₁ | C₅H₁₁ | H | H | O | 0 | f | — |
| 635 | H | H | H | CH₃ | CH₃ | O | 0 | a | — |
| 636 | H | H | H | CH₃ | CH₃ | O | 0 | b | — |
| 637 | H | H | H | CH₃ | CH₃ | O | 0 | c | — |
| 638 | H | H | H | CH₃ | CH₃ | O | 0 | d | — |
| 639 | H | H | H | CH₃ | CH₃ | O | 0 | e | — |
| 640 | H | H | H | CH₃ | CH₃ | O | 0 | f | — |
| 641 | H | CH₃ | CH₃ | H | H | O | 0 | a | — |
| 642 | H | CH₃ | CH₃ | H | H | O | 0 | b | — |
| 643 | H | CH₃ | CH₃ | H | H | O | 0 | c | — |
| 644 | H | CH₃ | CH₃ | H | H | O | 0 | d | — |
| 645 | H | CH₃ | CH₃ | H | H | O | 0 | e | — |
| 646 | H | CH₃ | CH₃ | H | H | O | 0 | f | — |
| 647 | H | H | H | C₅H₁₁ | C₅H₁₁ | S | 1 | a | 65–67 |
| 648 | H | H | H | C₅H₁₁ | C₅H₁₁ | S | 1 | b | — |
| 649 | H | H | H | C₅H₁₁ | C₅H₁₁ | S | 1 | c | — |
| 650 | H | H | H | C₅H₁₁ | C₅H₁₁ | S | 1 | d | 79–81 |
| 651 | H | H | H | C₅H₁₁ | C₅H₁₁ | S | 1 | e | — |
| 652 | H | H | H | C₅H₁₁ | C₅H₁₁ | S | 1 | f | — |
| 653 | H | C₅H₁₁ | C₅H₁₁ | H | H | S | 1 | a | — |
| 654 | H | C₅H₁₁ | C₅H₁₁ | H | H | S | 1 | b | — |
| 655 | H | C₅H₁₁ | C₅H₁₁ | H | H | S | 1 | c | — |
| 656 | H | C₅H₁₁ | C₅H₁₁ | H | H | S | 1 | d | — |
| 657 | H | C₅H₁₁ | C₅H₁₁ | H | H | S | 1 | e | — |
| 658 | H | C₅H₁₁ | C₅H₁₁ | H | H | S | 1 | f | — |
| 659 | H | H | H | CH₃ | CH₃ | S | 1 | a | — |
| 660 | H | H | H | CH₃ | CH₃ | S | 1 | b | — |
| 661 | H | H | H | CH₃ | CH₃ | S | 1 | c | — |
| 662 | H | H | H | CH₃ | CH₃ | S | 1 | d | — |
| 663 | H | H | H | CH₃ | CH₃ | S | 1 | e | — |
| 664 | H | H | H | CH₃ | CH₃ | S | 1 | f | — |

TABLE 5-continued

![structure with R2, R6, R7, R4, X, (CH2)m-NH-C(=O)-N(R1)(G)]

| Ex. No. | R¹ | R² | R⁴ | R⁶ | R⁷ | X | m | G | m.p. |
|---|---|---|---|---|---|---|---|---|---|
| 665 | H | CH₃ | CH₃ | H | H | S | 1 | a | — |
| 666 | H | CH₃ | CH₃ | H | H | S | 1 | b | — |
| 667 | H | CH₃ | CH₃ | H | H | S | 1 | c | — |
| 668 | H | CH₃ | CH₃ | H | H | S | 1 | d | — |
| 669 | H | CH₃ | CH₃ | H | H | S | 1 | e | — |
| 670 | H | CH₃ | CH₃ | H | H | S | 1 | f | — |
| 671 | H | H | H | C₅H₁₁ | C₅H₁₁ | O | 1 | a | — |
| 672 | H | H | H | C₅H₁₁ | C₅H₁₁ | O | 1 | b | — |
| 673 | H | H | H | C₅H₁₁ | C₅H₁₁ | O | 1 | c | — |
| 674 | H | H | H | C₅H₁₁ | C₅H₁₁ | O | 1 | d | — |
| 675 | H | H | H | C₅H₁₁ | C₅H₁₁ | O | 1 | e | — |
| 676 | H | H | H | C₅H₁₁ | C₅H₁₁ | O | 1 | f | — |
| 677 | H | C₅H₁₁ | C₅H₁₁ | H | H | O | 1 | a | — |
| 678 | H | C₅H₁₁ | C₅H₁₁ | H | H | O | 1 | b | — |
| 679 | H | C₅H₁₁ | C₅H₁₁ | H | H | O | 1 | c | — |
| 680 | H | C₅H₁₁ | C₅H₁₁ | H | H | O | 1 | d | — |
| 681 | H | C₅H₁₁ | C₅H₁₁ | H | H | O | 1 | e | — |
| 682 | H | C₅H₁₁ | C₅H₁₁ | H | H | O | 1 | f | — |
| 683 | H | H | H | CH₃ | CH₃ | O | 1 | a | — |
| 684 | H | H | H | CH₃ | CH₃ | O | 1 | b | — |
| 685 | H | H | H | CH₃ | CH₃ | O | 1 | c | — |
| 686 | H | H | H | CH₃ | CH₃ | O | 1 | d | — |
| 687 | H | H | H | CH₃ | CH₃ | O | 1 | e | — |
| 688 | H | H | H | CH₃ | CH₃ | O | 1 | f | — |
| 689 | H | CH₃ | CH₃ | H | H | O | 1 | a | — |
| 690 | H | CH₃ | CH₃ | H | H | O | 1 | b | — |
| 691 | H | CH₃ | CH₃ | H | H | O | 1 | c | — |
| 692 | H | CH₃ | CH₃ | H | H | O | 1 | d | — |
| 693 | H | CH₃ | CH₃ | H | H | O | 1 | e | — |
| 694 | H | CH₃ | CH₃ | H | H | O | 1 | f | — |
| 695 | H | H | H | C₅H₁₁ | C₅H₁₁ | S | 2 | a | — |
| 696 | H | H | H | C₅H₁₁ | C₅H₁₁ | S | 3 | a | — |
| 697 | H | H | H | C₅H₁₁ | C₅H₁₁ | S | 4 | a | — |
| 698 | H | H | H | C₅H₁₁ | C₅H₁₁ | S | 5 | a | — |
| 699 | CH₃ | H | H | C₅H₁₁ | C₅H₁₁ | S | 0 | C₆H₅ | — |
| 700 | H | H | H | C₅H₁₁ | C₅H₁₁ | SO | 1 | C₆H₅ | — |
| 701 | H | H | H | C₅H₁₁ | C₅H₁₁ | SO₂ | 1 | C₆H₅ | — |
| 702 | CH₂C₆H₅ | H | H | C₅H₁₁ | C₅H₁₁ | S | 0 | C₆H₅ | — |
| 703 | H | H | C₅H₁₁ | C₅H₁₁ | H | S | 0 | a | — |

Key:

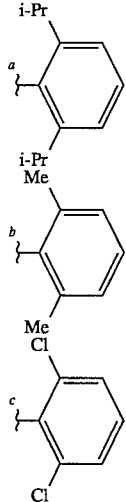

a: 2,6-di(i-Pr)phenyl
b: 2-(i-Pr)-6-Me-phenyl
c: 2-Me-6-Cl-phenyl (or 2,6-dichlorophenyl variant shown)

TABLE 5-continued

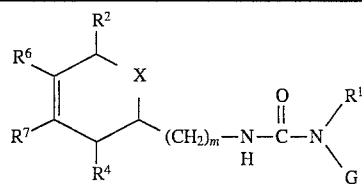

| Ex. No. | $R^1$ | $R^2$ | $R^4$ | $R^6$ | $R^7$ | X | m | G | m.p. |
|---|---|---|---|---|---|---|---|---|---|

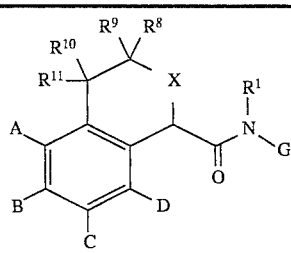

TABLE 6

| Ex. No. | $R^1$ | $R^8$ | $R^9$ | $R^{10}$ | $R^{11}$ | A | B | C | D | X | G | m.p. |
|---|---|---|---|---|---|---|---|---|---|---|---|---|
| 606 | H | H | H | H | H | H | CH$_3$O | CH$_3$O | H | S | a | 207–208 |
| 607 | H | H | H | H | H | H | CH$_3$O | CH$_3$O | H | S | b | — |
| 608 | H | H | H | H | H | H | CH$_3$O | CH$_3$O | H | S | c | — |
| 609 | H | H | H | H | H | H | CH$_3$O | CH$_3$O | H | S | d | — |
| 610 | H | H | H | H | H | H | CH$_3$O | CH$_3$O | H | S | e | 218–219 |
| 611 | H | H | H | H | H | H | CH$_3$O | CH$_3$O | H | S | f | — |
| 612 | H | H | H | H | H | H | CH$_3$O | CH$_3$O | H | S | g | 186–187 |
| 613 | H | H | H | H | H | H | CH$_3$O | CH$_3$O | H | O | a | 72–74 |
| 614 | H | H | H | H | H | H | CH$_3$O | CH$_3$O | H | O | b | — |
| 615 | H | H | H | H | H | H | CH$_3$O | CH$_3$O | H | O | c | — |
| 616 | H | H | H | H | H | H | CH$_3$O | CH$_3$O | H | O | d | — |
| 617 | H | H | H | H | H | H | CH$_3$O | CH$_3$O | H | O | e | 78–80 |
| 618 | H | H | H | H | H | H | CH$_3$O | CH$_3$O | H | O | f | — |
| 619 | H | H | H | H | H | H | CH$_3$O | CH$_3$O | H | O | g | — |
| 620 | H | H | H | C$_5$H$_{11}$ | H | H | CH$_3$O | CH$_3$O | H | S | a | — |
| 621 | H | H | H | C$_5$H$_{11}$ | H | H | CH$_3$O | CH$_3$O | H | S | b | — |
| 622 | H | H | H | C$_5$H$_{11}$ | H | H | CH$_3$O | CH$_3$O | H | S | c | — |
| 623 | H | H | H | C$_5$H$_{11}$ | H | H | CH$_3$O | CH$_3$O | H | S | d | — |
| 624 | H | H | H | C$_5$H$_{11}$ | H | H | CH$_3$O | CH$_3$O | H | S | e | 192–193 |
| 625 | H | H | H | C$_5$H$_{11}$ | H | H | CH$_3$O | CH$_3$O | H | S | f | — |
| 626 | H | H | H | C$_5$H$_{11}$ | H | H | CH$_3$O | CH$_3$O | H | S | g | — |
| 627 | H | H | H | C$_5$H$_{11}$ | H | H | CH$_3$O | CH$_3$O | H | O | a | — |
| 628 | H | H | H | C$_5$H$_{11}$ | H | H | CH$_3$O | CH$_3$O | H | O | b | — |
| 629 | H | H | H | C$_5$H$_{11}$ | H | H | CH$_3$O | CH$_3$O | H | O | c | — |
| 630 | H | H | H | C$_5$H$_{11}$ | H | H | CH$_3$O | CH$_3$O | H | O | d | — |
| 631 | H | H | H | C$_5$H$_{11}$ | H | H | CH$_3$O | CH$_3$O | H | O | e | — |
| 632 | H | H | H | C$_5$H$_{11}$ | H | H | CH$_3$O | CH$_3$O | H | O | f | — |

TABLE 6-continued

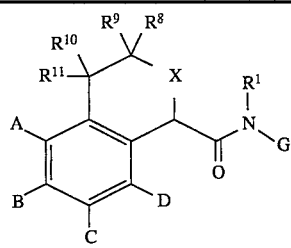

| Ex. No. | R¹ | R⁸ | R⁹ | R¹⁰ | R¹¹ | A | B | C | D | X | G | m.p. |
|---|---|---|---|---|---|---|---|---|---|---|---|---|
| 633 | H | H | H | $C_5H_{11}$ | H | H | $CH_3O$ | $CH_3O$ | H | O | g | — |
| 634 | H | $C_5H_{11}$ | H | H | H | H | $CH_3O$ | $CH_3O$ | H | S | a | — |
| 635 | H | $C_5H_{11}$ | H | H | H | H | $CH_3O$ | $CH_3O$ | H | S | b | — |
| 636 | H | $C_5H_{11}$ | H | H | H | H | $CH_3O$ | $CH_3O$ | H | S | c | — |
| 637 | H | $C_5H_{11}$ | H | H | H | H | $CH_3O$ | $CH_3O$ | H | S | d | — |
| 638 | H | $C_5H_{11}$ | H | H | H | H | $CH_3O$ | $CH_3O$ | H | S | e | — |
| 639 | H | $C_5H_{11}$ | H | H | H | H | $CH_3O$ | $CH_3O$ | H | S | f | — |
| 640 | H | $C_5H_{11}$ | H | H | H | H | $CH_3O$ | $CH_3O$ | H | S | g | — |
| 641 | H | $C_5H_{11}$ | H | H | H | H | $CH_3O$ | $CH_3O$ | H | O | a | — |
| 642 | H | $C_5H_{11}$ | H | H | H | H | $CH_3O$ | $CH_3O$ | H | O | b | — |
| 643 | H | $C_5H_{11}$ | H | H | H | H | $CH_3O$ | $CH_3O$ | H | O | c | — |
| 644 | H | $C_5H_{11}$ | H | H | H | H | $CH_3O$ | $CH_3O$ | H | O | d | — |
| 645 | H | $C_5H_{11}$ | H | H | H | H | $CH_3O$ | $CH_3O$ | H | O | e | — |
| 646 | H | $C_5H_{11}$ | H | H | H | H | $CH_3O$ | $CH_3O$ | H | O | f | — |
| 647 | H | $C_5H_{11}$ | H | H | H | H | $CH_3O$ | $CH_3O$ | H | O | g | — |
| 648 | H | H | H | $C_5H_{11}$ | $C_5H_{11}$ | H | $CH_3O$ | $CH_3O$ | H | S | a | — |
| 649 | H | H | H | $C_5H_{11}$ | $C_5H_{11}$ | H | $CH_3O$ | $CH_3O$ | H | S | b | — |
| 650 | H | H | H | $C_5H_{11}$ | $C_5H_{11}$ | H | $CH_3O$ | $CH_3O$ | H | S | c | — |
| 651 | H | H | H | $C_5H_{11}$ | $C_5H_{11}$ | H | $CH_3O$ | $CH_3O$ | H | S | d | — |
| 652 | H | H | H | $C_5H_{11}$ | $C_5H_{11}$ | H | $CH_3O$ | $CH_3O$ | H | S | e | — |
| 653 | H | H | H | $C_5H_{11}$ | $C_5H_{11}$ | H | $CH_3O$ | $CH_3O$ | H | S | f | — |
| 654 | H | H | H | $C_5H_{11}$ | $C_5H_{11}$ | H | $CH_3O$ | $CH_3O$ | H | S | g | — |
| 655 | H | H | H | $C_5H_{11}$ | $C_5H_{11}$ | H | $CH_3O$ | $CH_3O$ | H | O | a | — |
| 656 | H | H | H | $C_5H_{11}$ | $C_5H_{11}$ | H | $CH_3O$ | $CH_3O$ | H | O | b | — |
| 657 | H | H | H | $C_5H_{11}$ | $C_5H_{11}$ | H | $CH_3O$ | $CH_3O$ | H | O | c | — |
| 658 | H | H | H | $C_5H_{11}$ | $C_5H_{11}$ | H | $CH_3O$ | $CH_3O$ | H | O | d | — |
| 659 | H | H | H | $C_5H_{11}$ | $C_5H_{11}$ | H | $CH_3O$ | $CH_3O$ | H | O | e | — |
| 660 | H | H | H | $C_5H_{11}$ | $C_5H_{11}$ | H | $CH_3O$ | $CH_3O$ | H | O | f | — |
| 661 | H | H | H | $C_5H_{11}$ | $C_5H_{11}$ | H | $CH_3O$ | $CH_3O$ | H | O | g | — |
| 662 | H | H | H | H | H | H | $CH_3O$ | $C_5H_{11}O$ | H | S | a | 172–173 |
| 663 | H | H | H | H | H | H | $CH_3O$ | $C_5H_{11}O$ | H | S | b | — |
| 664 | H | H | H | H | H | H | $CH_3O$ | $C_5H_{11}O$ | H | S | c | — |
| 665 | H | H | H | H | H | H | $CH_3O$ | $C_5H_{11}O$ | H | S | d | — |
| 666 | H | H | H | H | H | H | $CH_3O$ | $C_5H_{11}O$ | H | S | e | 181–182 |
| 667 | H | H | H | H | H | H | $CH_3O$ | $C_5H_{11}O$ | H | S | f | — |
| 668 | H | H | H | H | H | H | $CH_3O$ | $C_5H_{11}O$ | H | S | g | — |
| 669 | H | H | H | H | H | H | $CH_3O$ | $C_5H_{11}O$ | H | O | a | — |
| 670 | H | H | H | H | H | H | $CH_3O$ | $C_5H_{11}O$ | H | O | b | — |
| 671 | H | H | H | H | H | H | $CH_3O$ | $C_5H_{11}O$ | H | O | c | — |
| 672 | H | H | H | H | H | H | $CH_3O$ | $C_5H_{11}O$ | H | O | d | — |
| 673 | H | H | H | H | H | H | $CH_3O$ | $C_5H_{11}O$ | H | O | e | — |
| 674 | H | H | H | H | H | H | $CH_3O$ | $C_5H_{11}O$ | H | O | f | — |
| 675 | H | H | H | H | H | H | $CH_3O$ | $C_5H_{11}O$ | H | O | g | — |
| 676 | H | H | H | $C_5H_{11}$ | H | H | $CH_3O$ | $C_5H_{11}O$ | H | S | a | — |
| 677 | H | H | H | $C_5H_{11}$ | H | H | $CH_3O$ | $C_5H_{11}O$ | H | S | b | — |
| 678 | H | H | H | $C_5H_{11}$ | H | H | $CH_3O$ | $C_5H_{11}O$ | H | S | c | — |
| 679 | H | H | H | $C_5H_{11}$ | H | H | $CH_3O$ | $C_5H_{11}O$ | H | S | d | — |
| 680 | H | H | H | $C_5H_{11}$ | H | H | $CH_3O$ | $C_5H_{11}O$ | H | S | e | — |
| 681 | H | H | H | $C_5H_{11}$ | H | H | $CH_3O$ | $C_5H_{11}O$ | H | S | f | — |
| 682 | H | H | H | $C_5H_{11}$ | H | H | $CH_3O$ | $C_5H_{11}O$ | H | S | g | — |
| 683 | H | H | H | $C_5H_{11}$ | H | H | $CH_3O$ | $C_5H_{11}O$ | H | O | a | — |
| 684 | H | H | H | $C_5H_{11}$ | H | H | $CH_3O$ | $C_5H_{11}O$ | H | O | b | — |
| 685 | H | H | H | $C_5H_{11}$ | H | H | $CH_3O$ | $C_5H_{11}O$ | H | O | c | — |
| 686 | H | H | H | $C_5H_{11}$ | H | H | $CH_3O$ | $C_5H_{11}O$ | H | O | d | — |
| 687 | H | H | H | $C_5H_{11}$ | H | H | $CH_3O$ | $C_5H_{11}O$ | H | O | e | — |
| 688 | H | H | H | $C_5H_{11}$ | H | H | $CH_3O$ | $C_5H_{11}O$ | H | O | f | — |
| 689 | H | H | H | $C_5H_{11}$ | H | H | $CH_3O$ | $C_5H_{11}O$ | H | O | g | — |
| 690 | H | $C_5H_{11}$ | H | H | H | H | $CH_3O$ | $C_5H_{11}O$ | H | S | a | — |
| 691 | H | $C_5H_{11}$ | H | H | H | H | $CH_3O$ | $C_5H_{11}O$ | H | S | b | — |
| 692 | H | $C_5H_{11}$ | H | H | H | H | $CH_3O$ | $C_5H_{11}O$ | H | S | c | — |
| 693 | H | $C_5H_{11}$ | H | H | H | H | $CH_3O$ | $C_5H_{11}O$ | H | S | d | — |
| 694 | H | $C_5H_{11}$ | H | H | H | H | $CH_3O$ | $C_5H_{11}O$ | H | S | e | — |
| 695 | H | $C_5H_{11}$ | H | H | H | H | $CH_3O$ | $C_5H_{11}O$ | H | S | f | — |

TABLE 6-continued

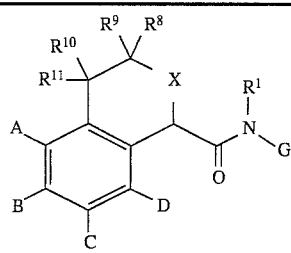

| Ex. No. | R¹ | R⁸ | R⁹ | R¹⁰ | R¹¹ | A | B | C | D | X | G | m.p. |
|---|---|---|---|---|---|---|---|---|---|---|---|---|
| 696 | H | C₅H₁₁ | H | H | H | H | CH₃O | C₅H₁₁O | H | S | g | — |
| 697 | H | C₅H₁₁ | H | H | H | H | CH₃O | C₅H₁₁O | H | O | a | — |
| 698 | H | C₅H₁₁ | H | H | H | H | CH₃O | C₅H₁₁O | H | O | b | — |
| 699 | H | C₅H₁₁ | H | H | H | H | CH₃O | C₅H₁₁O | H | O | c | — |
| 700 | H | C₅H₁₁ | H | H | H | H | CH₃O | C₅H₁₁O | H | O | d | — |
| 701 | H | C₅H₁₁ | H | H | H | H | CH₃O | C₅H₁₁O | H | O | e | — |
| 702 | H | C₅H₁₁ | H | H | H | H | CH₃O | C₅H₁₁O | H | O | f | — |
| 703 | H | C₅H₁₁ | H | H | H | H | CH₃O | C₅H₁₁O | H | O | g | — |
| 704 | H | H | H | C₅H₁₁ | C₅H₁₁ | H | CH₃O | C₅H₁₁O | H | S | a | — |
| 705 | H | H | H | C₅H₁₁ | C₅H₁₁ | H | CH₃O | C₅H₁₁O | H | S | b | — |
| 706 | H | H | H | C₅H₁₁ | C₅H₁₁ | H | CH₃O | C₅H₁₁O | H | S | c | — |
| 707 | H | H | H | C₅H₁₁ | C₅H₁₁ | H | CH₃O | C₅H₁₁O | H | S | d | — |
| 708 | H | H | H | C₅H₁₁ | C₅H₁₁ | H | CH₃O | C₅H₁₁O | H | S | e | — |
| 709 | H | H | H | C₅H₁₁ | C₅H₁₁ | H | CH₃O | C₅H₁₁O | H | S | f | — |
| 710 | H | H | H | C₅H₁₁ | C₅H₁₁ | H | CH₃O | C₅H₁₁O | H | S | g | — |
| 711 | H | H | H | C₅H₁₁ | C₅H₁₁ | H | CH₃O | C₅H₁₁O | H | O | a | — |
| 712 | H | H | H | C₅H₁₁ | C₅H₁₁ | H | CH₃O | C₅H₁₁O | H | O | b | — |
| 713 | H | H | H | C₅H₁₁ | C₅H₁₁ | H | CH₃O | C₅H₁₁O | H | O | c | — |
| 714 | H | H | H | C₅H₁₁ | C₅H₁₁ | H | CH₃O | C₅H₁₁O | H | O | d | — |
| 715 | H | H | H | C₅H₁₁ | C₅H₁₁ | H | CH₃O | C₅H₁₁O | H | O | e | — |
| 716 | H | H | H | C₅H₁₁ | C₅H₁₁ | H | CH₃O | C₅H₁₁O | H | O | f | — |
| 717 | H | H | H | C₅H₁₁ | C₅H₁₁ | H | CH₃O | C₅H₁₁O | H | O | g | — |
| 718 | H | H | H | C₅H₁₁ | H | CH₃O | H | CH₃O | H | S | a | — |
| 719 | H | H | H | C₅H₁₁ | H | CH₃O | H | CH₃O | H | S | b | — |
| 720 | H | H | H | C₅H₁₁ | H | CH₃O | H | CH₃O | H | S | c | — |
| 721 | H | H | H | C₅H₁₁ | H | CH₃O | H | CH₃O | H | S | d | — |
| 722 | H | H | H | C₅H₁₁ | H | CH₃O | H | CH₃O | H | S | e | — |
| 723 | H | H | H | C₅H₁₁ | H | CH₃O | H | CH₃O | H | S | f | — |
| 724 | H | H | H | C₅H₁₁ | H | CH₃O | H | CH₃O | H | S | g | — |
| 725 | H | H | H | C₅H₁₁ | H | CH₃O | H | CH₃O | H | O | a | — |
| 726 | H | H | H | C₅H₁₁ | H | CH₃O | H | CH₃O | H | O | b | — |
| 727 | H | H | H | C₅H₁₁ | H | CH₃O | H | CH₃O | H | O | c | — |
| 728 | H | H | H | C₅H₁₁ | H | CH₃O | H | CH₃O | H | O | d | — |
| 729 | H | H | H | C₅H₁₁ | H | CH₃O | H | CH₃O | H | O | e | — |
| 730 | H | H | H | C₅H₁₁ | H | CH₃O | H | CH₃O | H | O | f | — |
| 731 | H | H | H | C₅H₁₁ | H | CH₃O | H | CH₃O | H | O | g | — |
| 732 | H | C₅H₁₁ | H | H | H | CH₃O | H | CH₃O | H | S | a | — |
| 733 | H | C₅H₁₁ | H | H | H | CH₃O | H | CH₃O | H | S | b | — |
| 734 | H | C₅H₁₁ | H | H | H | CH₃O | H | CH₃O | H | S | c | — |
| 735 | H | C₅H₁₁ | H | H | H | CH₃O | H | CH₃O | H | S | d | — |
| 736 | H | C₅H₁₁ | H | H | H | CH₃O | H | CH₃O | H | S | e | — |
| 737 | H | C₅H₁₁ | H | H | H | CH₃O | H | CH₃O | H | S | f | — |
| 738 | H | C₅H₁₁ | H | H | H | CH₃O | H | CH₃O | H | S | g | — |
| 739 | H | C₅H₁₁ | H | H | H | CH₃O | H | CH₃O | H | O | a | — |
| 740 | H | C₅H₁₁ | H | H | H | CH₃O | H | CH₃O | H | O | b | — |
| 741 | H | C₅H₁₁ | H | H | H | CH₃O | H | CH₃O | H | O | c | — |
| 742 | H | C₅H₁₁ | H | H | H | CH₃O | H | CH₃O | H | O | d | — |
| 743 | H | C₅H₁₁ | H | H | H | CH₃O | H | CH₃O | H | O | e | — |
| 744 | H | C₅H₁₁ | H | H | H | CH₃O | H | CH₃O | H | O | f | — |
| 745 | R | C₅H₁₁ | H | H | H | CH₃O | H | CH₃O | H | O | g | — |
| 746 | H | H | H | C₅H₁₁ | H | CH₃O | H | H | CH₃O | S | a | — |
| 747 | H | H | H | C₅H₁₁ | H | CH₃O | H | H | CH₃O | S | b | — |
| 748 | H | H | H | C₅H₁₁ | H | CH₃O | H | H | CH₃O | S | c | — |
| 749 | H | H | H | C₅H₁₁ | H | CH₃O | H | H | CH₃O | S | d | — |
| 750 | H | H | H | C₅H₁₁ | H | CH₃O | H | H | CH₃O | S | e | — |
| 751 | H | H | H | C₅H₁₁ | H | CH₃O | H | H | CH₃O | S | f | — |
| 752 | H | H | H | C₅H₁₁ | H | CH₃O | H | H | CH₃O | S | g | — |
| 753 | H | H | H | C₅H₁₁ | H | CH₃O | H | H | CH₃O | O | a | — |
| 754 | H | H | H | C₅H₁₁ | H | CH₃O | H | H | CH₃O | O | b | — |
| 755 | H | H | H | C₅H₁₁ | H | CH₃O | H | H | CH₃O | O | c | — |
| 756 | H | H | H | C₅H₁₁ | H | CH₃O | H | H | CH₃O | O | d | — |
| 757 | H | H | H | C₅H₁₁ | H | CH₃O | H | H | CH₃O | O | e | — |
| 758 | H | H | H | C₅H₁₁ | H | CH₃O | H | H | CH₃O | O | f | — |

TABLE 6-continued

| Ex. No. | R¹ | R⁸ | R⁹ | R¹⁰ | R¹¹ | A | B | C | D | X | G | m.p. |
|---|---|---|---|---|---|---|---|---|---|---|---|---|
| 759 | H | H | H | $C_5H_{11}$ | H | $CH_3O$ | H | H | $CH_3O$ | O | g | — |
| 760 | H | $C_5H_{11}$ | H | H | H | $CH_3O$ | H | H | $CH_3O$ | S | a | — |
| 761 | H | $C_5H_{11}$ | H | H | H | $CH_3O$ | H | H | $CH_3O$ | S | b | — |
| 762 | H | $C_5H_{11}$ | H | H | H | $CH_3O$ | H | H | $CH_3O$ | S | c | — |
| 763 | H | $C_5H_{11}$ | H | H | H | $CH_3O$ | H | H | $CH_3O$ | S | d | — |
| 764 | H | $C_5H_{11}$ | H | H | H | $CH_3O$ | H | H | $CH_3O$ | S | e | — |
| 765 | H | $C_5H_{11}$ | H | H | H | $CH_3O$ | H | H | $CH_3O$ | S | f | — |
| 766 | H | $C_5H_{11}$ | H | H | H | $CH_3O$ | H | H | $CH_3O$ | S | g | — |
| 767 | H | $C_5H_{11}$ | H | H | H | $CH_3O$ | H | H | $CH_3O$ | O | a | — |
| 768 | H | $C_5H_{11}$ | H | H | H | $CH_3O$ | H | H | $CH_3O$ | O | b | — |
| 769 | H | $C_5H_{11}$ | H | H | H | $CH_3O$ | H | H | $CH_3O$ | O | c | — |
| 770 | H | $C_5H_{11}$ | H | H | H | $CH_3O$ | H | H | $CH_3O$ | O | d | — |
| 771 | H | $C_5H_{11}$ | H | H | H | $CH_3O$ | H | H | $CH_3O$ | O | e | — |
| 772 | H | $C_5H_{11}$ | H | H | H | $CH_3O$ | H | H | $CH_3O$ | O | f | — |
| 773 | H | $C_5H_{11}$ | H | H | H | $CH_3O$ | H | H | $CH_3O$ | O | g | — |
| 774 | $CH_3$ | H | H | H | H | H | $CH_3O$ | $CH_3O$ | H | $SO_2$ | a | — |

Key:

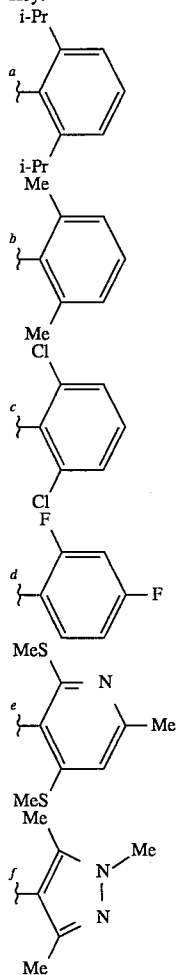

TABLE 6-continued

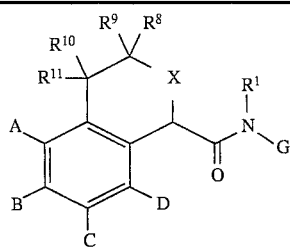

| Ex. No. | R¹ | R⁸ | R⁹ | R¹⁰ | R¹¹ | A | B | C | D | X | G | m.p. |
|---|---|---|---|---|---|---|---|---|---|---|---|---|

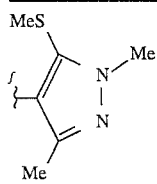

TABLE 7

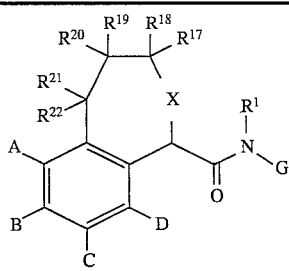

| Ex. No. | R¹ | R¹⁷ | R¹⁸ | R¹⁹ | R²⁰ | R²¹ | R²² | A | B | C | D | X | G | mp |
|---|---|---|---|---|---|---|---|---|---|---|---|---|---|---|
| 873 | H | H | H | H | H | H | H | H | CH₃O | CH₃O | H | S | a | — |
| 874 | H | H | H | H | H | H | H | H | CH₃O | CH₃O | H | S | b | — |
| 875 | H | H | H | H | H | H | H | H | CH₃O | CH₃O | H | S | c | — |
| 876 | H | H | H | H | H | H | H | H | CH₃O | CH₃O | H | S | d | — |
| 877 | H | H | H | H | H | H | H | H | CH₃O | CH₃O | H | O | a | — |
| 878 | H | H | H | H | H | H | H | H | CH₃O | CH₃O | H | O | b | — |
| 879 | H | H | H | H | H | H | H | H | CH₃O | CH₃O | H | O | c | — |
| 880 | H | H | H | H | H | H | H | H | CH₃O | CH₃O | H | O | d | — |
| 881 | H | H | H | H | H | H | H | H | CH₃O | C₅H₁₁O | H | S | a | — |
| 882 | H | H | H | H | H | H | H | H | CH₃O | C₅H₁₁O | H | S | b | — |
| 883 | H | H | H | H | H | H | H | H | CH₃O | C₅H₁₁O | H | S | c | 165–167 |
| 884 | H | H | H | H | H | H | H | H | CH₃O | C₅H₁₁O | H | S | d | — |
| 885 | H | H | H | H | H | H | H | H | CH₃O | C₅H₁₁O | H | O | a | — |
| 886 | H | H | H | H | H | H | H | H | CH₃O | C₅H₁₁O | H | O | b | — |
| 887 | H | H | H | H | H | H | H | H | CH₃O | C₅H₁₁O | H | O | c | — |
| 888 | H | H | H | H | H | H | H | H | CH₃O | C₅H₁₁O | H | O | d | — |
| 889 | H | H | H | H | H | H | H | CH₃O | H | H | CH₃O | S | a | — |
| 890 | H | H | H | H | H | H | H | CH₃O | H | H | CH₃O | S | b | — |
| 891 | H | H | H | H | H | H | H | CH₃O | H | H | CH₃O | S | c | — |
| 892 | H | H | H | H | H | H | H | CH₃O | H | H | CH₃O | S | d | — |
| 893 | H | H | H | H | H | H | H | CH₃O | H | H | CH₃O | O | a | — |
| 894 | H | H | H | H | H | H | H | CH₃O | H | H | CH₃O | O | b | — |
| 895 | H | H | H | H | H | H | H | CH₃O | H | H | CH₃O | O | c | — |
| 896 | H | H | H | H | H | H | H | CH₃O | H | H | CH₃O | O | d | — |
| 897 | H | H | H | C₄H₉ | H | H | H | H | CH₃O | CH₃O | H | S | a | — |
| 898 | H | H | H | C₄H₉ | H | H | H | H | CH₃O | CH₃O | H | S | b | — |
| 899 | H | H | H | C₄H₉ | H | H | H | H | CH₃O | CH₃O | H | S | c | 143–145 |
| 900 | H | H | H | C₅H₁₁ | H | H | H | H | CH₃O | CH₃O | H | S | c | — |
| 901 | H | H | H | C₄H₉ | H | H | H | H | CH₃O | CH₃O | H | O | a | — |
| 902 | H | H | H | C₄H₉ | H | H | H | H | CH₃O | CH₃O | H | O | b | — |
| 903 | H | H | H | C₄H₉ | H | H | H | H | CH₃O | CH₃O | H | O | c | — |
| 904 | H | H | H | C₄H₉ | H | H | H | H | CH₃O | CH₃O | H | O | d | — |
| 905 | H | H | H | C₄H₉ | H | H | H | H | CH₃O | C₅H₁₁O | H | S | a | — |
| 906 | H | H | H | C₄H₉ | H | H | H | H | CH₃O | C₅H₁₁O | H | S | b | — |

TABLE 7-continued

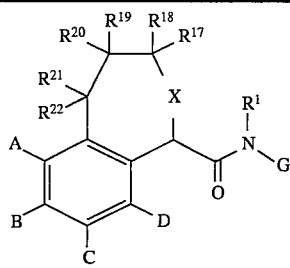

| Ex. No. | $R^1$ | $R^{17}$ | $R^{18}$ | $R^{19}$ | $R^{20}$ | $R^{21}$ | $R^{22}$ | A | B | C | D | X | G | mp |
|---|---|---|---|---|---|---|---|---|---|---|---|---|---|---|
| 907 | H | H | H | $C_4H_9$ | H | H | H | H | $CH_3O$ | $C_5H_{11}O$ | H | S | c | 157–160 |
| 908 | H | H | H | $C_4H_9$ | H | H | H | H | $CH_3O$ | $C_5H_{11}O$ | H | S | d | — |
| 909 | H | H | H | $C_4H_9$ | H | H | H | H | $CH_3O$ | $C_5H_{11}O$ | H | O | a | — |
| 910 | H | H | H | $C_4H_9$ | H | H | H | H | $CH_3O$ | $C_5H_{11}O$ | H | O | b | — |
| 911 | H | H | H | $C_4H_9$ | H | H | H | H | $CH_3O$ | $C_5H_{11}O$ | H | O | c | — |
| 912 | H | H | H | $C_4H_9$ | H | H | H | H | $CH_3O$ | $C_5H_{11}O$ | H | O | d | — |
| 913 | H | H | H | $C_4H_9$ | H | H | H | $CH_3O$ | H | H | $CH_3O$ | S | a | — |
| 914 | H | H | H | $C_4H_9$ | H | H | H | $CH_3O$ | H | H | $CH_3O$ | S | b | — |
| 915 | H | H | H | $C_4H_9$ | H | H | H | $CH_3O$ | H | H | $CH_3O$ | S | c | — |
| 916 | H | H | H | $C_4H_9$ | H | H | H | $CH_3O$ | H | H | $CH_3O$ | S | d | — |
| 917 | H | H | H | $C_4H_9$ | H | H | H | $CH_3O$ | H | H | $CH_3O$ | O | a | — |
| 918 | H | H | H | $C_4H_9$ | H | H | H | $CH_3O$ | H | H | $CH_3O$ | O | b | — |
| 919 | H | H | H | $C_4H_9$ | H | H | H | $CH_3O$ | H | H | $CH_3O$ | O | c | — |
| 920 | H | H | H | $C_4H_9$ | H | H | H | $CH_3O$ | H | H | $CH_3O$ | O | d | — |
| 921 | H | H | H | $C_4H_9$ | H | $C_4H_9$ | H | H | $CH_3O$ | $CH_3O$ | H | S | a | — |
| 922 | H | H | H | $C_4H_9$ | H | $C_4H_9$ | H | H | $CH_3O$ | $CH_3O$ | H | S | b | — |
| 923 | H | H | H | $C_4H_9$ | H | $C_4H_9$ | H | H | $CH_3O$ | $CH_3O$ | H | S | c | — |
| 924 | H | H | H | $C_4H_9$ | H | $C_4H_9$ | H | H | $CH_3O$ | $CH_3O$ | H | S | d | — |
| 925 | H | H | H | $C_4H_9$ | H | $C_4H_9$ | H | H | $CH_3O$ | $CH_3O$ | H | O | a | — |
| 926 | H | H | H | $C_4H_9$ | H | $C_4H_9$ | H | H | $CH_3O$ | $CH_3O$ | H | O | b | — |
| 927 | H | H | H | $C_4H_9$ | H | $C_4H_9$ | H | H | $CH_3O$ | $CH_3O$ | H | O | c | — |
| 928 | H | H | H | $C_4H_9$ | H | $C_4H_9$ | H | H | $CH_3O$ | $CH_3O$ | H | O | d | — |
| 929 | H | H | H | $C_4H_9$ | H | $C_4H_9$ | H | H | $CH_3O$ | $C_5H_{11}O$ | H | S | a | — |
| 930 | H | H | H | $C_4H_9$ | H | $C_4H_9$ | H | H | $CH_3O$ | $C_5H_{11}O$ | H | S | b | — |
| 931 | H | H | H | $C_4H_9$ | H | $C_4H_9$ | H | H | $CH_3O$ | $C_5H_{11}O$ | H | S | c | — |
| 932 | H | H | H | $C_4H_9$ | H | $C_4H_9$ | H | H | $CH_3O$ | $C_5H_{11}O$ | H | S | d | — |
| 933 | H | H | H | $C_4H_9$ | H | $C_4H_9$ | H | H | $CH_3O$ | $C_5H_{11}O$ | H | O | a | — |
| 934 | H | H | H | $C_4H_9$ | H | $C_4H_9$ | H | H | $CH_3O$ | $C_5H_{11}O$ | H | O | b | — |
| 935 | H | H | H | $C_4H_9$ | H | $C_4H_9$ | H | H | $CH_3O$ | $C_5H_{11}O$ | H | O | c | — |
| 936 | H | H | H | $C_4H_9$ | H | $C_4H_9$ | H | H | $CH_3O$ | $C_5H_{11}O$ | H | O | d | — |
| 937 | H | H | H | $C_4H_9$ | H | $C_4H_9$ | H | $CH_3O$ | H | H | $CH_3O$ | S | a | — |
| 938 | H | H | H | $C_4H_9$ | H | $C_4H_9$ | H | $CH_3O$ | H | H | $CH_3O$ | S | b | — |
| 939 | H | H | H | H | H | H | H | $CH_3O$ | H | H | $CH_3O$ | S | c | — |
| 940 | H | H | H | $C_4H_9$ | H | $C_4H_9$ | H | $CH_3O$ | H | H | $CH_3O$ | S | d | — |
| 941 | H | H | H | $C_4H_9$ | H | $C_4H_9$ | H | $CH_3O$ | H | H | $CH_3O$ | O | a | — |
| 942 | H | H | H | $C_4H_9$ | H | $C_4H_9$ | H | $CH_3O$ | H | H | $CH_3O$ | O | b | — |
| 943 | H | H | H | $C_4H_9$ | H | $C_4H_9$ | H | $CH_3O$ | H | H | $CH_3O$ | O | c | — |
| 944 | H | H | H | $C_4H_9$ | H | $C_4H_9$ | H | $CH_3O$ | H | H | $CH_3O$ | O | d | — |
| 945 | H | H | H | $C_8H_{17}$ | H | H | H | H | $CH_3O$ | $CH_3O$ | H | S | a | — |
| 946 | H | H | H | $C_8H_{17}$ | H | H | H | H | $CH_3O$ | $CH_3O$ | H | S | b | — |
| 947 | H | H | H | $C_8H_{17}$ | H | H | H | H | $CH_3O$ | $CH_3O$ | H | S | c | — |
| 948 | H | H | H | $C_8H_{17}$ | H | H | H | H | $CH_3O$ | $CH_3O$ | H | S | d | — |
| 949 | H | H | H | $C_8H_{17}$ | H | H | H | H | $CH_3O$ | $CH_3O$ | H | O | a | — |
| 950 | H | H | H | $C_8H_{17}$ | H | H | H | H | $CH_3O$ | $CH_3O$ | H | O | b | — |
| 951 | H | H | H | $C_8H_{17}$ | H | H | H | H | $CH_3O$ | $CH_3O$ | H | O | c | — |
| 952 | H | H | H | $C_8H_{17}$ | H | H | H | H | $CH_3O$ | $CH_3O$ | H | O | d | — |
| 953 | H | H | H | $C_8H_{17}$ | H | H | H | H | $CH_3O$ | $C_5H_{11}O$ | H | S | a | — |
| 954 | H | H | H | $C_8H_{17}$ | H | H | H | H | $CH_3O$ | $C_5H_{11}O$ | H | S | b | — |
| 955 | H | H | H | $C_8H_{17}$ | H | H | H | H | $CH_3O$ | $C_5H_{11}O$ | H | S | c | — |
| 956 | H | H | H | $C_8H_{17}$ | H | H | H | H | $CH_3O$ | $C_5H_{11}O$ | H | S | d | — |
| 957 | H | H | H | $C_8H_{17}$ | H | H | H | H | $CH_3O$ | $C_5H_{11}O$ | H | O | a | — |
| 958 | H | H | H | $C_8H_{17}$ | H | H | H | H | $CH_3O$ | $C_5H_{11}O$ | H | O | b | — |
| 959 | H | H | H | $C_8H_{17}$ | H | H | H | H | $CH_3O$ | $C_5H_{11}O$ | H | O | c | — |
| 960 | H | H | H | $C_8H_{17}$ | H | H | H | H | $CH_3O$ | $C_5H_{11}O$ | H | O | d | — |
| 961 | H | H | H | $C_8H_{17}$ | H | H | H | $CH_3O$ | H | H | $CH_3O$ | S | a | — |
| 962 | H | H | H | $C_8H_{17}$ | H | H | H | $CH_3O$ | H | H | $CH_3O$ | S | b | — |
| 963 | H | H | H | $C_8H_{17}$ | H | H | H | $CH_3O$ | H | H | $CH_3O$ | S | c | — |
| 964 | H | H | H | $C_8H_{17}$ | H | H | H | $CH_3O$ | H | H | $CH_3O$ | S | d | — |
| 965 | H | H | H | $C_8H_{17}$ | H | H | H | $CH_3O$ | H | H | $CH_3O$ | O | a | — |
| 966 | H | H | H | $C_8H_{17}$ | H | H | H | $CH_3O$ | H | H | $CH_3O$ | O | b | — |
| 967 | H | H | H | $C_8H_{17}$ | H | H | H | $CH_3O$ | H | H | $CH_3O$ | O | c | — |
| 968 | H | H | H | $C_8H_{17}$ | H | H | H | $CH_3O$ | H | H | $CH_3O$ | O | d | — |

TABLE 7-continued

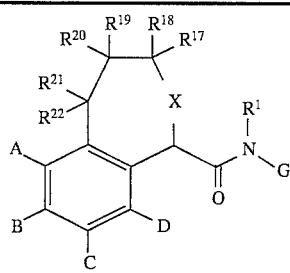

| Ex. No. | R¹ | R¹⁷ | R¹⁸ | R¹⁹ | R²⁰ | R²¹ | R²² | A | B | C | D | X | G | mp |
|---|---|---|---|---|---|---|---|---|---|---|---|---|---|---|
| 969 | H | H | H | C₈H₁₇ | H | H | H | CH₃O | H | H | CH₃O | SO | a | — |
| 970 | H | H | H | C₈H₁₇ | H | H | H | CH₃O | H | H | CH₃O | SO₂ | a | — |
| 971 | CH₃ | H | H | C₈H₁₇ | H | H | H | CH₃O | H | H | CH₃O | S | a | — |

Key:

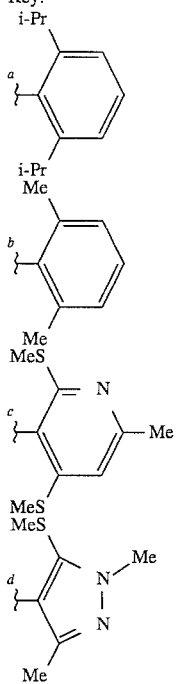

TABLE 8

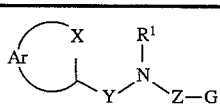

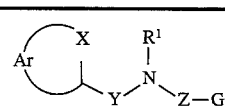

| Ex. No. | A | X | Y | R¹ | Z | G | m.p. |
|---|---|---|---|---|---|---|---|
| 972 | a | S | CH₂ | H | bond | j | — |
| 973 | b | O | CH₂ | H | bond | j | — |
| 974 | c | S | CH₂ | H | bond | j | — |
| 975 | d | S | CH₂ | H | bond | j | — |
| 976 | e | O | CH₂ | H | bond | j | — |
| 977 | f | S | CH₂ | H | bond | j | — |
| 978 | g | O | CH₂ | H | bond | j | — |
| 979 | h | O | CH₂ | H | bond | j | — |
| 980 | h | S | CH₂ | H | bond | j | — |
| 981 | m | S | CH₂ | H | bond | j | — |
| 982 | c | S | CH₂NHC=O | H | bond | k | — |
| 983 | d | S | CH₂NHC=O | H | bond | k | — |
| 984 | e | O | CH₂NHC=O | H | bond | k | — |
| 985 | f | S | CH₂NHC=O | H | bond | k | — |
| 986 | g | O | CH₂NHC=O | H | bond | k | — |
| 987 | h | O | CH₂NHC=O | H | bond | k | — |
| 988 | h | S | CH₂NHC=O | H | bond | k | — |
| 989 | b | O | CH₂NHC=O | H | bond | k | — |
| 990 | a | S | C=O | H | CH₂ | L | — |
| 991 | a | S | C=O | H | CHCH₃ | C₆H₅ | — |
| 992 | b | O | C=O | H | CH₂ | L | — |
| 993 | b | O | C=O | H | CHCH₃ | C₆H₅ | — |
| 994 | c | S | C=O | H | CH₂ | L | — |
| 995 | c | S | C=O | H | CHCH₃ | C₆H₅ | — |

TABLE 8-continued $$\text{Ar}\underset{Y}{\overset{X}{\bigcirc}}\underset{N}{\overset{R^1}{\underset{Z-G}{|}}}$$

| Ex. No. | A | X | Y | R¹ | Z | G | m.p. |
|---|---|---|---|---|---|---|---|
| 996 | d | S | C=O | H | CH₂ | L | — |
| 997 | d | S | C=O | H | CHCH₃ | C₆H₅ | — |
| 998 | e | O | C=O | H | CH₂ | L | — |
| 999 | e | O | C=O | H | CHCH₃ | C₆H₅ | — |
| 1000 | f | S | C=O | H | CH₂ | L | — |
| 1001 | f | S | C=O | H | CHCH₃ | C₆H₅ | — |
| 1002 | g | O | C=O | H | CH₂ | L | — |
| 1003 | g | O | C=O | H | CHCH₃ | C₆H₅ | — |
| 1004 | h | O | C=O | H | CH₂ | L | — |
| 1005 | h | O | C=O | H | CHCH₃ | C₆H₅ | — |
| 1006 | h | S | C=O | H | CH₂ | L | — |
| 1007 | h | S | C=O | H | CHCH₃ | C₆H₅ | — |
| 1008 | m | S | C=O | H | CH₂ | L | — |
| 1009 | m | S | C=O | H | CHCH₃ | C₆H₅ | — |
| 1010 | a | S | CH₂ | H | CH₂ | L | — |
| 1011 | a | S | CH₂ | H | CHCH₃ | C₆H₅ | — |
| 1012 | b | O | CH₂ | H | CH₂ | L | — |
| 1013 | b | O | CH₂ | H | CHCH₃ | C₆H₅ | — |
| 1014 | c | S | CH₂ | H | CH₂ | L | — |
| 1015 | c | S | CH₂ | H | CHCH₃ | C₆H₅ | — |
| 1016 | d | S | CH₂ | H | CH₂ | L | — |
| 1017 | d | S | CH₂ | H | CHCH₃ | C₆H₅ | — |
| 1018 | e | O | CH₂ | H | CH₂ | L | — |
| 1019 | e | O | CH₂ | H | CHCH₃ | C₆H₅ | — |
| 1020 | f | S | CH₂ | H | CH₂ | L | — |
| 1021 | f | S | CH₂ | H | CHCH₃ | C₆H₅ | — |
| 1022 | g | O | CH₂ | H | CH₂ | L | — |
| 1023 | g | O | CH₂ | H | CHCH₃ | C₆H₅ | — |
| 1024 | h | O | CH₂ | H | CH₂ | L | — |
| 1025 | h | O | CH₂ | H | CHCH₃ | C₆H₅ | — |
| 1026 | h | S | CH₂ | H | CH₂ | L | — |
| 1027 | h | S | CH₂ | H | CHCH₃ | C₆H₅ | — |
| 1028 | m | S | CH₂ | H | CH₂ | L | — |
| 1029 | m | S | CH₂ | H | CHCH₃ | C₆H₅ | — |
| 1030 | i | S | CH₂NHC=O | H | CH₂ | L | — |
| 1031 | i | S | CH₂NHC=O | H | CHCH₃ | C₆H₅ | — |
| 1032 | b | O | CH₂NHC=O | H | CH₂ | L | — |
| 1033 | b | O | CH₂NHC=O | H | CHCH₃ | C₆H₅ | — |
| 1034 | c | S | CH₂NHC=O | H | CH₂ | L | — |
| 1035 | c | S | CH₂NHC=O | H | CHCH₃ | C₆H₅ | — |
| 1036 | d | S | CH₂NHC=O | H | CH₂ | L | — |
| 1037 | d | S | CH₂NHC=O | H | CHCH₃ | C₆H₅ | — |
| 1038 | e | O | CH₂NHC=O | H | CH₂ | L | — |
| 1039 | e | O | CH₂NHC=O | H | CHCH₃ | C₆H₅ | — |
| 1040 | f | S | CH₂NHC=O | H | CH₂ | L | — |
| 1041 | f | S | CH₂NHC=O | H | CHCH₃ | C₆H₅ | — |
| 1042 | g | O | CH₂NHC=O | H | CH₂ | L | — |
| 1043 | g | O | CH₂NHC=O | H | CHCH₃ | C₆H₅ | — |
| 1044 | h | O | CH₂NHC=O | H | CH₂ | L | — |
| 1045 | h | O | CH₂NHC=O | H | CHCH₃ | C₆H₅ | — |
| 1046 | h | S | CH₂NHC=O | H | CH₂ | L | — |
| 1047 | h | S | CH₂NHC=O | H | CHCH₃ | C₆H₅ | — |
| 1048 | a | SO₂ | C=O | CH₃ | CH₂ | L | — |
| 1049 | m | S | CH₂NHC=O | H | CH₂ | L | — |
| 1050 | m | S | CH₂NHC=O | H | CHCH₃ | C₆H₅ | — |

Key:

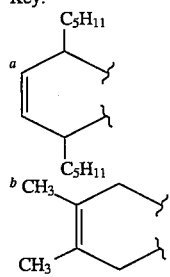

TABLE 8-continued

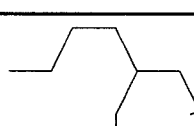

| Ex. No. | A | X | Y | R¹ | Z | G | m.p. |
|---|---|---|---|---|---|---|---|

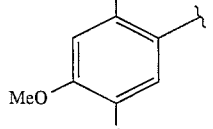

What is claimed is:

1. A compound of Formula I:

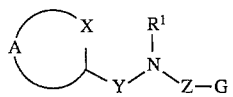

(I)

or a pharmaceutically acceptable salt form thereof, wherein:

A is

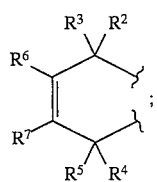

X is selected from: —O—, —S—, —S(=O)—, and —S(=O)$_2$—;

Y is —C(=O)—;

Z is selected from a bond and —(CH$_2$)$_p$—;

p is an integer selected from 1–5;

G is selected from:
phenyl substituted with 1–3 R$^{30}$, and
naphthyl substituted with 0–3 R$^{30}$;

G may also be selected from a heterocyclic group selected from:

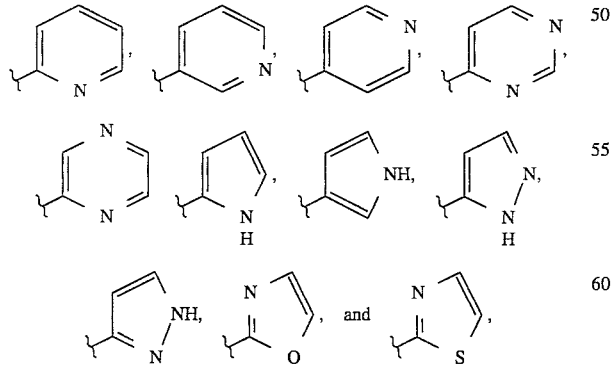

each such heterocyclic group being optionally fused to a benzene ring, and each such heterocyclic group and fused benzene ring being substituted with 0–3 R$^{30}$ or 0–3 phenyl groups, each phenyl being substituted with 0–3 R$^{30}$;

G may also be chosen from the following heterocyclic groups:

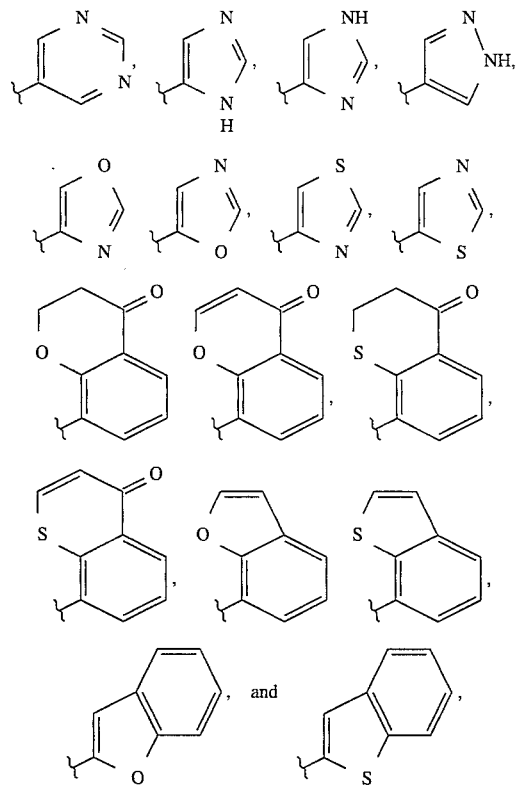

each such heterocyclic group being substituted with 0–3 R$^{30}$ or 0–3 phenyl groups, each phenyl being substituted with 0–3 R$^{30}$;

R$^1$ is selected from:
H,
C$_1$–C$_6$ alkyl,
C$_3$–C$_8$ cycloalkyl,
C$_4$–C$_9$ cycloalkylalkyl,
benzyl substituted with 0–3 R$^{30}$, and
phenyl substituted with 0–3 R$^{30}$;

R$^2$, R$^3$, R$^4$, R$^5$, R$^6$, and R$^7$ are independently selected from:
H,
C$_1$–C$_{13}$ alkyl,
C$_3$–C$_8$ cycloalkyl,
C$_3$–C$_8$ cycloalkyloxy,
C$_4$–C$_9$ cycloalkylalkyl,
C$_4$–C$_9$ cycloalkylalkyloxy,
C$_4$–C$_{12}$ alkenyl,
C$_4$–C$_{12}$ alkenyloxy,
C$_4$–C$_{12}$ alkynyl,
C$_4$–C$_{12}$ alkynyloxy,
C$_1$–C$_{10}$ alkoxy,
C$_2$–C$_{12}$ alkoxyalkyl,
C$_2$–C$_{12}$ alkoxyalkyloxy,
C$_3$–C$_{14}$ alkoxyalkoxyalkyl,
C$_2$–C$_{10}$ alkylcarbonyloxy,
C$_1$–C$_{10}$ alkylthio,
C$_2$–C$_{10}$ alkylthioalkyl,
C$_1$–C$_{10}$ haloalkyl,
aryl-(C$_1$–C$_5$ alkyl)-substituted with 0–3 R$^{30}$,
aryl-(C$_1$–C$_5$ alkyl)oxy substituted with 0–3 R$^{30}$, aryl substituted with 0–3 $R^{30}$, and
aryloxy substituted with 0–3 $R^{30}$;

$R^3$ and $R^4$ can also be taken together to form a
—$(CH_2)_q$— bridge;

q is an integer selected from 1–4;

$R^{30}$ is selected independently from: $C_1$–$C_{10}$ alkyl, $C_3$–$C_{10}$ cycloalkyl, $C_4$–$C_9$ cycloalkylalkyl, $C_1$–$C_4$ alkoxy, $C_1$–$C_4$ alkylthio, $C_2$–$C_8$ dialkylamino, halogen, $C_1$–$C_6$ haloalkyl, and nitro.

2. A compound of claim 1, or a pharmaceutically acceptable salt form thereof, wherein:

Z is a bond;

G is selected from:
phenyl substituted with 1–3 $R^{30}$, and
a heterocycle selected from:

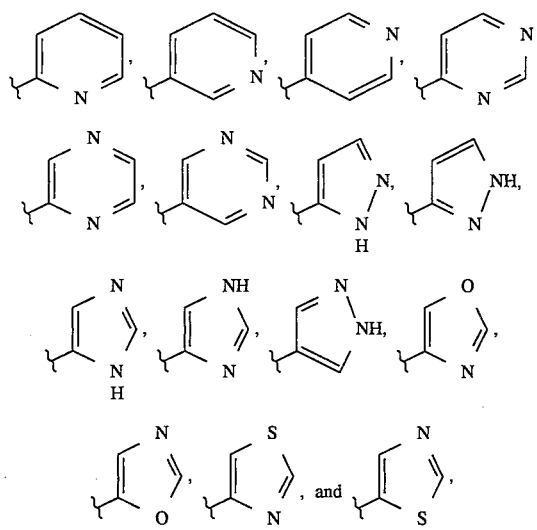

each such heterocyclic group being substituted with 0–3 $R^{30}$ or 0–3 phenyl groups, each phenyl being substituted with 0–3 $R^{30}$;

$R^1$ is selected from H, $C_1$–$C_4$ alkyl, $C_3$–$C_6$ branched alkyl, and $C_3$–$C_8$ cycloalkyl;

$R^2$, $R^3$, $R^4$, $R^5$, $R^6$, and $R^7$ are independently selected from:
H,
$C_1$–$C_{10}$ straight chain alkyl,
$C_3$–$C_6$ branched alkyl
$C_3$–$C_8$ cycloalkyl,
$C_1$–$C_{10}$ alkoxy,
$C_2$–$C_{10}$ alkoxyalkyl,
$C_2$–$C_{10}$ alkoxyalkyloxy,
benzyl substituted with 0–3 $R^{30}$,
benzyloxy substituted with 0–3 $R^{30}$,
phenyl substituted with 0–3 $R^{30}$, and
phenyloxy substituted with 0–3 $R^{30}$;

$R^3$ and $R^4$ can also be taken together to form —$CH_2$— or —$CH_2CH_2$—; and, $R^{30}$ is selected independently from: $C_1$–$C_6$ alkyl, $C_3$–$C_8$ cycloalkyl, $C_1$–$C_4$ alkoxy, $C_1$–$C_4$ alkylthio, and $C_2$–$C_8$ dialkylamino.

3. A compound of claim 1, or a pharmaceutically acceptable salt form thereof, wherein:

X is O or S;

Z is a bond;

G is selected from:
phenyl substituted with 1–3 $R^{30}$, and
a heterocyclic group selected from:

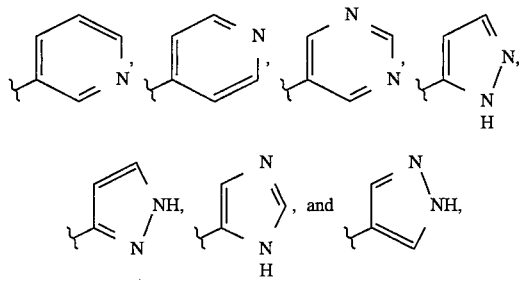

each such heterocyclic group being substituted with 0–3 $R^{30}$ or 0–3 phenyl groups, each phenyl being substituted with 0–3 $R^{30}$;

$R^1$ is H;

$R^2$, $R^3$, $R^4$, $R^5$, $R^6$, and $R^7$ are independently selected from:
H,
$C_1$–$C_{10}$ straight chain alkyl,
$C_3$–$C_6$ branched alkyl
$C_3$–$C_8$ cycloalkyl,
$C_1$–$C_{10}$ alkoxy,
$C_2$–$C_{10}$ alkoxyalkyl,
$C_2$–$C_{10}$ alkoxyalkyloxy,
benzyl substituted with 0–3 $R^{30}$,
benzyloxy substituted with 0–3 $R^{30}$,
phenyl substituted with 0–3 $R^{30}$, and
phenyloxy substituted with 0–3 $R^{30}$; and $R^{30}$ is selected independently from: $C_1$–$C_4$ straight chain alkyl, $C_3$–$C_6$ branched alkyl, $C_3$–$C_8$ cycloalkyl, $C_1$–$C_4$ alkoxy, $C_1$–$C_4$ alkylthio, and $C_2$–$C_8$ dialkylamino.

4. A compound of claim 1, or a pharmaceutically acceptable salt thereof, wherein:

X is S;

Z is a bond;

G is selected from:
phenyl substituted with 1–3 $R^{30}$, and
a heterocyclic group selected from:

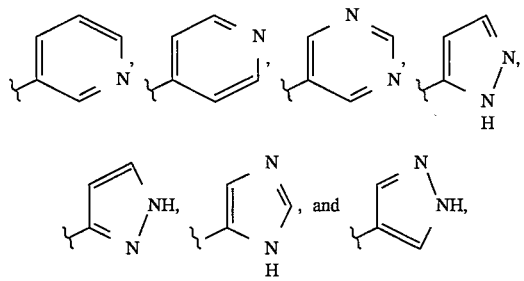

each such heterocyclic group being substituted with 0–3 $R^{30}$ or 0–3 phenyl groups, each phenyl being substituted with 0–3 $R^{30}$;

$R^1$ is H;

$R^3$ and $R^4$ are H;

$R^2$, $R^5$, $R^6$, and $R^7$ are independently selected from:
H,
$C_1$–$C_{10}$ straight chain alkyl,
$C_3$–$C_{10}$ branched alkyl
$C_3$–$C_{10}$ cycloalkyl,
$C_3$–$C_{14}$ cycloalkylalkyl,
$C_1$–$C_{10}$ alkoxy, and $C_2$–$C_{10}$ alkoxyalkyl;

$R^{30}$ is selected independently from: $C_1$–$C_{10}$ straight chain alkyl, $C_3$–$C_{10}$ branched alkyl, $C_3$–$C_{10}$ cycloalkyl, $C_1$–$C_4$ alkoxy, $C_1$–$C_4$ alkylthio, $C_2$–$C_8$ dialkylamino, halogen, and nitro.

5. A compound of claim 1, or a pharmaceutically acceptable salt thereof, selected from:

N-[2,4-bis(methylthio)-6-methylpyridin-3-yl]-3,6-dihydro-3,6-dimethyl-2H-thiopyran-2-carboxamide;

N-[2,4-bis(methylthio)-6-methylpyridin-3-yl]-3,6-dihydro-3,6-dipropyl-2H-thiopyran-2-carboxamide;

N-[2,4-bis(methylthio)-6-methylpyridin-3-yl]-3,6-dibutyl-3,6-dihydro-2H-thiopyran-2-carboxamide;

N-[2,4-bis(methylthio)-6-methylpyridin-3-yl]-3,6-dihydro-3,6-dipentyl-2H-thiopyran-2-carboxamide;

N-[2,4-bis(methylthio)-6-methylpyridin-3-yl]-3,6-dihexyl-3,6-dihydro-2H-thiopyran-2-carboxamide;

N-[2,4-bis(methylthio)-6-methylpyridin-3-yl]-3,6-diheptyl-3,6-dihydro-2H-thiopyran-2-carboxamide;

N-[2,4-bis(methylthio)-6-methylpyridin-3-yl]-3,6-dihydro-3,6-dioctyl-2H-thiopyran-2-carboxamide;

N-[2,4-bis(methylthio)-6-methylpyridin-3-yl]-3,6-dihydro-3,6-diphenyl-2H-thiopyran-2-carboxamide;

N-[2,4-bis(methylthio)-6-methylpyridin-3-yl]-3,6-bis-3-(cyclohexylthio)propyl-3,6-dihydro-2H-thiopyran-2-carboxamide;

N-(2,6-diisopropylphenyl)-3,6-dihydro-3,6-dipentyl-2H-thiopyran-2-carboxamide; and N-(2,6-diisopropylphenyl)-3,6-dihydro-4,5-dipentyl-2H-thiopyran-2-carboxamide.

6. A pharmaceutical composition comprising a compound of claim 1 and a pharmaceutically acceptable carrier.

7. A pharmaceutical composition comprising a compound of claim 2 and a pharmaceutically acceptable carrier.

8. A pharmaceutical composition comprising a compound of claim 3 and a pharmaceutically acceptable carrier.

9. A pharmaceutical composition comprising a compound of claim 4 and a pharmaceutically acceptable carrier.

10. A pharmaceutical composition comprising a compound of claim 5 and a pharmaceutically acceptable carrier.

11. A method of treating hypercholesterolemia or atherosclerosis in a mammal in need thereof comprising administering to the mammal a therapeutically effective amount of a compound of claim 1.

12. A method of treating hypercholesterolemia or atherosclerosis in a mammal in need thereof comprising administering to the mammal a therapeutically effective amount of a compound of claim 2.

13. A method of treating hypercholesterolemia or atherosclerosis in a mammal in need thereof comprising administering to the mammal a therapeutically effective amount of a compound of claim 3.

14. A method of treating hypercholesterolemia or atherosclerosis in a mammal in need thereof comprising administering to the mammal a therapeutically effective amount of a compound of claim 4.

15. A method of treating hypercholesterolemia or atherosclerosis in a mammal in need thereof comprising administering to the mammal a therapeutically effective amount of a compound of claim 5.

* * * * *